(12) United States Patent
Horiuchi et al.

(10) Patent No.: US 11,747,728 B2
(45) Date of Patent: Sep. 5, 2023

(54) COMPOUND, RESIN, COMPOSITION, RESIST PATTERN FORMATION METHOD, CIRCUIT PATTERN FORMATION METHOD AND METHOD FOR PURIFYING RESIN

(71) Applicant: Mitsubishi Gas Chemical Company, Inc., Tokyo (JP)

(72) Inventors: Junya Horiuchi, Hiratsuka (JP); Yu Okada, Hiratsuka (JP); Takashi Makinoshima, Hiratsuka (JP); Masatoshi Echigo, Tokyo (JP)

(73) Assignee: Mitsubishi Gas Chemical Company, Inc., Tokyo (JP)

( * ) Notice: Subject to any disclaimer, the term of this patent is extended or adjusted under 35 U.S.C. 154(b) by 213 days.

(21) Appl. No.: 17/044,772

(22) PCT Filed: May 27, 2019

(86) PCT No.: PCT/JP2019/020864
§ 371 (c)(1),
(2) Date: Oct. 1, 2020

(87) PCT Pub. No.: WO2019/230639
PCT Pub. Date: Dec. 5, 2019

(65) Prior Publication Data
US 2021/0109448 A1    Apr. 15, 2021

(30) Foreign Application Priority Data

May 28, 2018 (JP) ................. 2018-101599

(51) Int. Cl.
| | |
|---|---|
| *G03F 7/11* | (2006.01) |
| *C07C 39/15* | (2006.01) |
| *C07C 39/367* | (2006.01) |
| *C07C 49/83* | (2006.01) |
| *C08G 8/04* | (2006.01) |
| *C09D 161/12* | (2006.01) |
| *H01L 21/027* | (2006.01) |
| *H01L 21/311* | (2006.01) |

(52) U.S. Cl.
CPC ............... *G03F 7/11* (2013.01); *C07C 39/15* (2013.01); *C07C 39/367* (2013.01); *C07C 49/83* (2013.01); *C08G 8/04* (2013.01); *C09D 161/12* (2013.01); *H01L 21/0274* (2013.01); *H01L 21/31144* (2013.01)

(58) Field of Classification Search
CPC ........ G03F 7/11; G03F 7/0005; G03F 7/0226; G03F 7/039; G03F 7/091; G03F 7/094; G03F 7/20; G03F 7/26; C07C 39/15; C07C 39/367; C07C 49/83; C08G 8/04; C09D 161/12; H01L 21/0274; H01L 21/31144
USPC .......... 438/703; 430/270.1, 271.1, 272.1, 311
See application file for complete search history.

(56) References Cited

U.S. PATENT DOCUMENTS

| | | |
|---|---|---|
| 2,625,568 A | 1/1953 | Young et al. |
| 2005/0255712 A1 | 11/2005 | Kato et al. |
| 2008/0153031 A1 | 6/2008 | Echigo et al. |
| 2009/0203851 A1 | 8/2009 | Benthem Van |
| 2014/0248561 A1 | 9/2014 | Echigo et al. |
| 2015/0090691 A1 | 4/2015 | Echigo et al. |
| 2016/0068709 A1 | 3/2016 | Endo et al. |
| 2017/0073288 A1* | 3/2017 | Makinoshima .......... C08G 8/10 |

FOREIGN PATENT DOCUMENTS

| | | |
|---|---|---|
| DE | 46455 A1 | 3/1966 |
| EP | 3257835 A1 | 12/2017 |
| JP | H03-232836 A | 10/1991 |
| JP | H06-107768 A | 4/1994 |
| JP | H06-136091 A | 5/1994 |
| JP | H08-087110 A | 4/1996 |
| JP | H08-127552 A | 5/1996 |
| JP | H09-2987 A | 1/1997 |
| JP | H09-110761 A | 4/1997 |
| JP | H09-218511 A | 8/1997 |
| JP | H09-218512 A | 8/1997 |
| JP | 2002-334869 A | 11/2002 |

(Continued)

OTHER PUBLICATIONS

International Search Report for PCT/JP2019/020864, dated Aug. 13, 2019, and English Translation submitted herewith (6 pages).

(Continued)

*Primary Examiner* — Caleen O Sullivan
(74) *Attorney, Agent, or Firm* — Fitch, Even, Tabin & Flannery LLP

(57) ABSTRACT

An object of the present invention is to provide a new compound that is useful as a film forming material for lithography and the like. The above object can be achieved by a compound represented by the following formula (1).

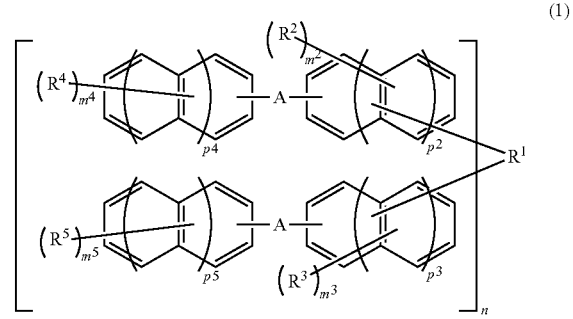

18 Claims, No Drawings

(56) References Cited

FOREIGN PATENT DOCUMENTS

| JP | 2004-177668 A | 6/2004 |
| JP | 2004-271838 A | 9/2004 |
| JP | 2005-134434 A | 6/2005 |
| JP | 2005-250434 A | 9/2005 |
| JP | 2005-326838 A | 11/2005 |
| JP | 2007-226170 A | 9/2007 |
| JP | 2007-226204 A | 9/2007 |
| JP | 2008-145539 A | 6/2008 |
| JP | 2008-216530 A | 9/2008 |
| JP | 2009-173623 A | 8/2009 |
| JP | 2009-538943 A | 11/2009 |
| JP | 2010-138393 A | 6/2010 |
| JP | 2015-174877 A | 10/2015 |
| JP | 2015-187668 A | 10/2015 |
| WO | 2004/066377 A1 | 8/2004 |
| WO | 2007/140941 A2 | 12/2007 |
| WO | 2013/024778 A1 | 2/2013 |
| WO | 2013/024779 A1 | 2/2013 |
| WO | 2014/185335 A1 | 11/2014 |
| WO | 2015/170524 A1 | 11/2015 |

OTHER PUBLICATIONS

Nakayama, T. et al., "A New Three-Component Photoresist Based on Calix[4]resorcinarene Derivative, a Cross-linker, and a Photo-acid Generator," Bulletin of the Chemical Society of Japan, 1998, vol. 71, No. 12, pp. 2979-2984.

Nemoto, T. et al., "Synthesis and Properties of a High-Molecular-Weight Organosoluble Bisphenol A Novolac," Polymer Journal, 2009, vol. 41, No. 4, pp. 338-342.

Okazaki, S. et al., "New Trends of Photoresists," CMC Publishing Co., Ltd., Sep. 2009, pp. 211-259. (Cited in Specification).

Thévenin, Marion et al., "Facile Formation of Methylenebis(chalcone)s through Unprecedented Methylenation Reaction. Application to Antiparasitic and Natural Product Synthesis," European Journal of Organic Chemistry, 2017, pp. 2986-2992.

* cited by examiner

COMPOUND, RESIN, COMPOSITION, RESIST PATTERN FORMATION METHOD, CIRCUIT PATTERN FORMATION METHOD AND METHOD FOR PURIFYING RESIN

CROSS-REFERENCE TO RELATED APPLICATIONS

This application is a U.S. national phase application filed under 35 U.S.C. § 371 of International Application Number PCT/JP2019/020864, filed May 27, 2019, designating the United States, which claims priority from Japanese Application Number 2018-101599, filed May 28, 2018.

FIELD OF THE INVENTION

The present invention relates to a compound, a resin, a composition, a resist pattern formation method, a circuit pattern formation method, and a method for purifying the resin.

BACKGROUND OF THE INVENTION

In the production of semiconductor devices, fine processing is practiced by lithography using photoresist materials. In recent years, further miniaturization based on pattern rules has been demanded along with increase in the integration and speed of LSI (large scale integrated circuits). The light source for lithography used upon forming resist patterns has been shifted to ArF excimer laser (193 nm) having a shorter wavelength from KrF excimer laser (248 nm). The introduction of extreme ultraviolet (EUV, 13.5 nm) is also expected.

However, because conventional polymer-based resist materials have a molecular weight as large as about 10,000 to 100,000 and also wide molecular weight distribution, in lithography using such a polymer-based resist material, roughness occurs on a pattern surface; the pattern dimension becomes difficult to be controlled; and there is a limitation in miniaturization. Accordingly, various low molecular weight resist materials have been proposed so far in order to provide resist patterns having higher resolution. The low molecular weight resist materials are expected to provide resist patterns having high resolution and small roughness, because of their small molecular sizes.

Various materials are currently known as such low molecular weight resist materials. For example, an alkaline development type negative type radiation-sensitive composition (see, for example, Patent Literature 1 and Patent Literature 2) using a low molecular weight polynuclear polyphenolic compound as a main component has been suggested; and as a candidate of a low molecular weight resist material having high heat resistance, an alkaline development type negative type radiation-sensitive composition (see, for example, Patent Literature 3 and Non Patent Literature 1) using a low molecular weight cyclic polyphenolic compound as a main component has been suggested as well. Also, as a base compound of a resist material, a polyphenol compound is known to be capable of imparting high heat resistance despite a low molecular weight and useful for improving the resolution and roughness of a resist pattern (see, for example, Non Patent Literature 2).

In addition, the present inventors have proposed a resist composition containing a compound having a specific structure and an organic solvent (see Patent Literature 4) as a material that is excellent in etching resistance and is also soluble in a solvent and applicable to a wet process.

Also, as the miniaturization of resist patterns proceeds, the problem of resolution or the problem of collapse of resist patterns after development arises. Therefore, resists have been desired to have a thinner film. However, if resists merely have a thinner film, it is difficult to obtain the film thicknesses of resist patterns sufficient for supporting material processing. Therefore, there has been a need for a process of preparing a resist underlayer film between a resist and a semiconductor supporting material to be processed, and imparting functions as a mask for supporting material processing to this resist underlayer film in addition to a resist pattern.

Various resist underlayer films for such a process are currently known. For example, as a material for realizing resist underlayer films for lithography having the selectivity of a dry etching rate close to that of resists, unlike conventional resist underlayer films having a fast etching rate, an underlayer film forming material for a multilayer resist process containing a resin component having at least a substituent that generates a sulfonic acid residue by eliminating a terminal group under application of predetermined energy, and a solvent has been suggested (see Patent Literature 5). Also, in order to realize a resist underlayer film for lithography having the selectivity of a dry etching rate smaller than that of resists, a resist underlayer film material comprising a polymer having a specific repeat unit has been suggested (see Patent Literature 6). Furthermore, in order to realize a resist underlayer film for lithography having the selectivity of a dry etching rate smaller than that of semiconductor supporting materials, a resist underlayer film material comprising a polymer prepared by copolymerizing a repeat unit of an acenaphthylene and a repeat unit having a substituted or unsubstituted hydroxy group has been suggested (see Patent Literature 7).

Meanwhile, as materials having high etching resistance for this kind of resist underlayer film, amorphous carbon underlayer films formed by chemical vapour deposition (CVD) using methane gas, ethane gas, acetylene gas, or the like as a raw material are well known. However, resist underlayer film materials that can form resist underlayer films by a wet process such as spin coating or screen printing have been demanded from the viewpoint of a process.

The present inventors have also proposed an underlayer film forming composition for lithography containing a compound having a specific structure and an organic solvent (see Patent Literature 8) as a material that is excellent in etching resistance, has high heat resistance, and is soluble in a solvent and applicable to a wet process.

As for methods for forming an intermediate layer used in the formation of a resist underlayer film in a three-layer process, for example, a method for forming a silicon nitride film (see Patent Literature 9) and a CVD formation method for a silicon nitride film (see Patent Literature 10) are known. Also, as intermediate layer materials for a three-layer process, materials comprising a silsesquioxane-based silicon compound are known (see Patent Literature 11 and Patent Literature 12).

Various compositions have been further proposed as optical component forming compositions. For example, Patent Literature 13 discloses an energy beam curable resin composition for optical lens sheets comprising: an ionic liquid; a compound having a predetermined polyalkylene oxide structure and a (meth)acryloyl group; a predetermined (meth)acrylate monomer; and a photopolymerization initiator. Patent Literature 14 describes that a resin composition containing: a copolymer having a specific structural unit; a specific curing catalyst; and a solvent is suitably used for microlenses or for flattening films.

CITATION LIST

Patent Literature

Patent Literature 1: Japanese Patent Laid-Open No. 2005-326838
Patent Literature 2: Japanese Patent Laid-Open No. 2008-145539
Patent Literature 3: Japanese Patent Laid-Open No. 2009-173623
Patent Literature 4: International Publication No. WO 2013/024778
Patent Literature 5: Japanese Patent Laid-Open No. 2004-177668
Patent Literature 6: Japanese Patent Laid-Open No. 2004-271838
Patent Literature 7: Japanese Patent Laid-Open No. 2005-250434
Patent Literature 8: International Publication No. WO 2013/024779
Patent Literature 9: Japanese Patent Laid-Open No. 2002-334869
Patent Literature 10: International Publication No. WO 2004/066377
Patent Literature 11: Japanese Patent Laid-Open No. 2007-226170
Patent Literature 12: Japanese Patent Laid-Open No. 2007-226204
Patent Literature 13: Japanese Patent Laid-Open No. 2010-138393
Patent Literature 14: Japanese Patent Laid-Open No. 2015-174877

Non Patent Literature

Non Patent Literature 1: T. Nakayama, M. Nomura, K. Haga, M. Ueda: Bull. Chem. Soc. Jpn., 71, 2979 (1998)
Non Patent Literature 2: Shinji Okazaki et al., "New Trends of Photoresists", CMC Publishing Co., Ltd., September 2009, pp. 211-259

SUMMARY OF INVENTION

However, it has been required for film forming materials for lithography or optical component forming materials to have high levels of solubility in organic solvents, etching resistance and resist pattern formability at the same time.

Therefore, the present invention has an object to provide a new compound that is particularly useful as a film forming material for lithography or an optical component forming material and a resin having a constitutional unit derived from this new compound, a composition, a method for forming a resist pattern, a method for forming an insulating film, a method for forming a circuit pattern, and a method for purifying the above compound or resin.

The present inventors have, as a result of devoted examinations to solve the problems described above, found out that a new compound having a specific structure can be obtained and that the new compound obtained is particularly useful as a film forming material for lithography or an optical component forming material, leading to completion of the present invention.

More specifically, the present invention is as follows.

[1]

A compound represented by the following formula (1):

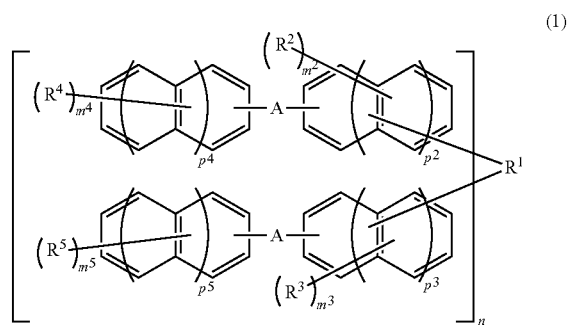

wherein

A is a group having 1 to 12 carbon atoms;

$R^1$ is a 2n-valent group having 1 to 30 carbon atoms;

$R^2$ to $R^5$ are each independently a linear, branched, or cyclic alkyl group having 1 to 10 carbon atoms, an alkoxy group having 1 to 10 carbon atoms, an aryl group having 6 to 10 carbon atoms, an alkenyl group having 2 to 10 carbon atoms, an alkynyl group having 2 to 10 carbon atoms, a thiol group, or a hydroxyl group;

at least one $R^4$ and/or at least one $R^5$ is a hydroxy group and/or a thiol group;

$m^2$ and $m^3$ are each independently an integer of 0 to 8;

$m^4$ and $m^5$ are each independently an integer of 0 to 9;

n is an integer of 1 to 4; and $p^2$ to $p^5$ are each independently an integer of 0 to 2.

[1-1]

The compound according to [1], wherein A is selected from the group consisting of a carbonyl group, a thiocarbonyl group, a methylene group, an ethylene group, an propylene group, a butylene group, a hexafluoropropylene group, a phenylethylene group, a diphenylmethylene group, a cyclohexylene group, a trimethylcyclohexylene group, and a cyclododecylene group.

[1-2]

The compound according to [1] or [1-1], wherein $R^1$ is a 2n-valent hydrocarbon group having 1 to 30 carbon atoms.

[1-3]

The compound according to [1-2], wherein the 2n-valent hydrocarbon group having 1 to 30 carbon atoms comprises an aromatic group.

[2]

The compound according to any one of [1] to [1-3], wherein, in the above formula (1), at least one $R^2$ and/or at least one $R^3$ is a hydroxy group and/or a thiol group.

[3]

The compound according to any one of [1] to [2], wherein the compound represented by the above formula (1) is a compound represented by the following formula (1a):

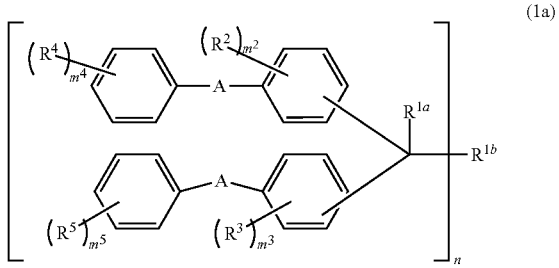

wherein

A, $R^2$ to $R^5$, and n are each as defined in the above formula (1);

$R^{1a}$ is a hydrogen atom or a monovalent group having 1 to 10 carbon atoms;

$R^{1b}$ is an n-valent group having 1 to 25 carbon atoms;

$m^2$ and $m^3$ are each independently an integer of 0 to 4; and $m^4$ and $m^5$ are each independently an integer of 0 to 5.

[3-1]

The compound according to [3], wherein $R^{1b}$ is an n-valent hydrocarbon group having 1 to 25 carbon atoms.

[3-2]

The compound according to [3-1], wherein the n-valent hydrocarbon group having 1 to 25 carbon atoms comprises an aromatic group.

[4]

The compound according to any one of [3] to [3-2], wherein the compound represented by the above formula (1a) is a compound represented by the following formula (1b):

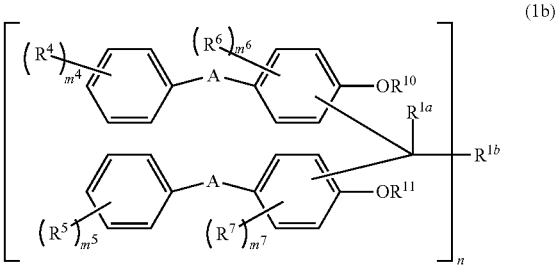

wherein

A, $R^4$, $R^5$, $R^{1a}$, $R^{1b}$, $m^4$, $m^5$, and n are each as defined in the above formula (1a);

$R^6$ and $R^7$ are each independently a linear, branched, or cyclic alkyl group having 1 to 10 carbon atoms, an aryl group having 6 to 10 carbon atoms, an alkenyl group having 2 to 10 carbon atoms, an alkynyl group having 2 to 10 carbon atoms, a thiol group, or a hydroxyl group;

$m^6$ and $m^7$ are each independently an integer of 0 to 3; and $R^{10}$ and $R^{11}$ are a hydrogen atom.

[5]

The compound according to [4], wherein the compound represented by the above formula (1b) is a compound represented by the following formula (1c):

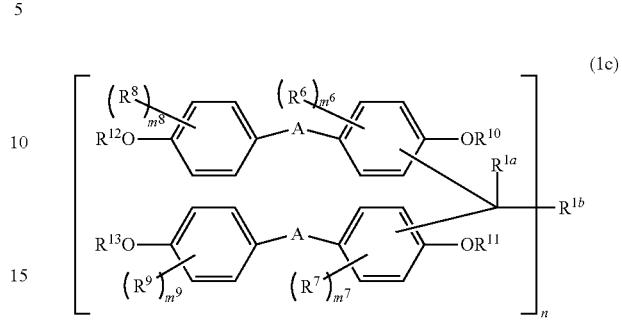

wherein

A, $R^{1a}$, $R^{1b}$, $R^6$, $R^7$, $R^{10}$, $R^{11}$, $m^6$, $m^7$, and n are each as defined in the above formula (1b);

$R^8$ and $R^9$ are each independently a linear, branched, or cyclic alkyl group having 1 to 10 carbon atoms, an aryl group having 6 to 10 carbon atoms, an alkenyl group having 2 to 10 carbon atoms, an alkynyl group having 2 to 10 carbon atoms, a thiol group, or a hydroxyl group;

$m^8$ and $m^9$ are each independently an integer of 0 to 4; and $R^{12}$ and $R^{13}$ are a hydrogen atom.

[6]

A resin having a constitutional unit derived from the compound according to any one of [1] to[5].

[7]

The resin according to [6], wherein the resin has a structure represented by the following formula (2):

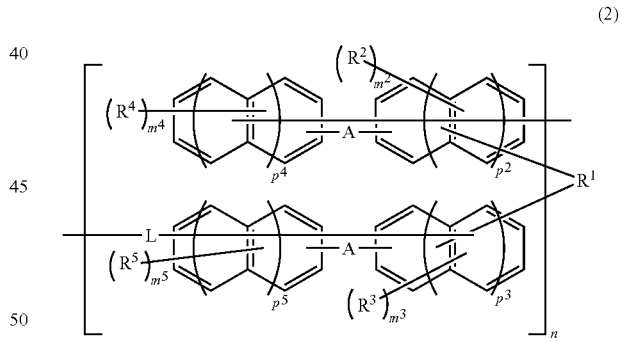

wherein

A, $R^1$ to $R^5$, $m^2$ to $m^5$, n, and $p^2$ to $p^5$ are each as defined in the above formula (1);

L is a single bond or a linking group.

[8]

A composition comprising one or more selected from the group consisting of the compound according to any of [1] to [5] and the resin according to [6] or [7].

[9]

The composition according to [8], further comprising a solvent.

[10]

The composition according to [8] or [9], further comprising an acid generating agent.

[11]
The composition according to any of [8] to [10], further comprising a crosslinking agent.
[12]
The composition according to any of [8] to [11], wherein the composition is used in film formation for lithography.
[13]
The composition according to any of [8] to [11], wherein the composition is used in optical component formation.
[14]
A method for forming a resist pattern, comprising the steps of:
  a photoresist layer formation step of forming a photoresist layer on a supporting material using the composition according to [12]; and
  a development step of irradiating a predetermined region of the photoresist layer formed through the photoresist layer formation step with radiation for development.
[15]
The method for forming a resist pattern according to [14], wherein the resist pattern is an insulating film pattern.
[16]
A method for forming a resist pattern, comprising:
  an underlayer film formation step of forming an underlayer film on a supporting material using the composition according to [12];
  a photoresist layer formation step of forming at least one photoresist layer on the underlayer film formed through the underlayer film formation step; and
  a step of irradiating a predetermined region of the photoresist layer formed through the photoresist layer formation step with radiation for development.
[17]
A method for forming a circuit pattern, comprising:
  an underlayer film formation step of forming an underlayer film on a supporting material using the composition according to [12];
  an intermediate layer film formation step of forming an intermediate layer film on the underlayer film formed through the underlayer film formation step;
  a photoresist layer formation step of forming at least one photoresist layer on the intermediate layer film formed through the intermediate layer film formation step;
  a resist pattern formation step of irradiating a predetermined region of the photoresist layer formed through the photoresist layer formation step with radiation for development, thereby forming a resist pattern;
  an intermediate layer film pattern formation step of etching the intermediate layer film with the resist pattern formed through the resist pattern formation step as a mask, thereby forming an intermediate layer film pattern;
  an underlayer film pattern formation step of etching the underlayer film with the intermediate layer film pattern formed through the intermediate layer film pattern formation step as a mask, thereby forming an underlayer film pattern; and
  a supporting material pattern formation step of etching the supporting material with the underlayer film pattern formed through the underlayer film pattern formation step as a mask, thereby forming a pattern on the supporting material.
[18]
A method for purifying the compound according to any of [1] to [5] or the resin according to [6] or [7], comprising:
  an extraction step of bringing a solution containing the compound or the resin and an organic solvent that does not inadvertently mix with water into contact with an acidic aqueous solution, thereby carrying out extraction.

The present invention can provide a new compound that is particularly useful as a film forming material for lithography or an optical component forming material and a resin having a constitutional unit derived from this new compound, a composition, a method for forming a resist pattern, a method for forming an insulating film, a method for forming a circuit pattern, and a method for purifying the above compound or resin.

DESCRIPTION OF EMBODIMENTS

Hereinafter, an embodiment of the present invention will be described (hereinafter, referred to as the "present embodiment"). The embodiment described below is given merely for illustrating the present invention. The present invention is not limited only by this embodiment.

[Compound]

A compound of the present embodiment is a compound represented by the following formula (1). The compound of the present embodiment has, for example, the following characteristics (1) to (4).

(1) The compound of the present embodiment has excellent solubility in an organic solvent (particularly, a safe solvent). Therefore, for example, when the compound of the present embodiment is used as a film forming material for lithography, films for lithography can be formed by a wet process such as spin coating or screen printing.

(2) In the compound of the present embodiment, the carbon concentration is relatively high and the oxygen concentration is relatively low. In addition, since the compound of the present embodiment has a phenolic hydroxy group and/or a phenolic thiol group in the molecule, it is useful for formation of a cured product through the reaction with a curing agent, but it can also form a cured product on its own through the crosslinking reaction of the phenolic hydroxy group and/or the phenolic thiol group upon baking at a high temperature. Due to the above, the compound of the present embodiment can exhibit high heat resistance, and when the compound of the present embodiment is used as a film forming material for lithography, degradation of the film upon baking at a high temperature is suppressed and a film for lithography excellent in etching resistance to oxygen plasma etching and the like can be formed.

(3) The compound of the present embodiment can exhibit high heat resistance and etching resistance, as described above, and also has excellent adhesiveness to a resist layer and a resist intermediate layer film material. Therefore, when the compound of the present embodiment is used as a film forming material for lithography, films for lithography excellent in resist pattern formability can be formed. The term "resist pattern formability" herein refers to a property in which there are no major defects in the resist pattern shape and both resolution and sensitivity are excellent.

(4) The compound of the present embodiment has a high refractive index due to its high aromatic ring density, and even after a heat treatment, coloration is suppressed and transparency is excellent.

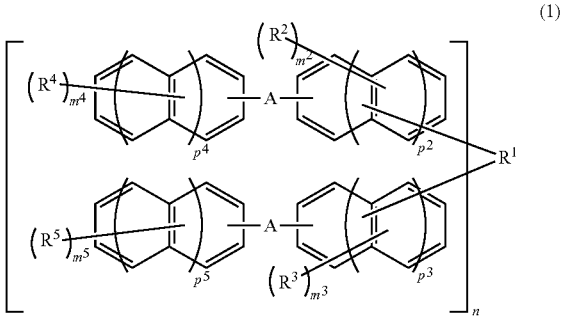

(1)

In the formula (1), A is a group having 1 to 12 carbon atoms (for example, a hydrocarbon group); $R^1$ is a 2n-valent group having 1 to 30 carbon atoms; $R^2$ to $R^5$ are each independently a linear, branched, or cyclic alkyl group having 1 to 10 carbon atoms, an aryl group having 6 to 10 carbon atoms, an alkenyl group having 2 to 10 carbon atoms, an alkynyl group having 2 to 10 carbon atoms, a thiol group, or a hydroxyl group; at least one $R^4$ and/or at least one $R^5$ is a hydroxy group and/or a thiol group; $m^2$ and $m^3$ are each independently an integer of 0 to 8; $m^4$ and $m^5$ are each independently an integer of 0 to 9; n is an integer of 1 to 4; and $p^2$ to $p^5$ are each independently an integer of 0 to 2.

In the formula (1), A is a group having 1 to 12 carbon atoms, and is a group that may form a divalent group. A may contain a heteroatom. Examples thereof include, but are not limited to, a carbonyl group, a thiocarbonyl group, a methylene group, an ethylene group, a propylene group, a butylene group, a hexafluoropropylene group, a phenylethylene group, a diphenylmethylene group, a cyclohexylene group, a trimethylcyclohexylene group, and a cyclododecylene group.

From the viewpoint of solubility, A preferably has an alicyclic structure, and more preferably has a cyclohexylene group, a trimethylcyclohexylene group, or a cyclododecylene group.

In addition, from the viewpoint of solubility, A preferably has a halogen, and more preferably is a hexafluoropropylene group.

From the viewpoint of heat resistance, A is preferably a hydrocarbon group having 1 to 3 carbon atoms, and more preferably has a carbonyl group, a methylene group, an ethylene group, or a propylene group.

In the formula (1), $R^1$ is a 2n-valent group having 1 to 30 carbon atoms, and each aromatic ring is bonded via this $R^1$. Specific examples of the 2n-valent group will be mentioned later.

In the formula (1), $R^2$ to $R^5$ are each independently a monovalent group selected from the group consisting of a linear, branched, or cyclic alkyl group having 1 to 10 carbon atoms, an alkoxy group having 1 to 10 carbon atoms, an aryl group having 6 to 10 carbon atoms, an alkenyl group having 2 to 10 carbon atoms, an alkynyl group having 2 to 10 carbon atoms, a thiol group, and a hydroxyl group. Examples of the alkyl group include a linear or branched alkyl group such as a methyl group, an ethyl group, a n-propyl group, an isopropyl group, a n-butyl group, an iso-butyl group, a sec-butyl group, a tert-butyl group, a pentyl group, and a hexyl group; and a cyclic alkyl group such as a cyclopentyl group and a cyclohexyl group. Examples of the alkoxy group include a methoxy group, an ethoxy group, and a propoxy group. Examples of the aryl group include a phenyl group, a naphthyl group, a tolyl group, and a xylyl group. Examples of the alkenyl group include an ethenyl group, a propenyl group, a butenyl group, a pentenyl group, and a hexenyl group. Examples of the alkynyl group include an ethynyl group, a 1-propynyl group, and a 2-propynyl group. However, at least one $R^4$ and/or at least one $R^5$ is a hydroxy group and/or a thiol group.

In the formula (1), $m^2$ and $m^3$ are each independently an integer of 0 to 8, preferably an integer of 0 to 4, and more preferably 1 or 2. $m^4$ and $m^5$ are each independently an integer of 0 to 9, preferably an integer of 0 to 4, and more preferably 1 or 2.

In the formula (1), n is an integer of 1 to 4, and is preferably an integer of 1 to 2.

In the formula (1), $p^2$ to $p^5$ are each independently an integer of 0 to 2, preferably an integer of 0 or 1, and more preferably 0.

Examples of the 2n-valent group $R^1$ include a divalent hydrocarbon group having 1 to 30 carbon atoms (for example, a linear or branched hydrocarbon group or a cyclic hydrocarbon group, such as an alkylene group) when n is 1; a tetravalent hydrocarbon group having 1 to 30 carbon atoms (for example, a linear or branched hydrocarbon group or a cyclic hydrocarbon group, such as an alkanetetrayl group) when n is 2; a hexavalent hydrocarbon group having 2 to 30 carbon atoms (for example, a linear or branched hydrocarbon group or a cyclic hydrocarbon group, such as an alkanehexayl group) when n is 3; and an octavalent hydrocarbon group having 3 to 30 carbon atoms (for example, a linear or branched hydrocarbon group or a cyclic hydrocarbon group, such as an alkaneoctayl group) when n is 4. Here, the above cyclic hydrocarbon group may have a bridged cyclic hydrocarbon group and/or an aromatic group.

Also, the above 2n-valent group $R^1$ (for example, a 2n-valent hydrocarbon group) may have a double bond or may have a heteroatom.

The compound represented by the above formula (1) has high heat resistance attributed to its rigid structure, in spite of its relatively low molecular weight, and can therefore be used even under high temperature baking conditions. Also, the compound represented by the above formula (1) has tertiary carbon or quaternary carbon in the molecule, which suppresses crystallization, and is thus suitably used as a film forming material for lithography.

In addition, the compound represented by the above formula (1) has high solubility in an organic solvent (particularly, a safe solvent) and has excellent heat resistance and etching resistance. For this reason, a film forming material for lithography containing the compound represented by the above formula (1) has excellent resist pattern formability. Examples of the above organic solvent include the organic solvents described in [Solvent] exemplified in the section of [Composition], which will be mentioned later.

Moreover, the compound represented by the above formula (1) has a relatively low molecular weight and a low viscosity, and therefore facilitates enhancing film smoothness while uniformly and completely filling even the steps of an uneven supporting material (particularly having fine space, hole pattern, etc.). As a result, a film forming material for lithography containing the compound represented by the above formula (1) has excellent embedding properties and smoothing properties. In addition, the compound represented by the above formula (1) is a compound that has a relatively high carbon concentration, and can therefore exhibit high etching resistance, as well.

In addition, the compound represented by the above formula (1) has high refractive index ascribable to its high aromatic ring density and is prevented from being stained by heat treatment in a wide range from a low temperature to a high temperature. Therefore, the compound represented by the formula (1) is also useful as various optical component forming materials. The compound represented by the above formula (1) preferably has quaternary carbon from the viewpoint of preventing the compound from being oxidatively decomposed and stained and improving heat resistance and solvent solubility.

The above optical component may be in the form of a film or a sheet, and examples thereof include a plastic lens (for example, a prism lens, a lenticular lens, a microlens, a Fresnel lens, a viewing angle control lens, a contrast improving lens, etc.), a phase difference film, a film for electromagnetic wave shielding, a prism, an optical fiber, a solder resist for flexible printed wiring, a plating resist, an interlayer insulating film for multilayer printed circuit boards, a photosensitive optical waveguide, a liquid crystal display, an organic electroluminescent (EL) display, an optical semiconductor (LED) element, a solid state image sensing element, an organic thin film solar cell, a dye sensitized solar cell, and an organic thin film transistor (TFT). The compound represented by the formula (1) is suitably used as a material for forming an embedded film and a smoothed film on a photodiode, a smoothed film in front of or behind a color filter, a microlens, and a smoothed film and a conformal film on a microlens, all of which are members of a solid state image sensing element, to which high refractive index is demanded.

In the compound represented by the above formula (1), it is preferable that at least one $R^2$ and/or at least one $R^3$ be a hydroxy group and/or a thiol group from the viewpoint of easy crosslinking reaction and solubility in an organic solvent. Also, it is more preferable that at least one $R^2$, at least one $R^3$, at least one $R^4$, and at least one $R^5$ be a hydroxyl group and/or a thiol group (preferably a hydroxyl group).

The compound represented by the above formula (1) is preferably a compound represented by the following formula (1-1) from the viewpoint of easy crosslinking and solubility in an organic solvent.

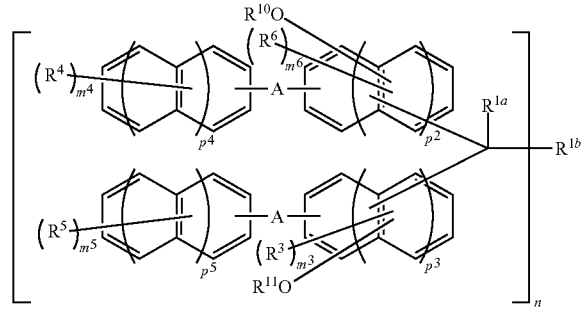

(1-1)

In the above formula (1-1), A, $R^4$, $R^5$, n, $p^2$ to $p^5$, $m^4$ and $m^5$, and n are each as defined in the formula (1); $R^{1a}$ is a hydrogen atom or a monovalent group having 1 to 10 carbon atoms; $R^{1b}$ is an n-valent group having 1 to 25 carbon atoms; $R^6$ and $R^7$ are a monovalent group selected from the group consisting of a linear, branched, or cyclic alkyl group having 1 to 10 carbon atoms, an aryl group having 6 to 10 carbon atoms, an alkenyl group having 2 to 10 carbon atoms, an alkynyl group having 2 to 10 carbon atoms, a thiol group, and a hydroxyl group; $R^{10}$ and $R^{11}$ are a hydrogen atom; and $m^6$ and $m^7$ are each independently an integer of 0 to 7.

Examples of the monovalent group $R^{1a}$ having 1 to 10 carbon atoms include a linear, branched or cyclic alkyl group and an aryl group; and specific examples thereof include a methyl group, an ethyl group, a n-propyl group, an i-propyl group, a n-butyl group, an i-butyl group, a t-butyl group, a n-pentyl group, a neopentyl group, a cyclopentyl group, a n-hexyl group, a cyclohexyl group, and a phenyl group.

Examples of the n-valent group $R^{1b}$ having 1 to 25 carbon atoms include a monovalent hydrocarbon group having 1 to 25 carbon atoms (for example, a linear or branched hydrocarbon group or a cyclic hydrocarbon group, such as an alkyl group) when n is 1; a divalent hydrocarbon group having 1 to 25 carbon atoms (for example, a linear or branched hydrocarbon group or a cyclic hydrocarbon group, such as an alkylene group) when n is 2; a trivalent hydrocarbon group having 1 to 25 carbon atoms (for example, a linear or branched hydrocarbon group or a cyclic hydrocarbon group, such as an alkanetriyl group) when n is 3; and a tetravalent hydrocarbon group having 1 to 25 carbon atoms (for example, a linear or branched hydrocarbon group or a cyclic hydrocarbon group, such as an alkanetetrayl group) when n is 4. Here, the above cyclic hydrocarbon group may have a bridged cyclic hydrocarbon group and/or an aromatic group. The group $R^{1b}$ may have a double bond or may have a heteroatom.

In addition, the compound represented by the above formula (1-1) is preferably a compound represented by the following formula (1-2) from the viewpoint of easy crosslinking and solubility in an organic solvent.

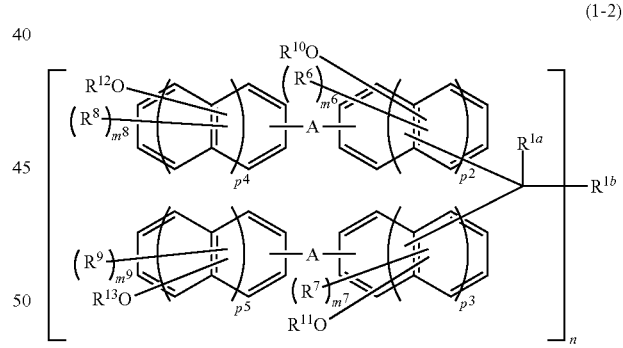

(1-2)

In the above formula (1-2), A, $R^{1a}$, $R^{1b}$, $R^6$, $R^7$, $R^{10}$, $R^{11}$, n, $p^2$ to $p^5$, $m^6$ and $m^7$ are each as defined in the formula (1-1): $R^8$ and $R^9$ are a monovalent group selected from the group consisting of a linear, branched, or cyclic alkyl group having 1 to 10 carbon atoms, an aryl group having 6 to 10 carbon atoms, an alkenyl group having 2 to 10 carbon atoms, an alkynyl group having 2 to 10 carbon atoms, a thiol group, and a hydroxyl group; $R^{12}$ and $R^{13}$ are a hydrogen atom; and $m^8$ and $m^9$ are each independently an integer of 0 to 8.

In addition, the compound represented by the above formula (1) is preferably a compound represented by the following formula (1a) from the viewpoint of the supply of raw materials.

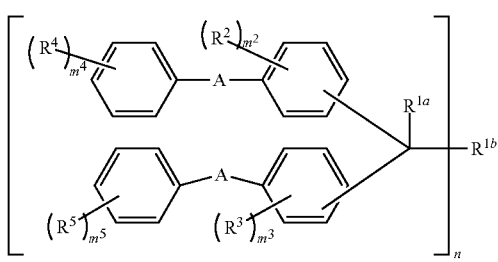

(1a)

In the above formula (1a), A, $R^2$ to $R^5$ and n are each as defined in the above formula (1); $R^{1a}$ is a hydrogen atom or a monovalent group having 1 to 10 carbon atoms; $R^{1b}$ is an n-valent group having 1 to 25 carbon atoms; $m^2$ and $m^3$ are each independently an integer of 0 to 4; and $m^4$ and $m^5$ are each independently an integer of 0 to 5. The monovalent group $R^{1a}$ having 1 to 10 carbon atoms is as described in the above formula (1-1). The n-valent group $R^{1b}$ having 1 to 25 carbon atoms is as described in the above formula (1-1).

The compound represented by the above formula (1a) is more preferably a compound represented by the following formula (1b) from the viewpoint of solubility in an organic solvent.

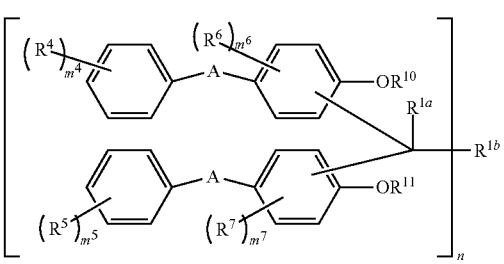

(1b)

In the above formula (1b), A, $R^4$, $R^5$, $R^{1a}$, $R^{1b}$, $m^4$, $m^5$, and n are each as defined in the above formula (1a); $R^6$ and $R^7$ are each independently a linear, branched, or cyclic alkyl group having 1 to 10 carbon atoms, an aryl group having 6 to 10 carbon atoms, an alkenyl group having 2 to 10 carbon atoms, an alkynyl group having 2 to 10 carbon atoms, a thiol group, or a hydroxyl group; $m^6$ and $m^7$ are each independently an integer of 0 to 3; and $R^{10}$ and $R^{11}$ are a hydrogen atom.

The compound represented by the above formula (1b) is further preferably a compound represented by the following formula (1c) from the viewpoint of solubility in an organic solvent.

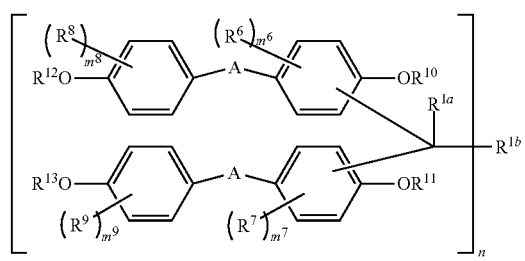

(1c)

In the above formula (1c), A, $R^{1a}$, $R^{1b}$, $R^6$, $R^7$, $R^{10}$, $R^{11}$, $m^6$, $m^7$, and n are each as defined in the above formula (1b); $R^8$ and $R^9$ are each independently a linear, branched, or cyclic alkyl group having 1 to 10 carbon atoms, an aryl group having 6 to 10 carbon atoms, an alkenyl group having 2 to 10 carbon atoms, an alkynyl group having 2 to 10 carbon atoms, a thiol group, or a hydroxyl group; $m^8$ and $m^9$ are each independently an integer of 0 to 4; and $R^{12}$ and $R^{13}$ are a hydrogen atom.

The compound represented by the above formula (1c) is particularly preferably a compound represented by any of the following formulas (BisF-1) to (BisF-3) and (BiF-1) to (BiF-7) from the viewpoint of further solubility in an organic solvent.

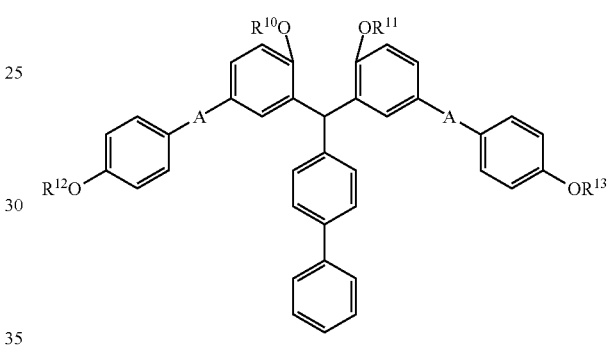

(BisF-1)

In the above (BisF-1), A and $R^{10}$ to $R^{13}$ are each as defined in the above formula (1c).

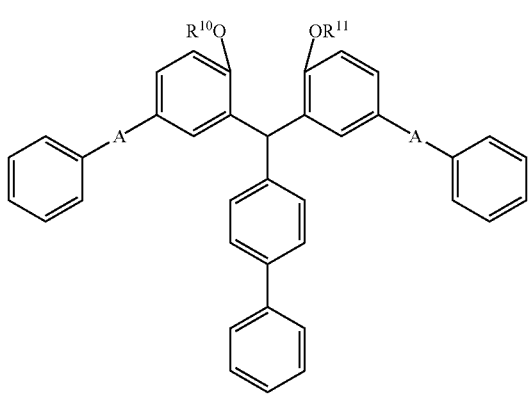

(BisF-2)

In the above (BisF-2), A, $R^{10}$, and $R^{11}$ are each as defined in the above formula (1c).

(BisF-3)

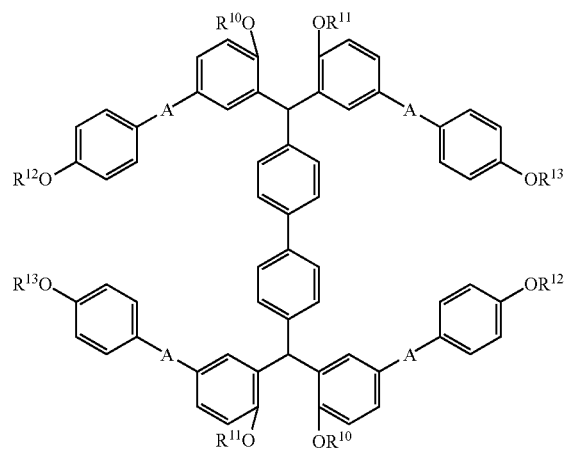

In the above (BisF-3), A and $R^{10}$ to $R^{13}$ are each as defined in the above formula (1c).

(BiF-3)

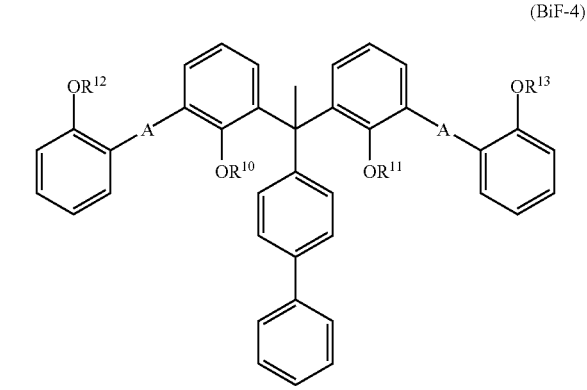

In the above (BiF-3), A and $R^{10}$ to $R^{13}$ are each as defined in the above formula (1c).

(BiF-1)

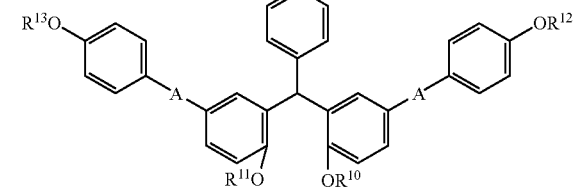

In the above (BiF-1), A and $R^{10}$ to $R^{13}$ are each as defined in the above formula (1c).

(BiF-4)

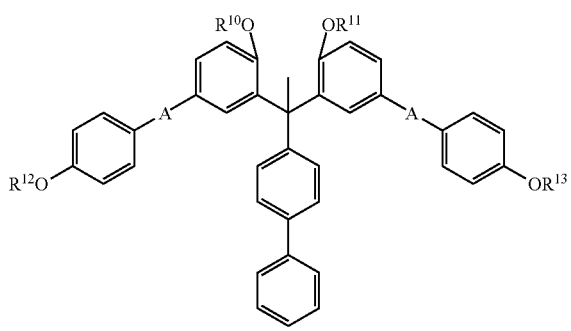

In the above (BiF-4), A and $R^{10}$ to $R^{13}$ are each as defined in the above formula (1c).

(BiF-2)

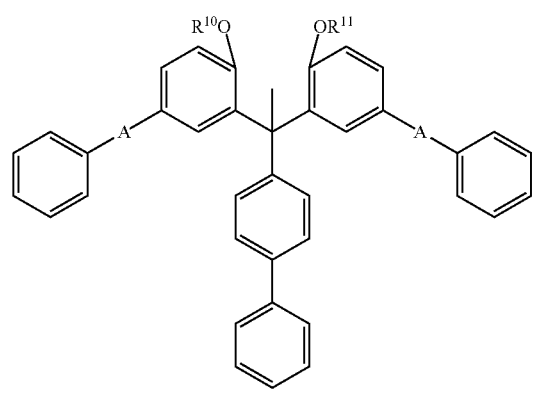

In the above (BiF-2), A, $R^{10}$, and $R^{11}$ are each as defined in the above formula (1c).

(BiF-5)

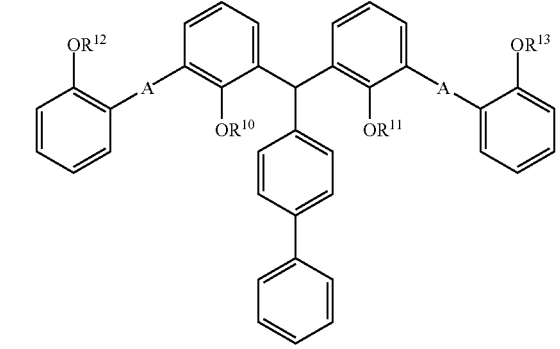

In the above (BiF-5), A and $R^{10}$ to $R^{13}$ are each as defined in the above formula (1c).

(BiF-6)
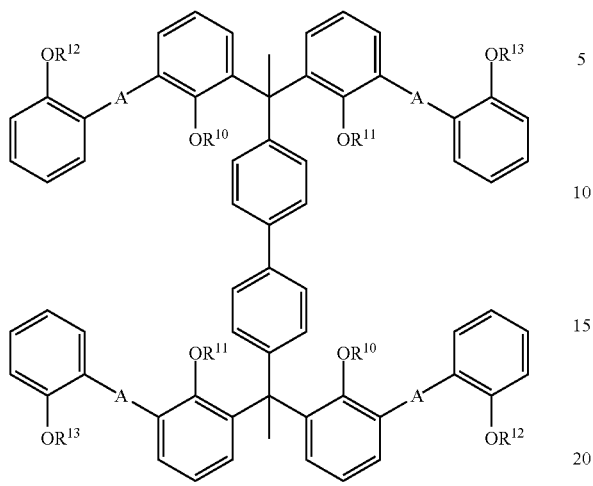
In the above (BiF-6), A and $R^{10}$ to $R^{13}$ are each as defined in the above formula (1c).
(BiF-7)
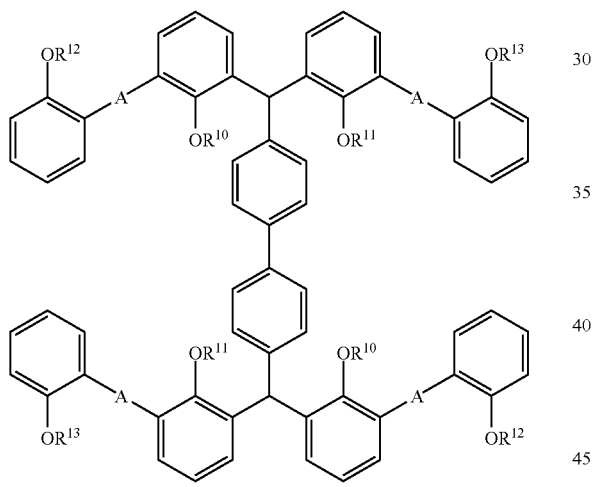
In the above (BiF-7), A and $R^{10}$ to $R^{13}$ are each as defined in the above formula (1c).
The compound represented by the formula (1) is preferably a compound selected from the group represented by the following formulas from the viewpoint of heat resistance and solubility in an organic solvent.
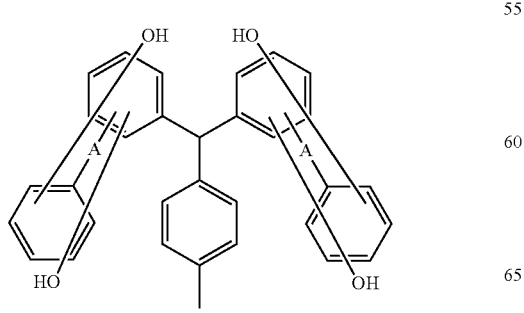
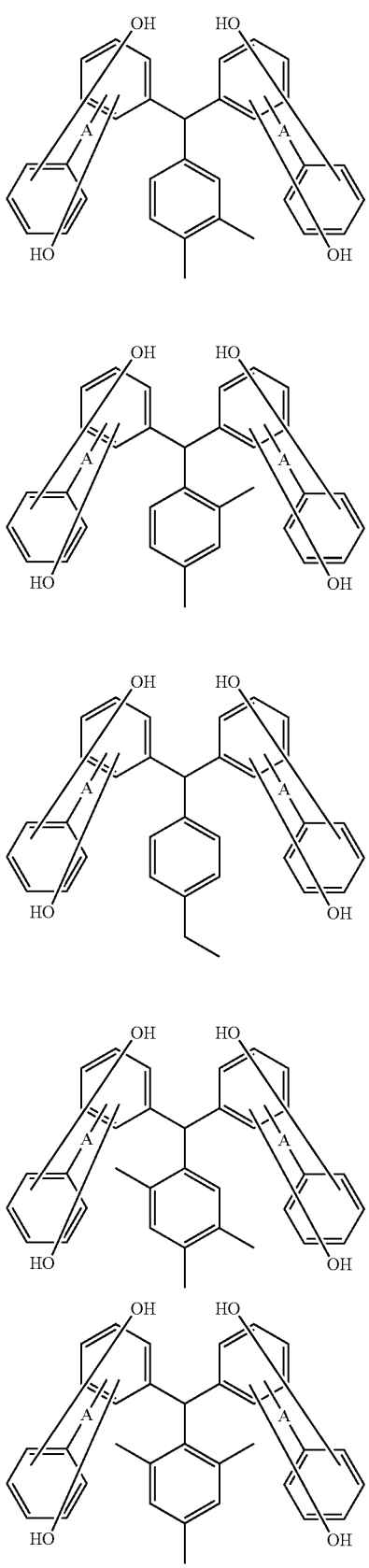

-continued
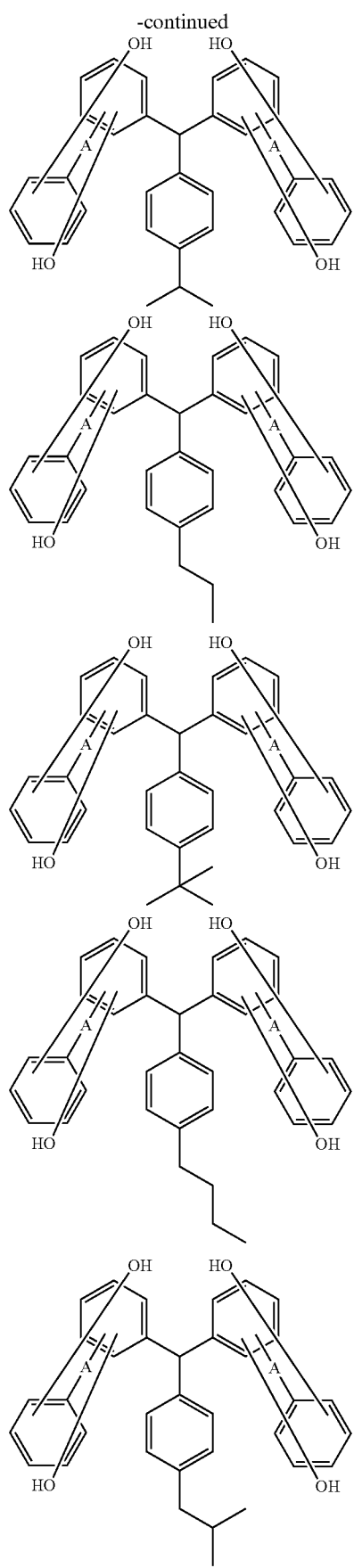
-continued
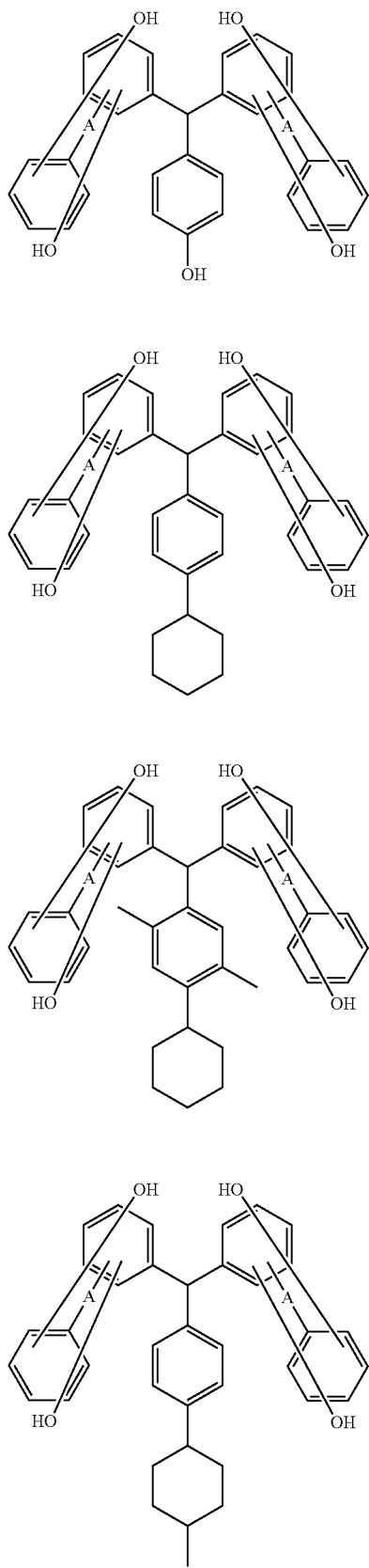

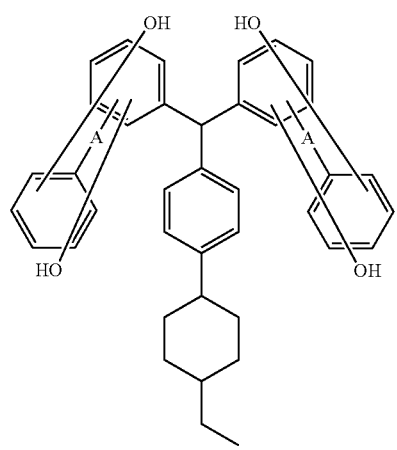
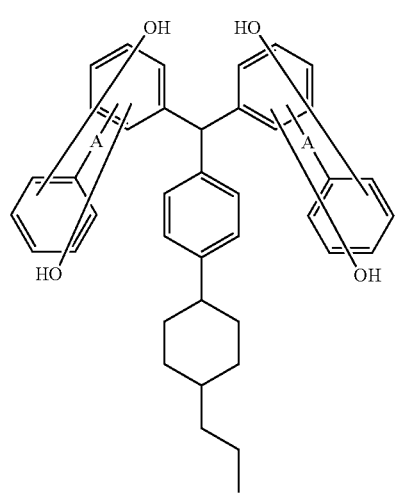
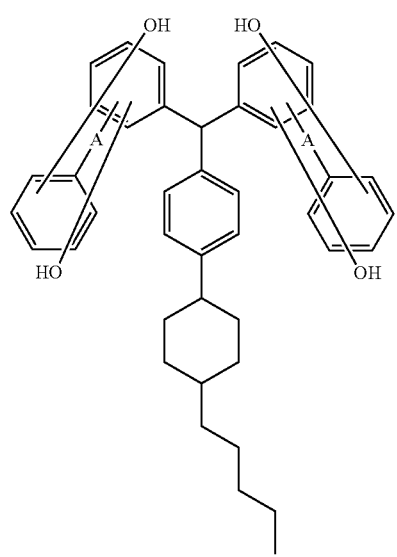
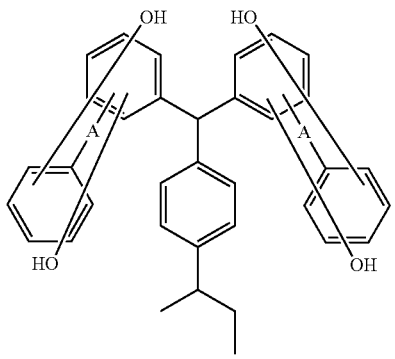
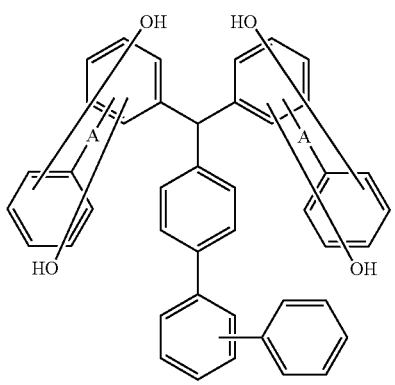
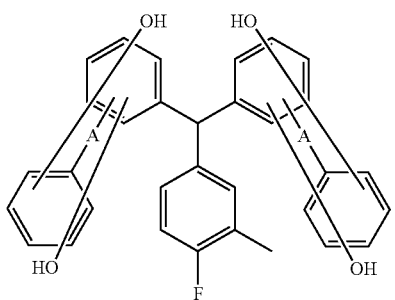
In each of the above formulas, A is as defined in the above formula (1).
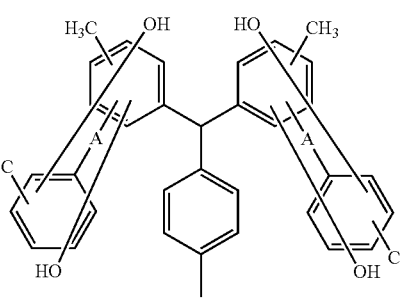

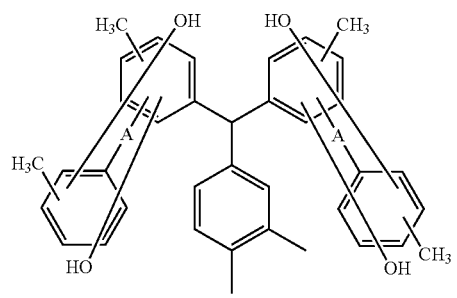
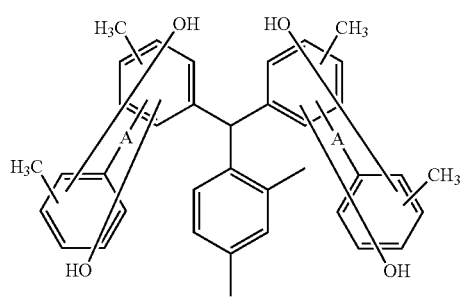
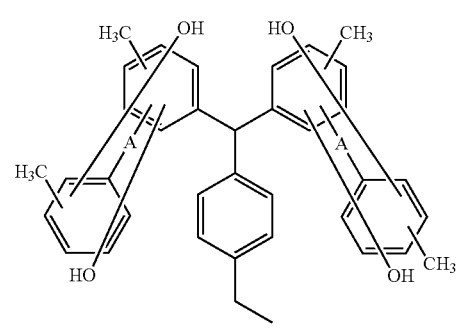
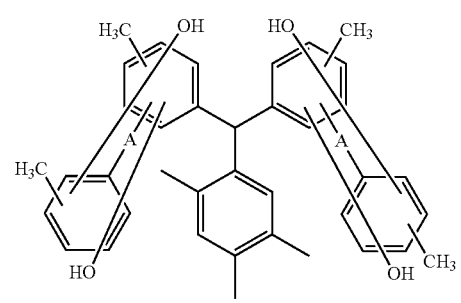
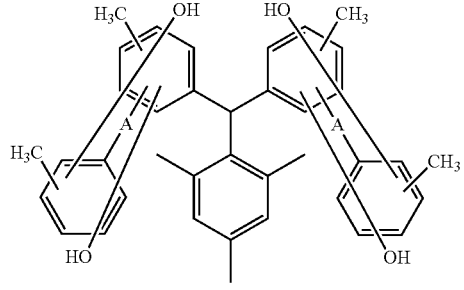
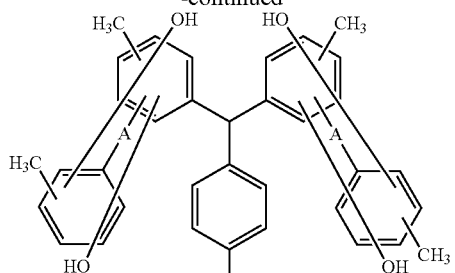
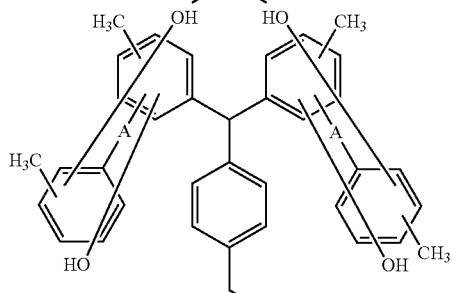
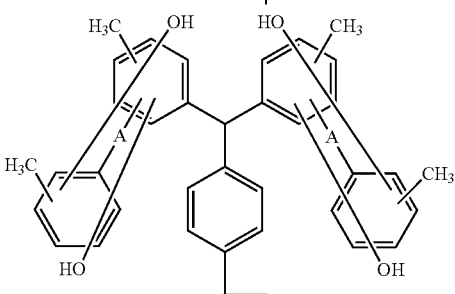
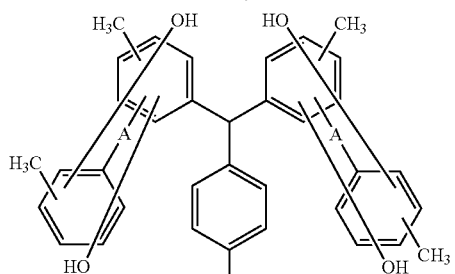
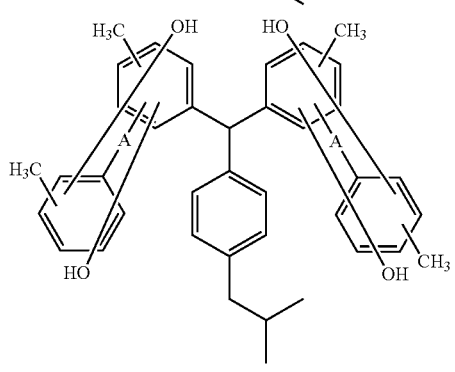

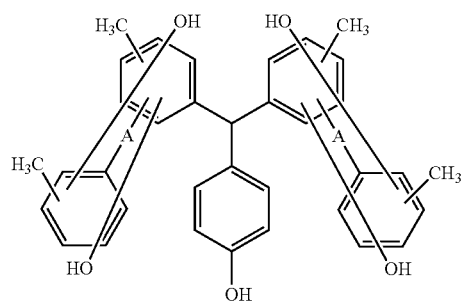
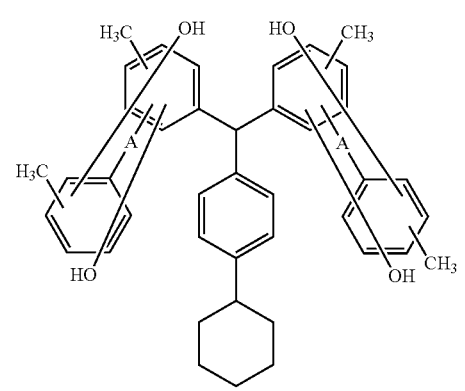
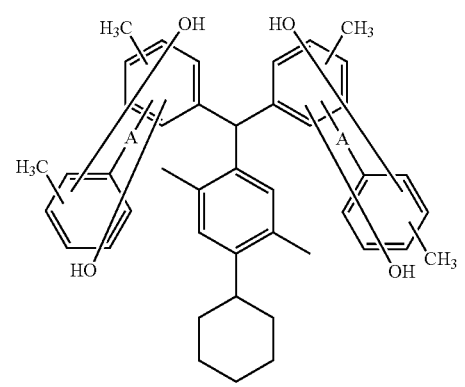
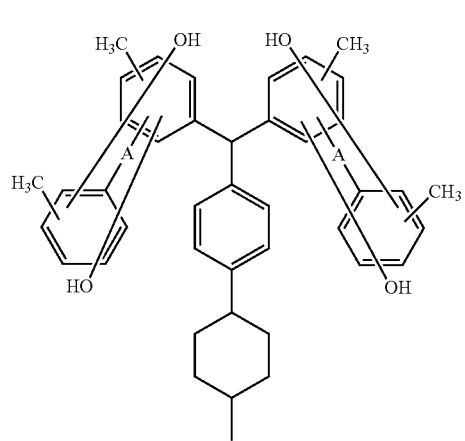
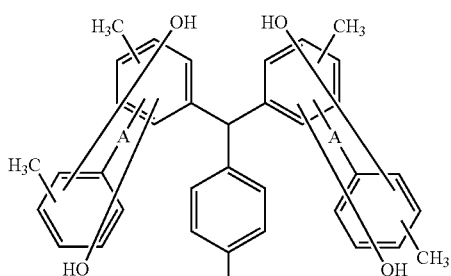
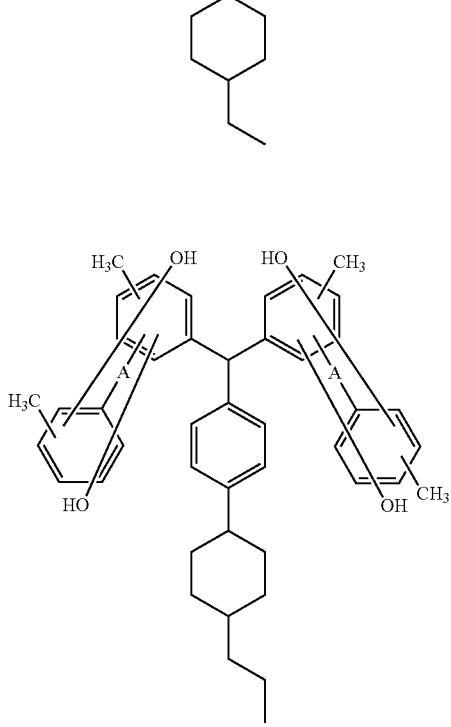
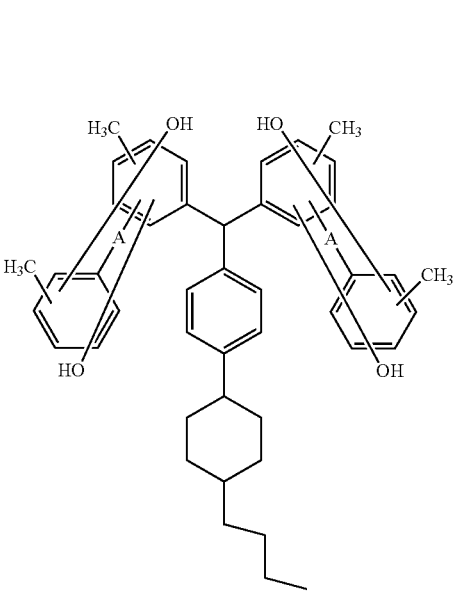

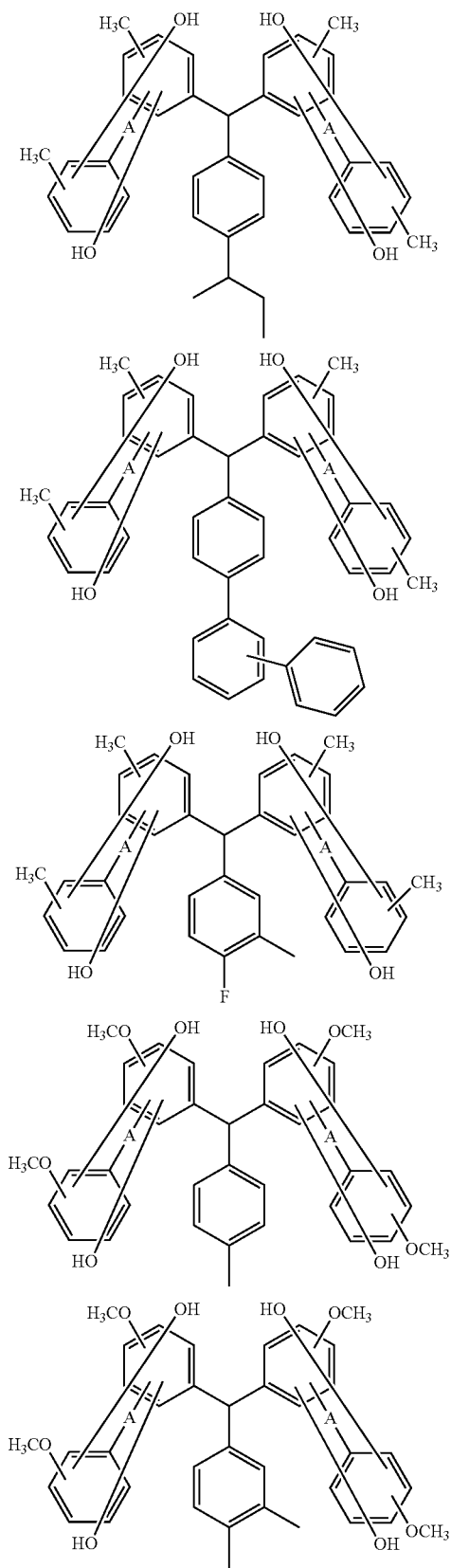
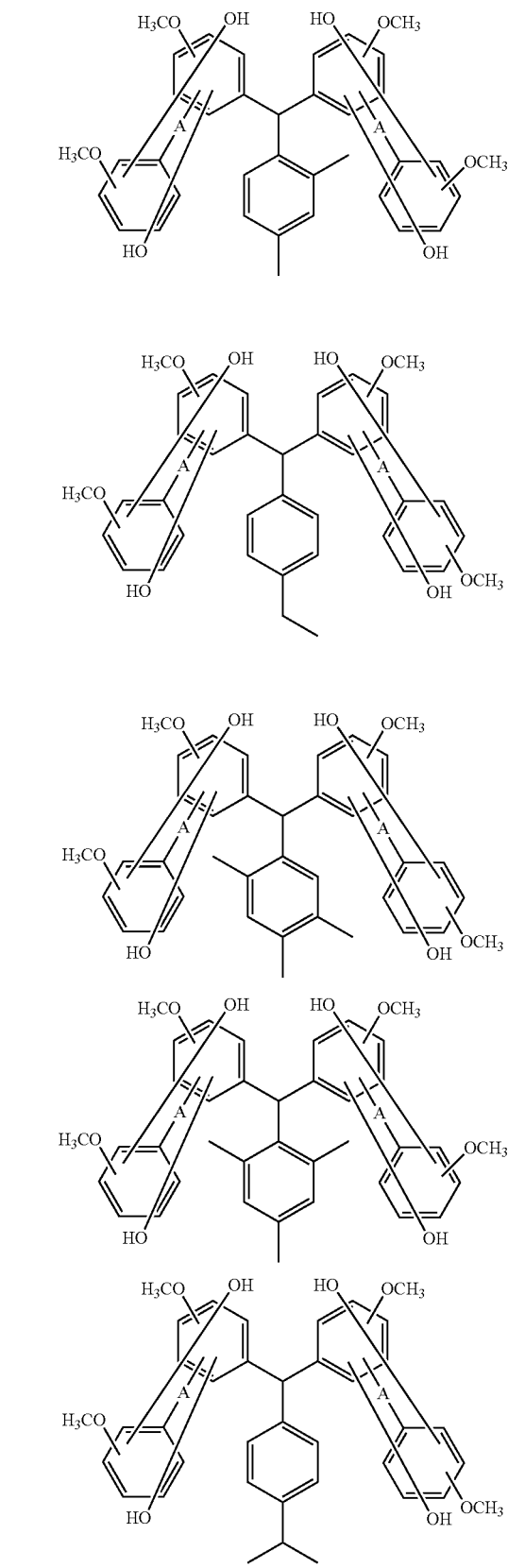

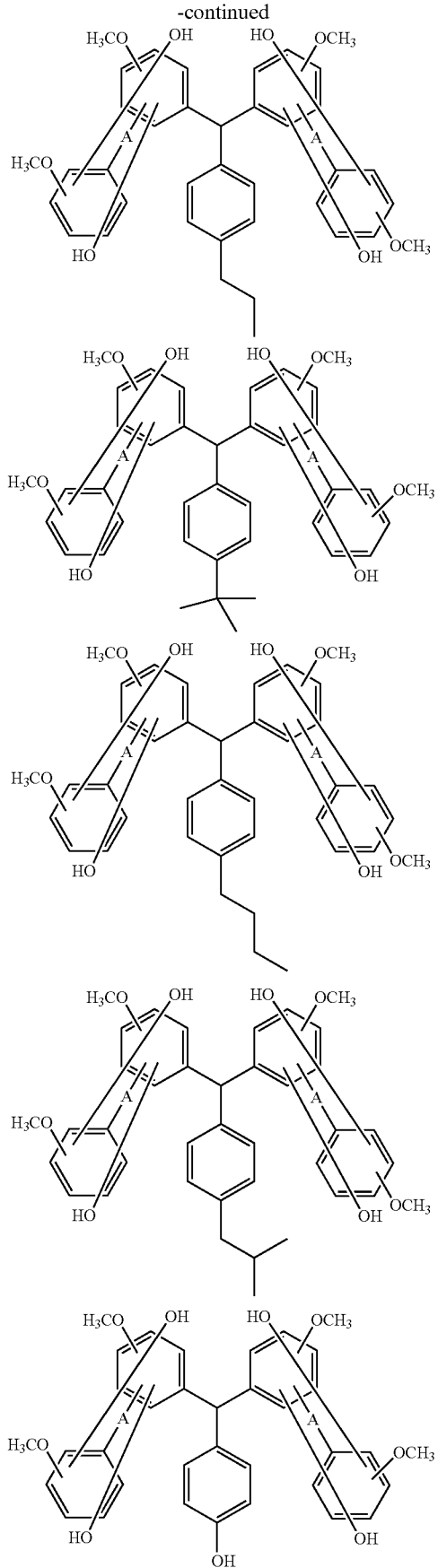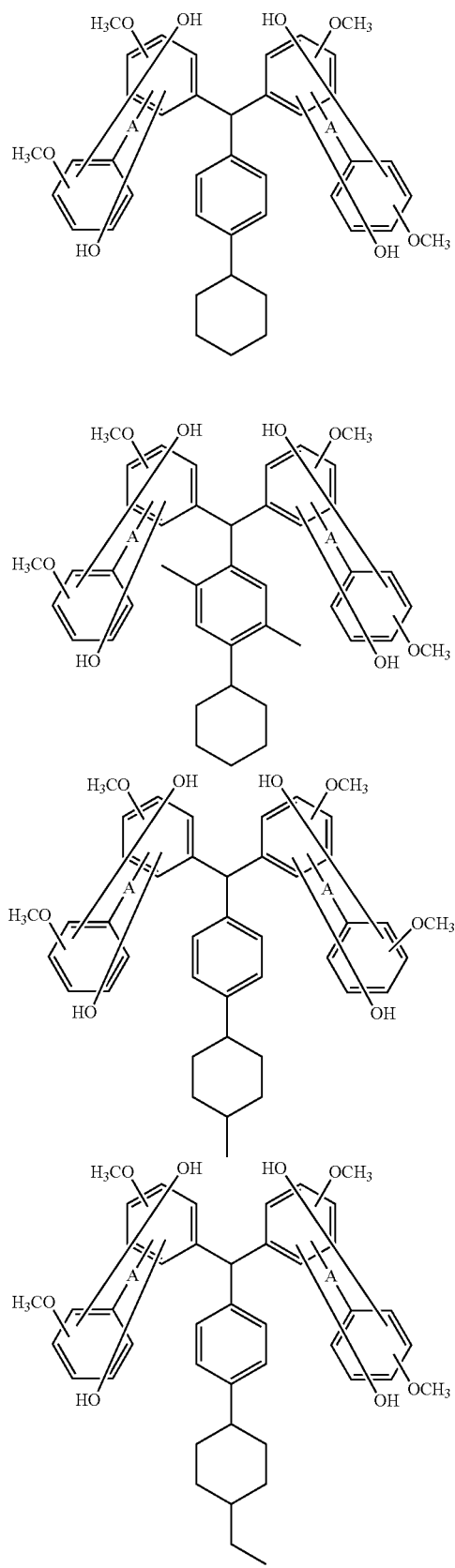

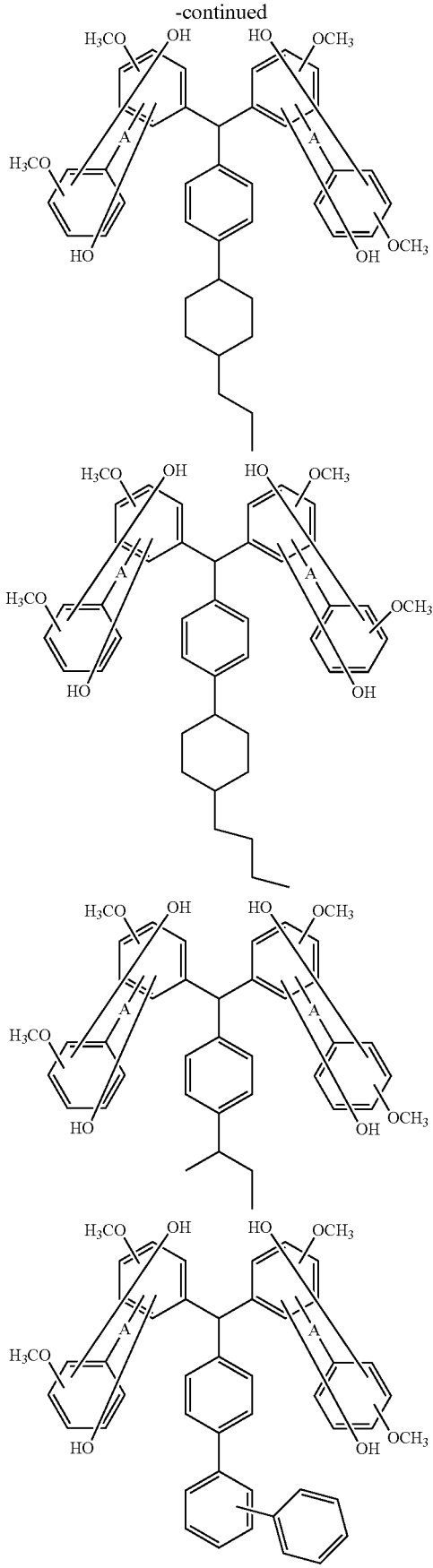
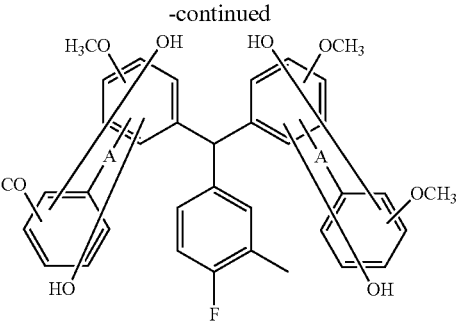
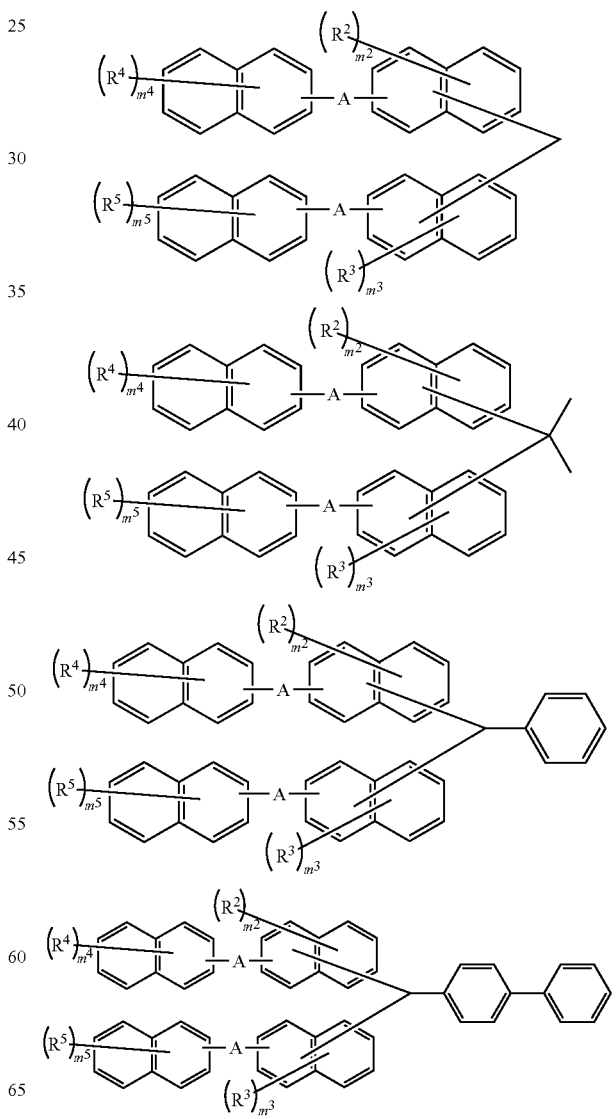
In each of the above formulas, A is as defined in A in the above formula (1).
Specific examples of the compound represented by the above formula (1) include compounds represented by the following formulas. However, the compound represented by the above formula (1) is not limited to the compounds represented by the following formulas.

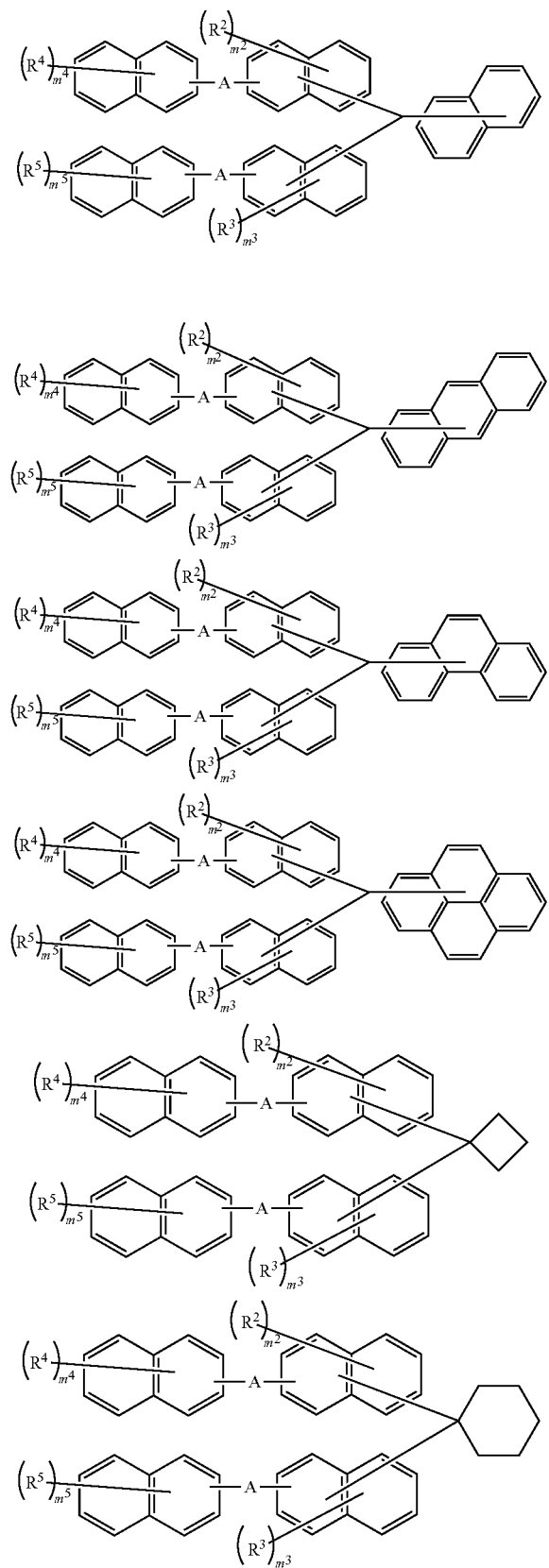
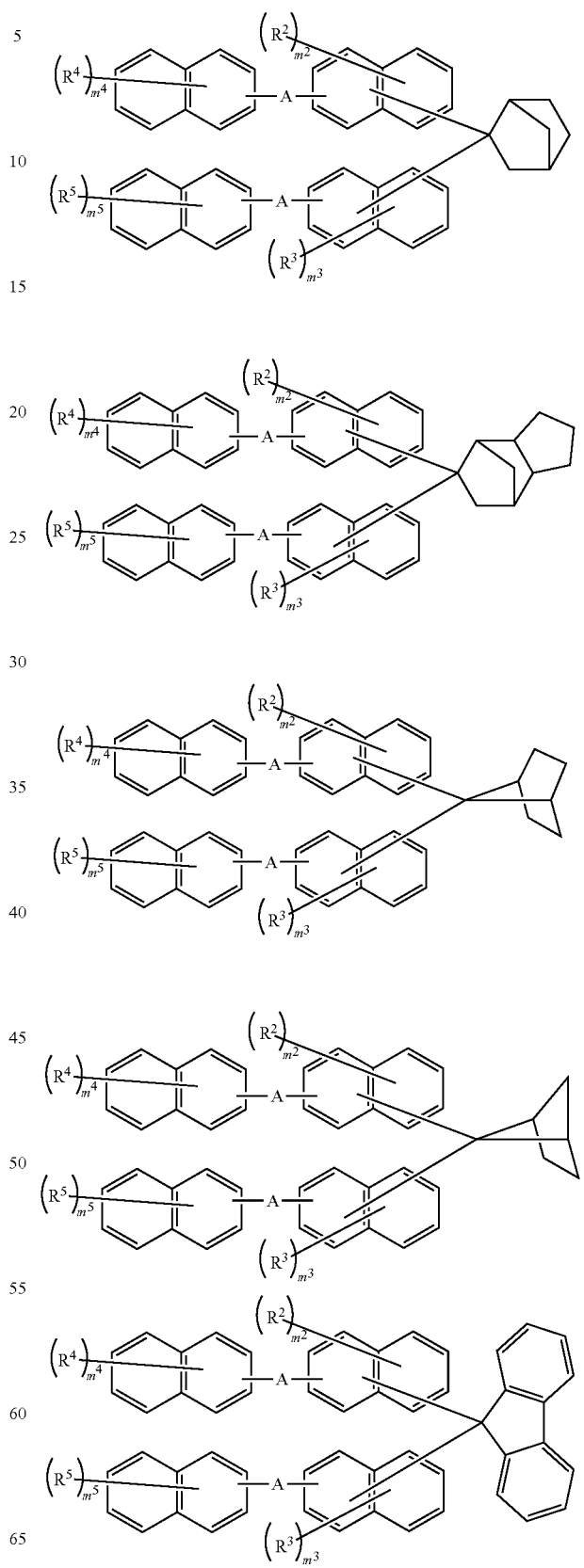

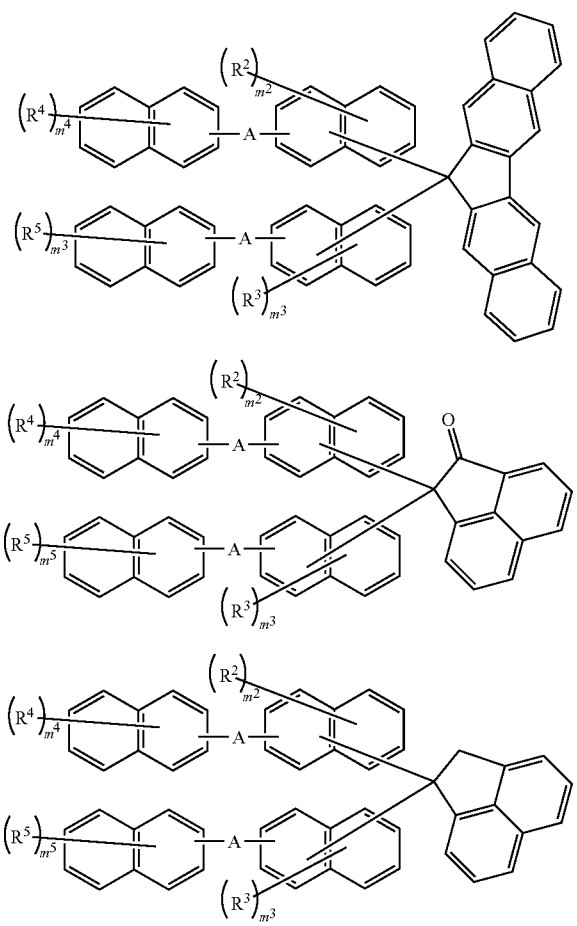
In each of the above formulas, A, $R^2$ to $R^5$, and $m^2$ to $m^5$ are each as defined in the above formula (1).
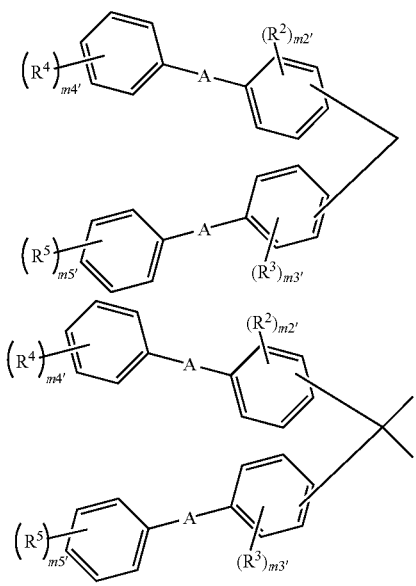
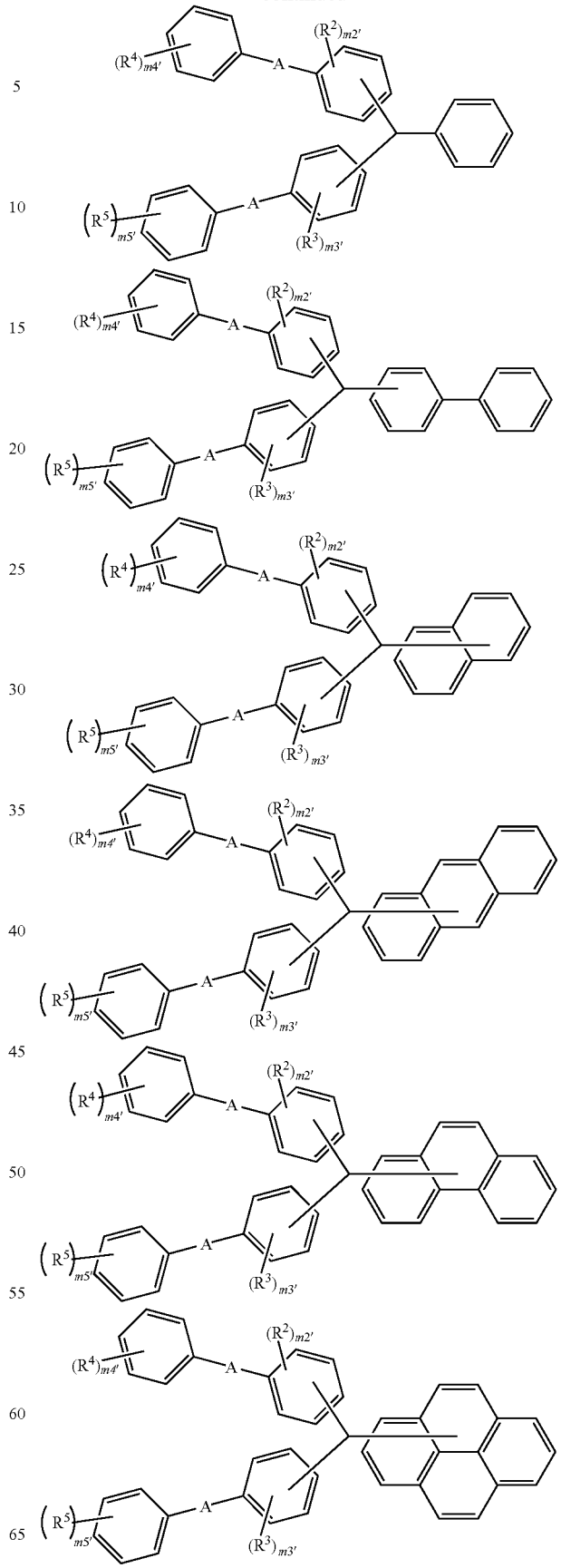

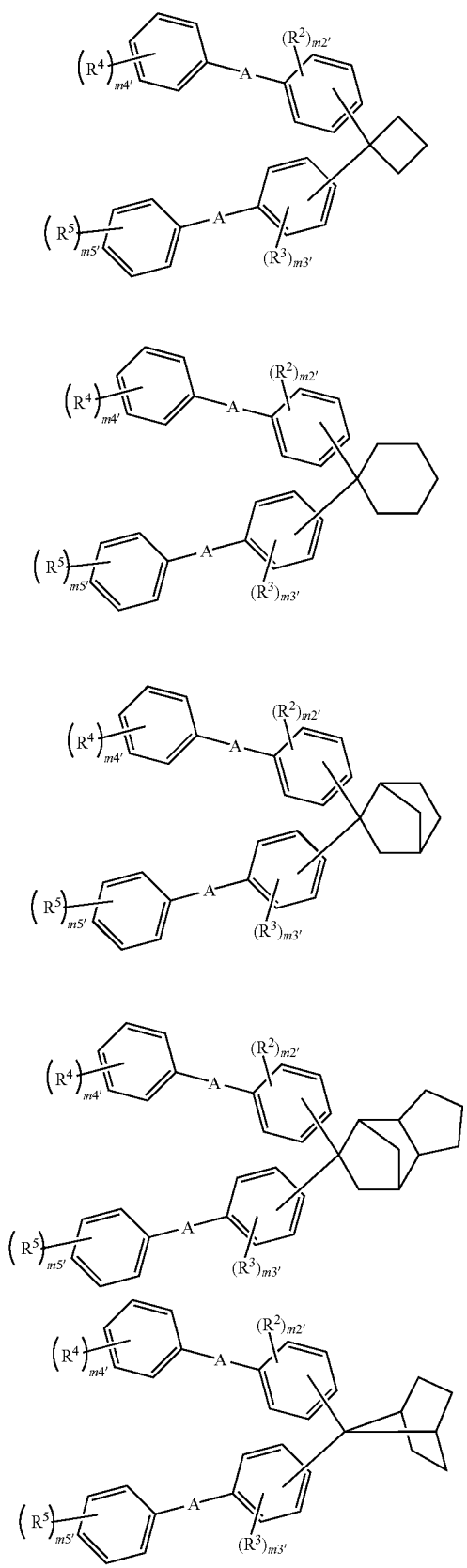
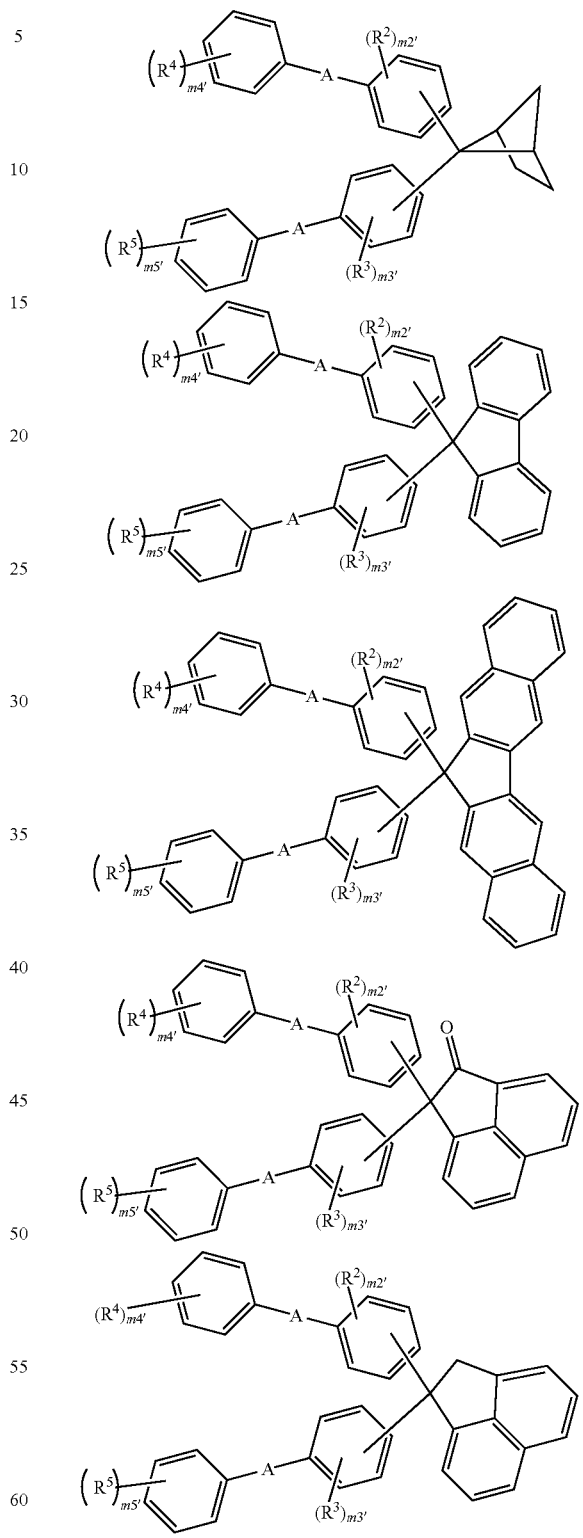
In each of the above formulas, A and $R^2$ to $R^5$ are each as defined in the above formula (1). $m^{2'}$ and $m^{3'}$ are each independently an integer of 0 to 4, and $m^{4'}$ and $m^{5'}$ are each independently an integer of 0 to 5.

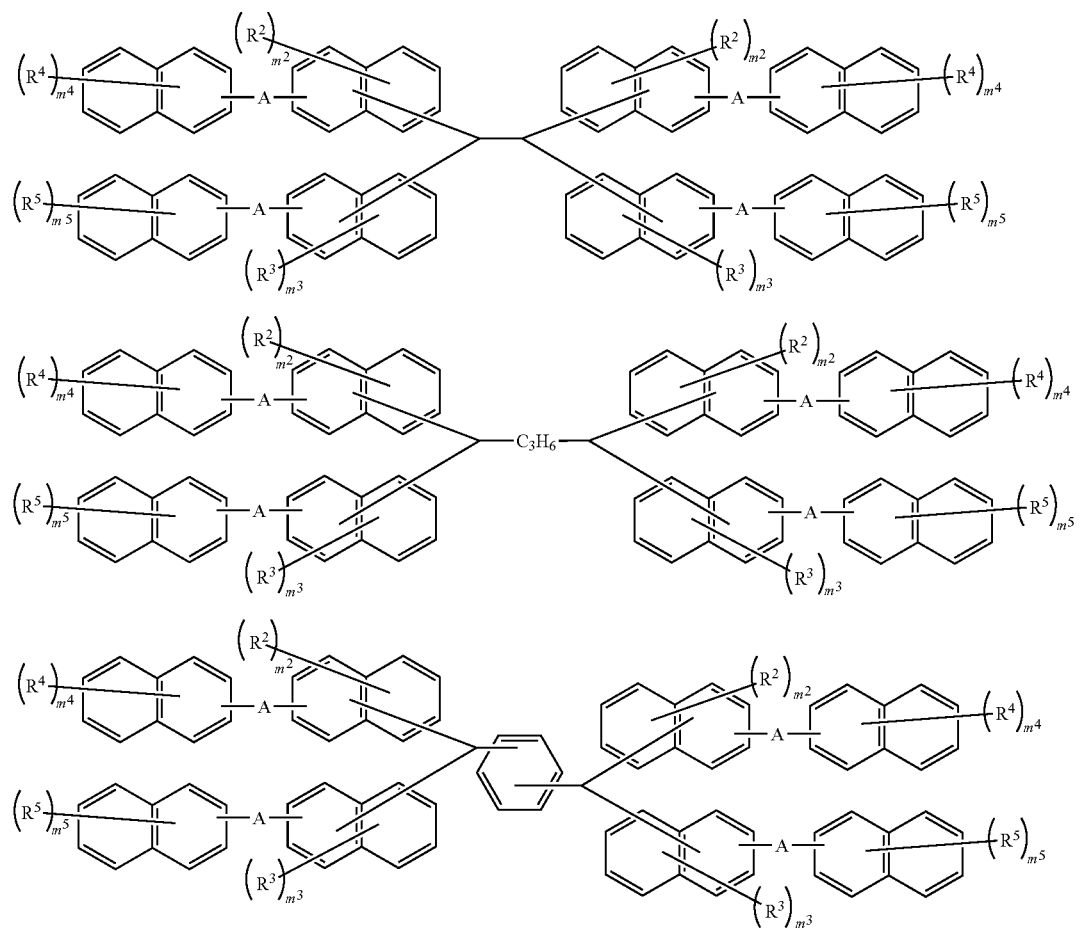
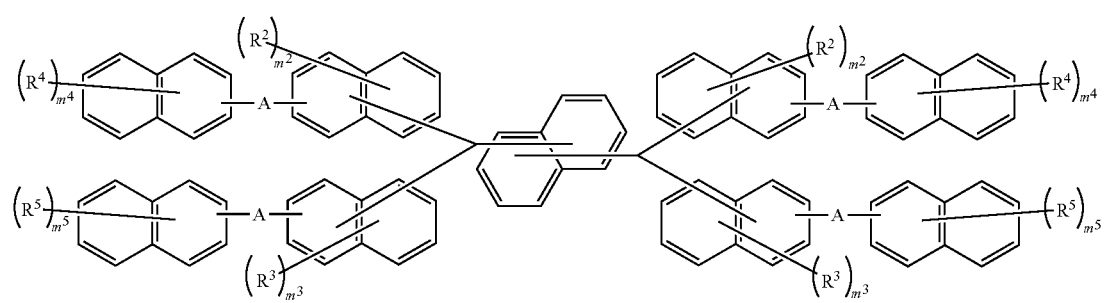
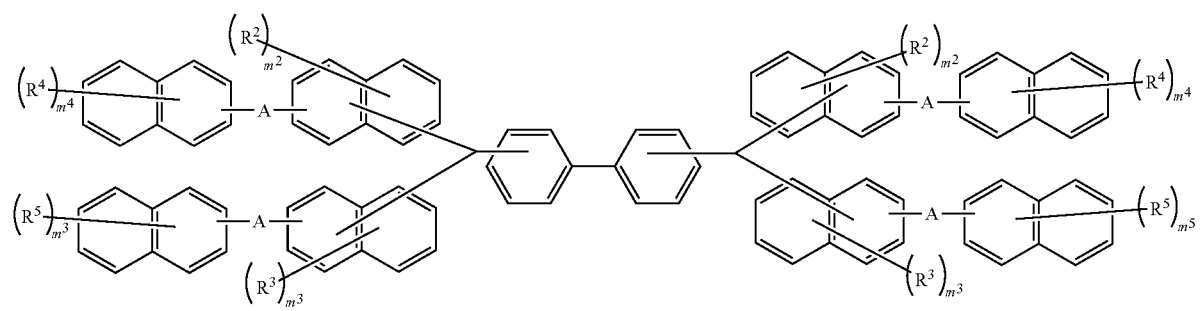

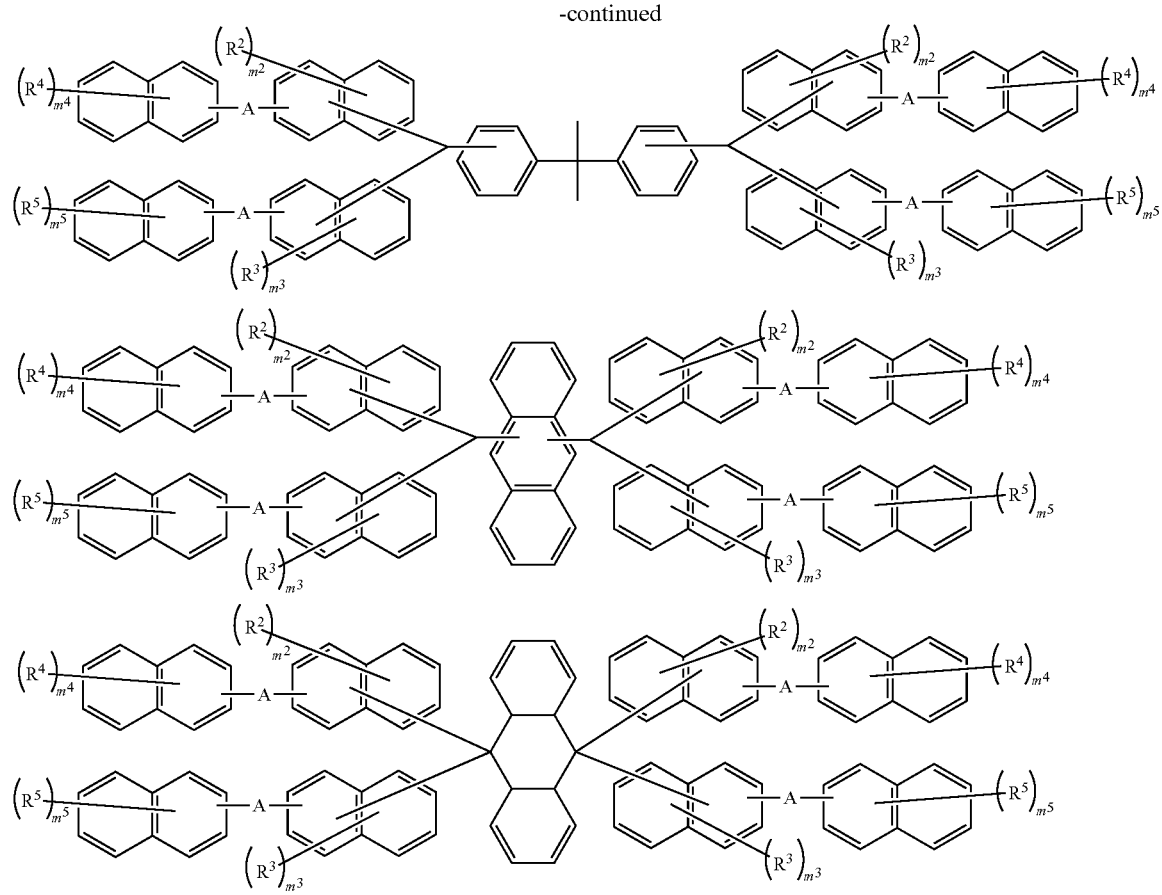
In each of the above formulas, A, $R^2$ to $R^5$, and $m^2$ to $m^5$ are each as defined in the above formula (1).
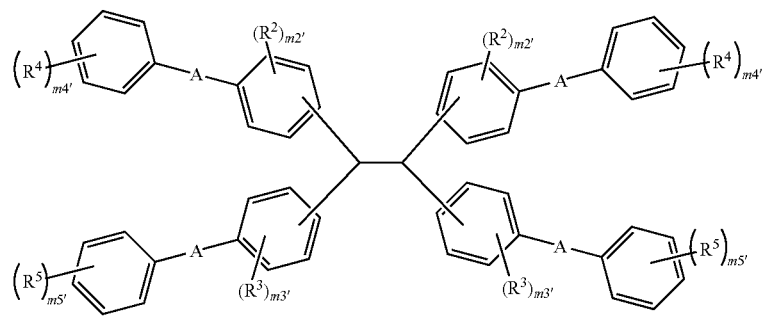
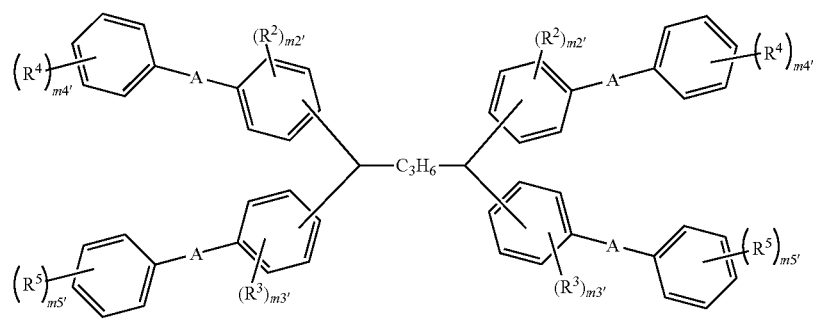

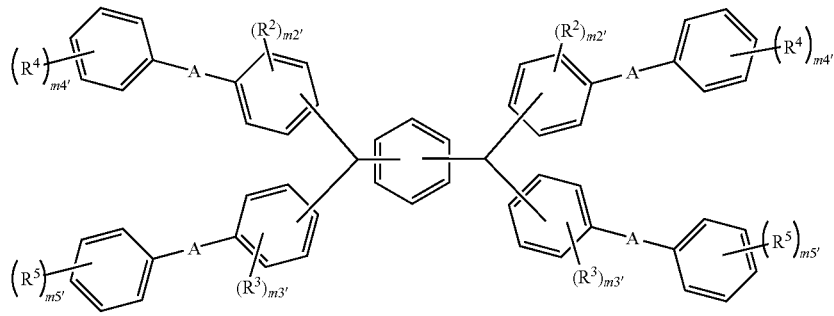
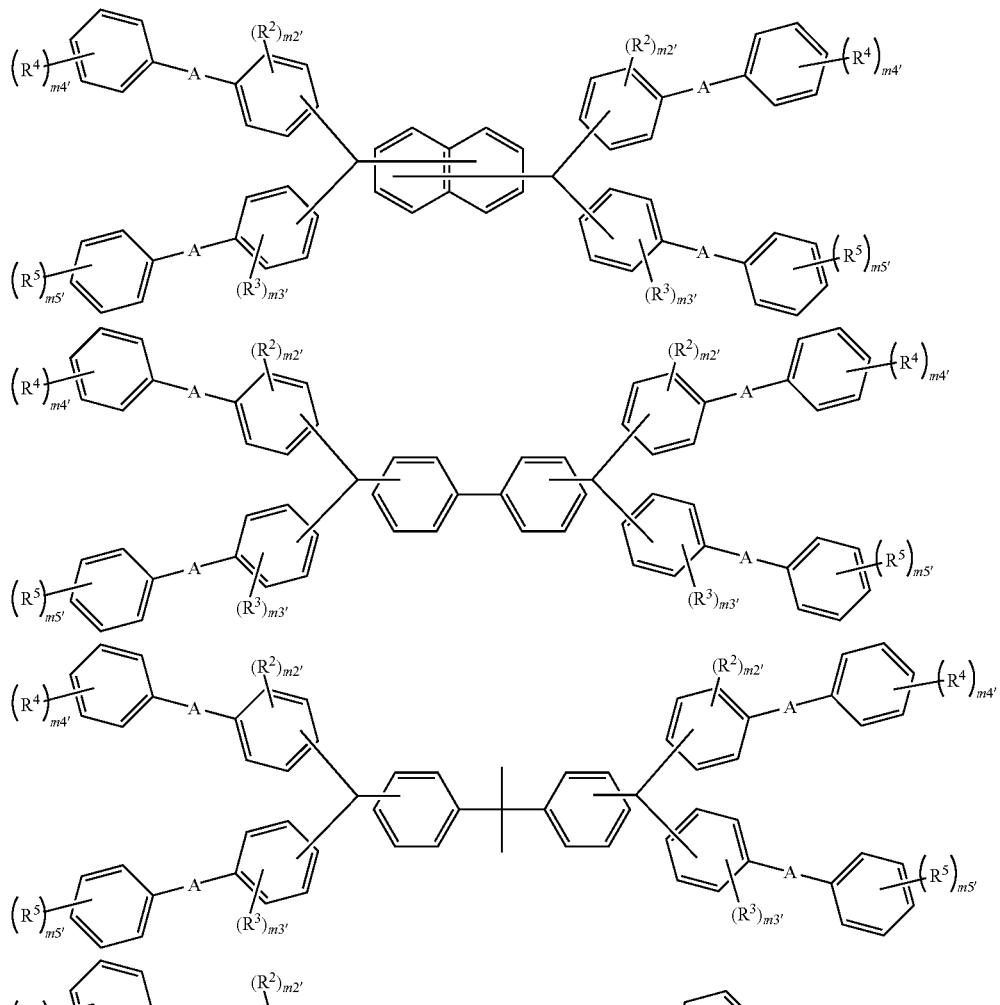
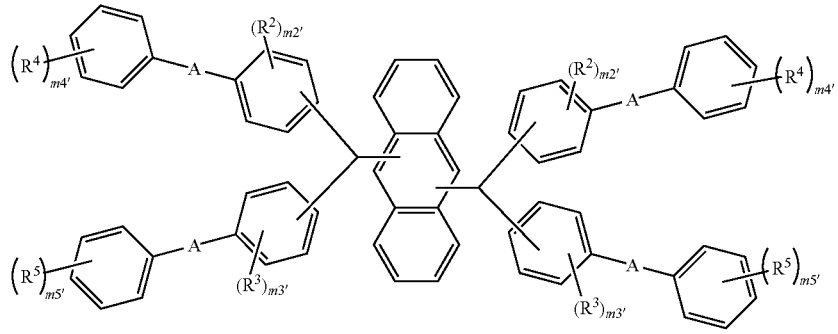

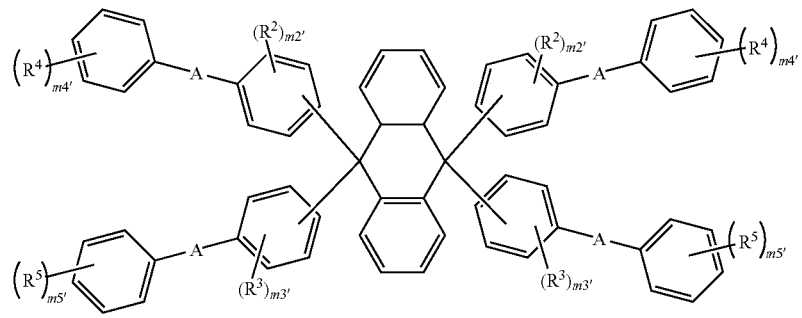
In each of the above formulas, A and $R^2$ to $R^5$ are each as defined in the above formula (1). $m^{2'}$ and $m^{3'}$ are each independently an integer of 0 to 4, and $m^{4'}$ and $m^{5'}$ are each independently an integer of 0 to 5.
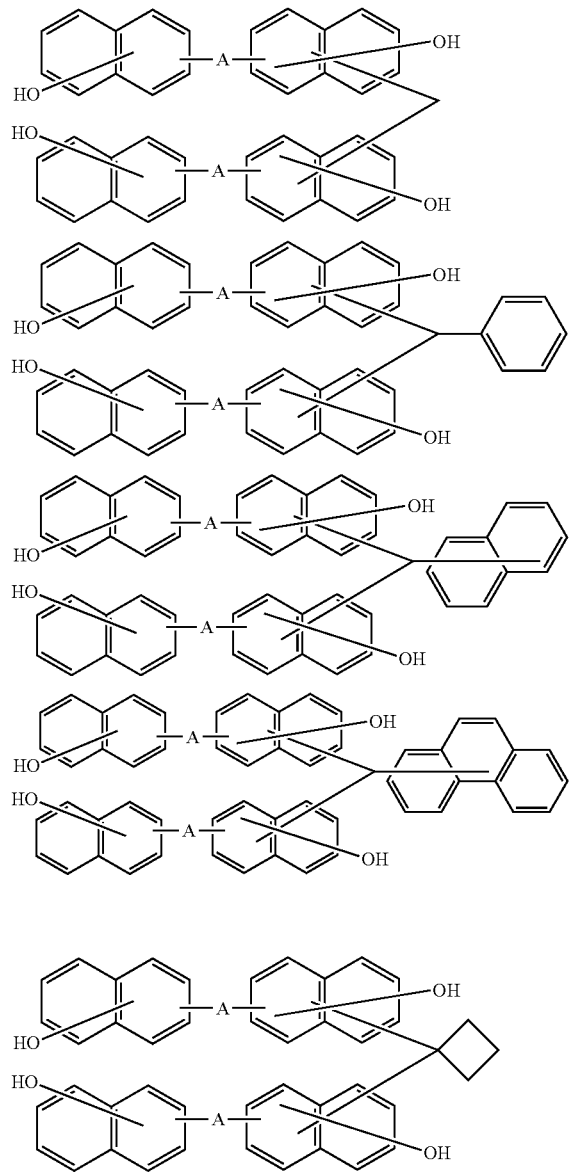
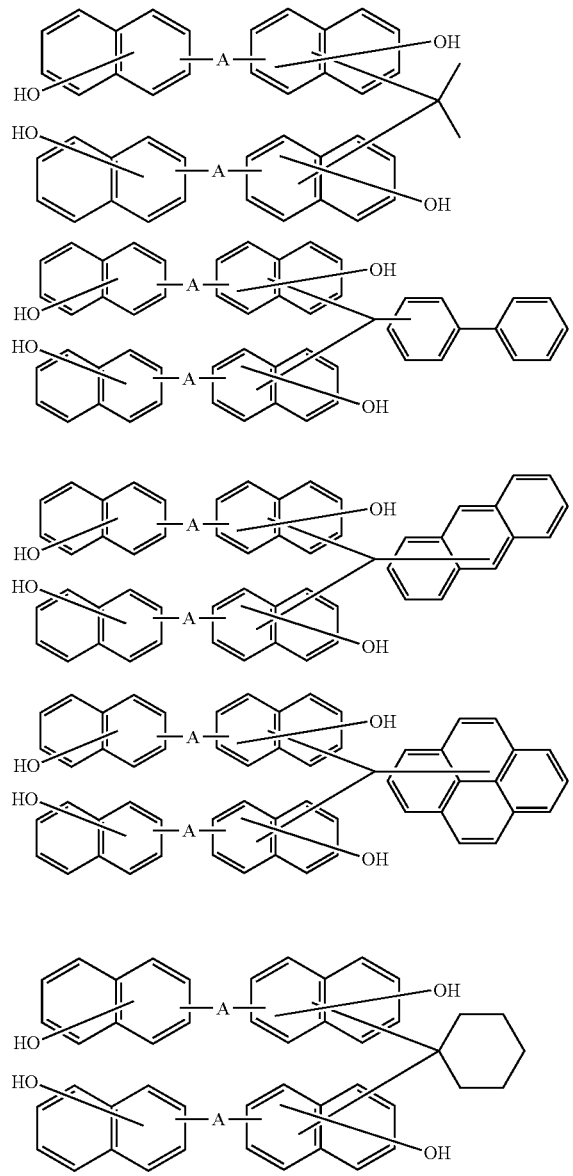

-continued
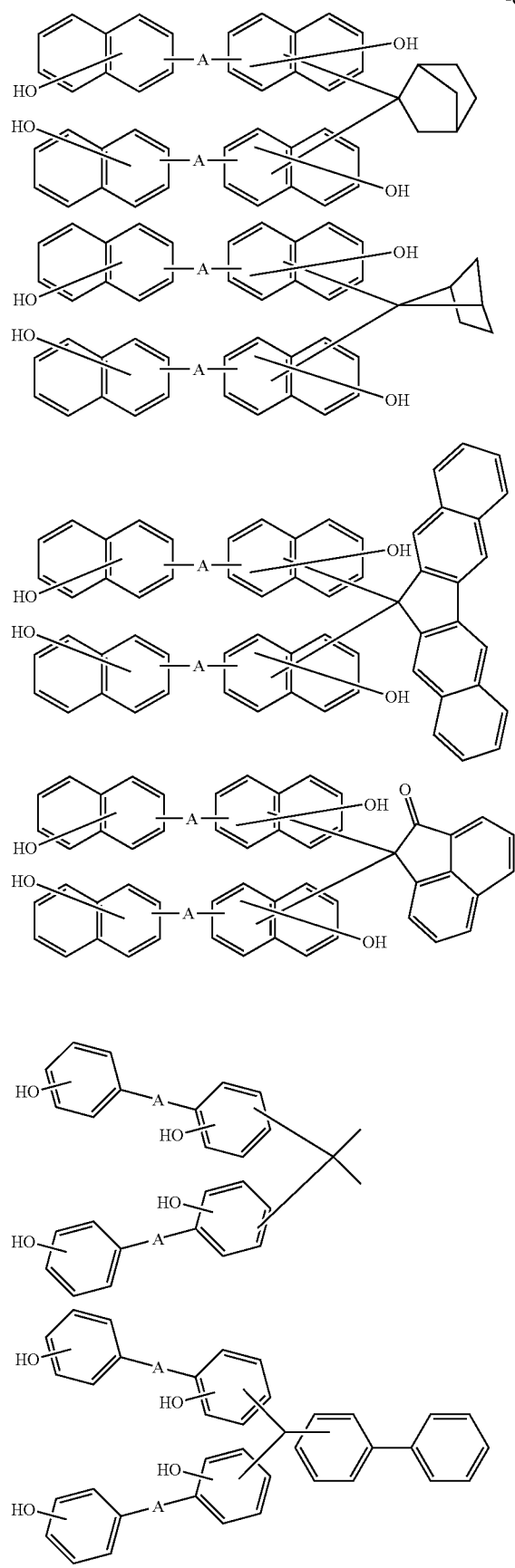
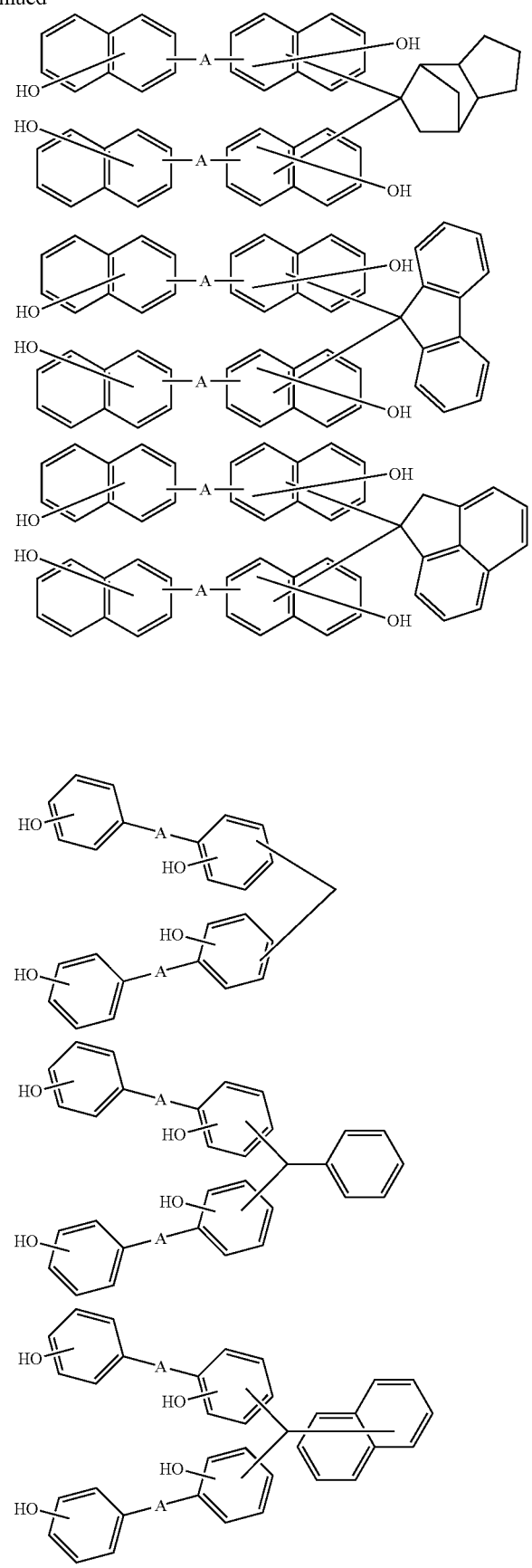

-continued
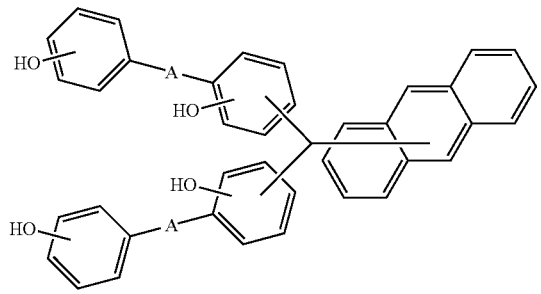
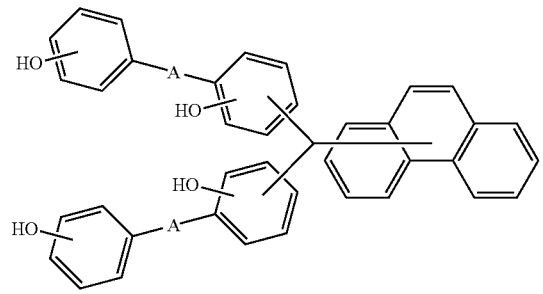
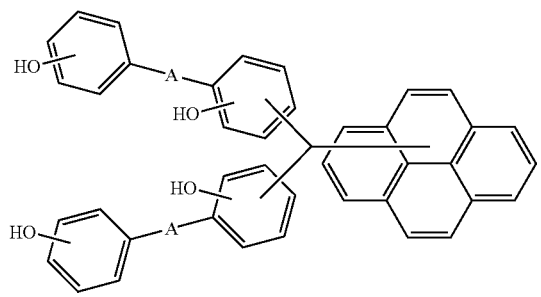
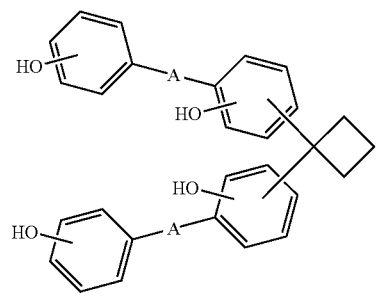
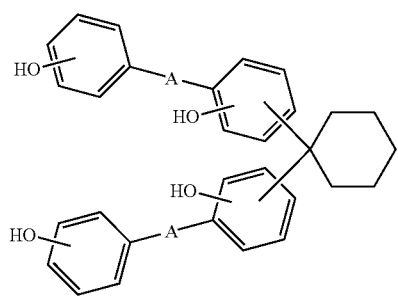
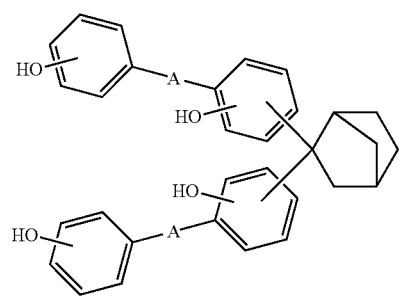
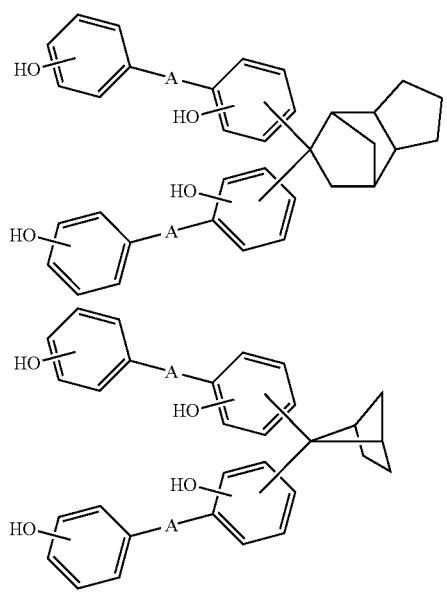
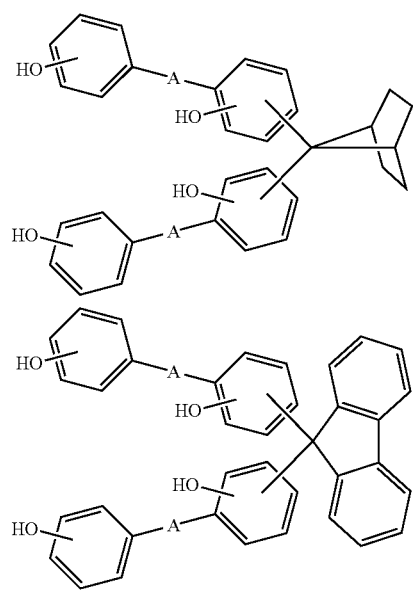

-continued
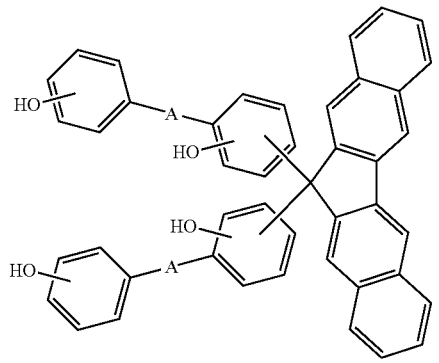
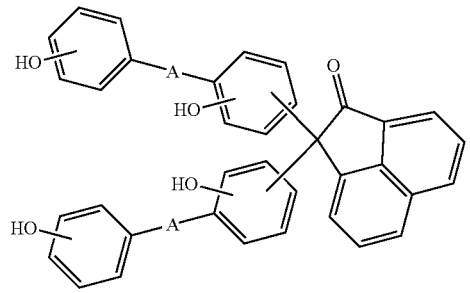
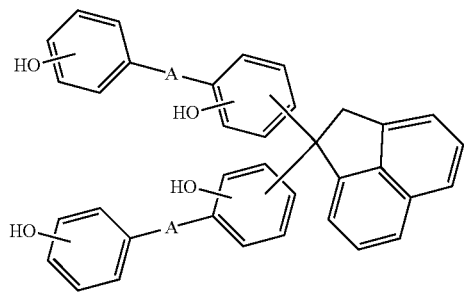
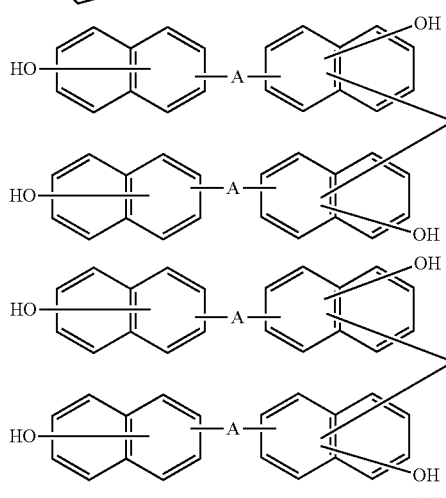
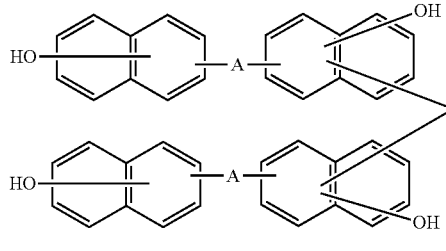
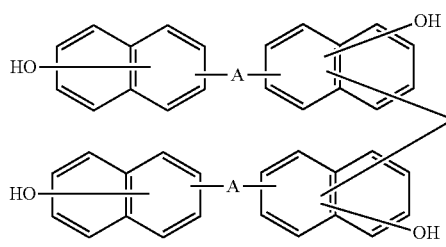

-continued
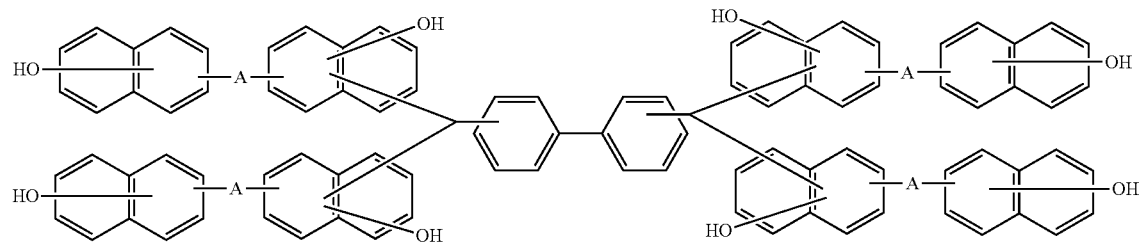
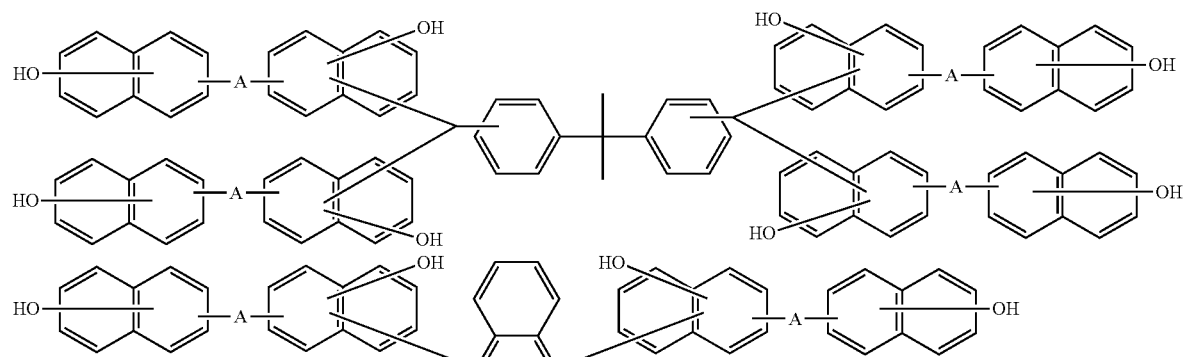
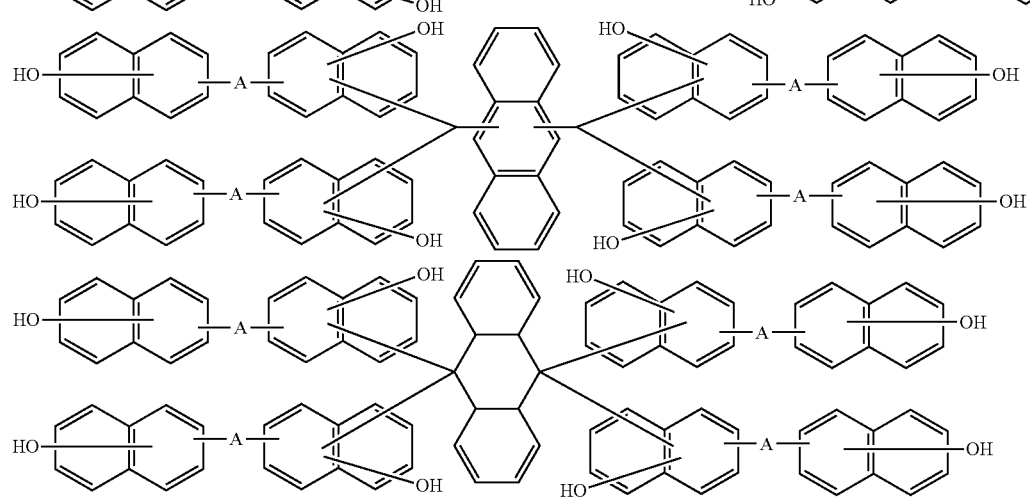
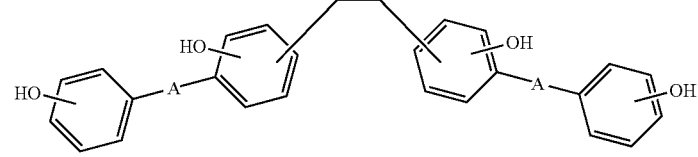
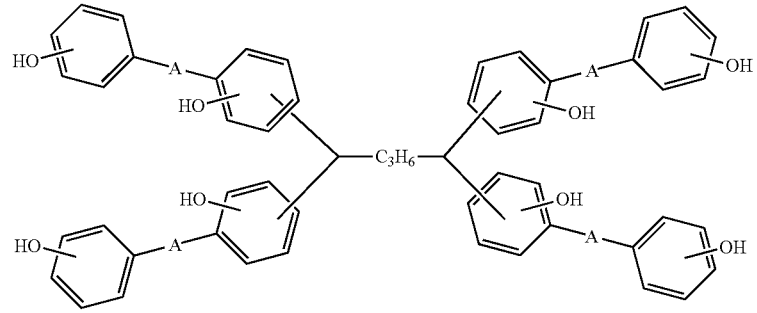

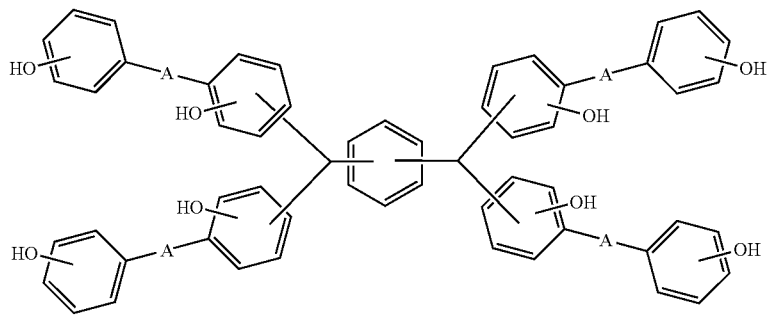
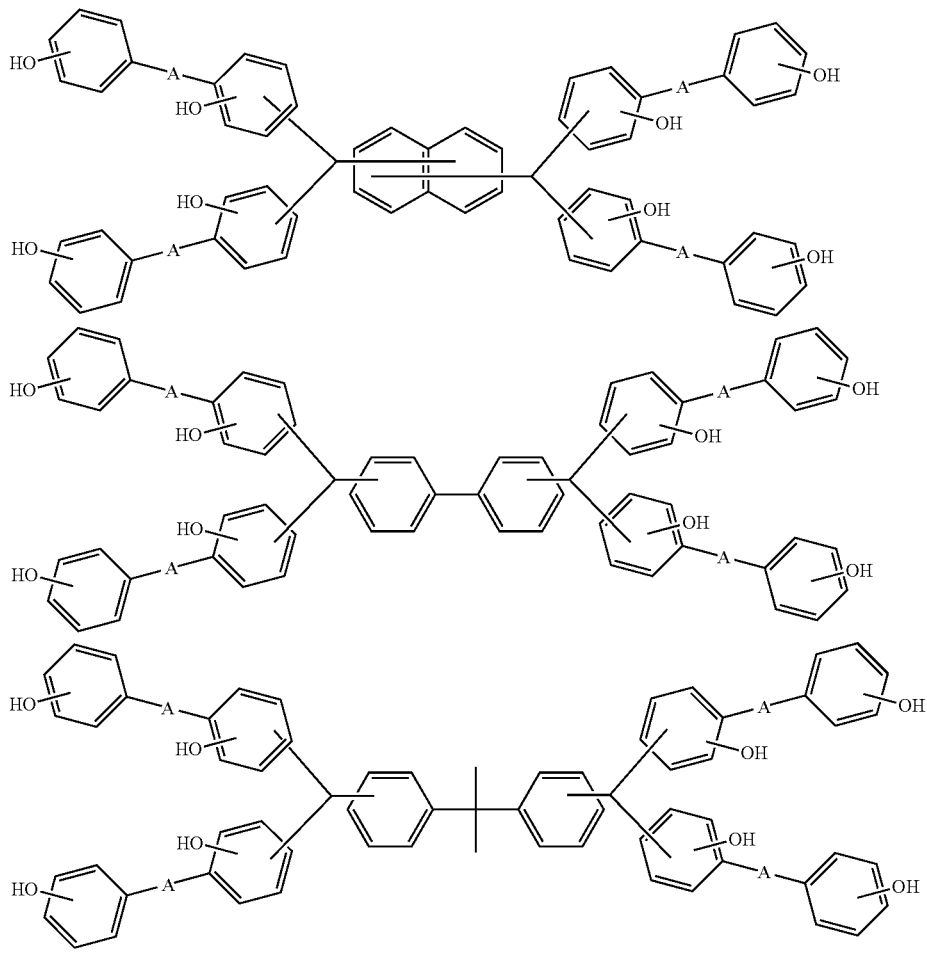
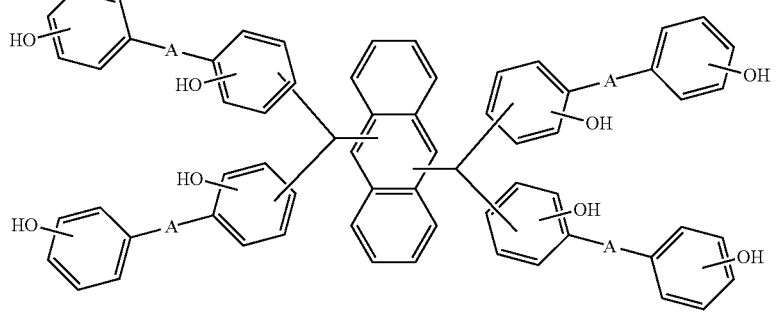

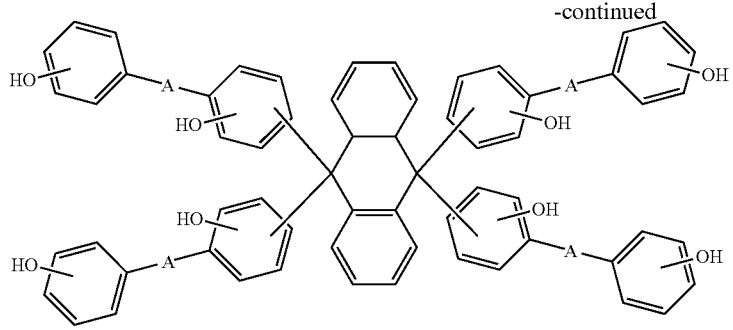

In each of the above formulas, A is as defined in the above formula (1).

Examples of the method for synthesizing the compound represented by the formula (1) include the following method. That is, the compound represented by the above formula (1) is obtained through a polycondensation reaction among the compound represented by the following formula (1-x), the compound represented by the following formula (1-y), and the compound represented by the following formula (z1) or the following formula (z2) in the presence of an acid catalyst or base catalyst at normal pressure. If necessary, the above reaction may be carried out under increased pressure.

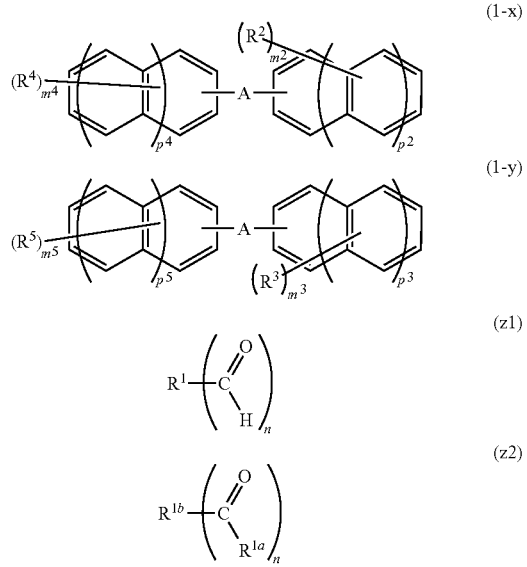

In the above formula (1-x), A, $R^2$, $R^4$, $m^2$, $m^4$, $p^2$, and $p^4$ are each as defined in the formula (1). In the above formula (1-y), A, $R^3$, $R^5$, $m^3$, $m^5$, $p^3$, and $p^5$ are each as defined in the formula (1). The compound represented by the above formula (1-x) may be the same as the compound represented by the above formula (1-y).

In the above formula (z1), $R^1$ and n are each as defined in the above formula (1). In the above formula (z2), $R^{1a}$, $R^{1b}$, and n are each as defined in the above formula (1-1).

As a specific example of the polycondensation reaction, the compound represented by the above formula (1) is obtained through a polycondensation reaction between a bis(hydroxyphenyl) compound and a corresponding aldehyde or ketone in the presence of an acid catalyst or base catalyst.

Examples of the bis(hydroxyphenyl) compound include, without particular limitations, bis(hydroxyphenyl)methane, bis(hydroxyphenyl)ethane, bis(hydroxyphenyl)propane, bis(hydroxyphenyl)butane, bis(hydroxyphenyl)phenylmethane, bis(hydroxyphenyl)phenylethane, bis(hydroxyphenyl)difluoromethane, bis(hydroxyphenyl)hexafluoropropane, bis(hydroxyphenyl)diphenylmethane, bis(methylhydroxyphenyl)propane, bis(dimethylhydroxyphenyl)propane, bis(hydroxyphenyl)dichloroethylene, bis(hydroxyphenyl), bis(hydroxyphenyl)carbonyl, bis(hydroxyphenyl)trimethylcyclohexane, bis(hydroxyphenyl)cyclohexane, bis(hydroxyphenyl)cyclododecane, bis(hydroxyphenyl)carbonyl, bis(dihydroxyphenyl)carbonyl, (hydroxyphenyl)(dihydroxyphenyl)carbonyl, and (hydroxyphenyl) (trihydroxyphenyl) carbonyl. These bis(hydroxyphenyl) compounds are used alone as one kind or in combination of two or more kinds. Among them, it is preferable to use bis(hydroxyphenyl)methane, bis(hydroxyphenyl)ethane, bis(hydroxyphenyl)propane, bis(hydroxyphenyl)butane, bis(hydroxyphenyl)phenylmethane, bis(hydroxyphenyl)phenylethane, bis(hydroxyphenyl)difluoromethane, bis(hydroxyphenyl)hexafluoropropane, bis(hydroxyphenyl)diphenylmethane, or bis(methylhydroxyphenyl)propane from the viewpoint of the stable supply of raw materials.

Examples of the aldehyde include, without particular limitations, formaldehyde, trioxane, paraformaldehyde, benzaldehyde, acetaldehyde, propylaldehyde, phenylacetaldehyde, phenylpropylaldehyde, hydroxybenzaldehyde, chlorobenzaldehyde, nitrobenzaldehyde, methylbenzaldehyde, dimethylbenzaldehyde, trimethylbenzaldehyde, ethylbenzaldehyde, propylbenzaldehyde, butylbenzaldehyde, pentabenzaldehyde, butylmethylbenzaldehyde, hydroxybenzaldehyde, dihydroxybenzaldehyde, fluoromethylbenzaldehyde, cyclopropylaldehyde, cyclobutylaldehyde, cyclohexylaldehyde, cyclodecylaldehyde, cycloundecylaldehyde, cyclopropylbenzaldehyde, cyclobutylbenzaldehyde, cyclohexylbenzaldehyde, cyclodecylbenzaldehyde, cycloundecylbenzaldehyde, biphenylaldehyde, naphthaldehyde, anthracenecarbaldehyde, phenanthrenecarbaldehyde, pyrenecarbaldehyde, and furfural. These aldehydes are used alone as one kind or in combination of two or more kinds. Among them, it is preferable to use one or more selected from the group consisting of benzaldehyde, phenylacetaldehyde, phenylpropylaldehyde, hydroxybenzaldehyde, chlorobenzaldehyde, nitrobenzaldehyde, methylbenzaldehyde, ethylbenzaldehyde, butylbenzaldehyde, cyclohexylbenzaldehyde, biphenylaldehyde, naphthaldehyde, anthracenecarbaldehyde, phenanthrenecarbaldehyde, pyrenecarbaldehyde and furfural from the viewpoint that high heat resistance can be exhibited, and it is more preferable to use one or more selected from the group consisting of benzaldehyde, hydroxybenzaldehyde, chlorobenzaldehyde, nitrobenzaldehyde, methylbenzaldehyde, ethylbenzaldehyde, butylbenzaldehyde, cyclohexylbenzaldehyde, biphenylaldehyde, naphthaldehyde, anthracenecarbaldehyde, phenanthrenecarbaldehyde, pyrenecarbaldehyde and furfural from the viewpoint of improving etching resistance.

Examples of the ketone include, without particular limitations, acetone, methyl ethyl ketone, cyclobutanone, cyclopentanone, cyclohexanone, norbornanone, tricyclohexanone, tricyclodecanone, adamantanone, fluorenone, benzofluorenone, acenaphthenequinone, acenaphthenone, anthraquinone, acetophenone, diacetylbenzene, triacetylbenzene, acetonaphthone, acetylmethylbenzene, acetyldimethylbenzene, acetyltrimethylbenzene, acetylethylbenzene, acetylpropylbenzene, acetylbutylbenzene, acetylpentabenzene, acetylbutylmethylbenzene, acetylhydroxybenzene, acetyldihydroxybenzene, acetylfluoromethylbenzene, diphenylcarbonylnaphthalene, phenylcarbonylbiphenyl, diphenylcarbonylbiphenyl, benzophenone, diphenylcarbonylbenzene, triphenylcarbonylbenzene, benzonaphthone, diphenylcarbonylnaphthalene, phenylcarbonylbiphenyl, and diphenylcarbonylbiphenyl. These ketones are used alone as one kind or in combination of two or more kinds. Among them, it is preferable to use one or more selected from the group consisting of cyclopentanone, cyclohexanone, norbornanone, tricyclohexanone, tricyclodecanone, adamantanone, fluorenone, benzofluorenone, acenaphthenequinone, acenaphthenone, anthraquinone, acetophenone, diacetylbenzene, triacetylbenzene, acetonaphthone, diphenylcarbonylnaphthalene, phenylcarbonylbiphenyl, diphenylcarbonylbiphenyl, benzophenone, diphenylcarbonylbenzene, triphenylcarbonylbenzene, benzonaphthone, diphenylcarbonylnaphthalene, phenylcarbonylbiphenyl and diphenylcarbonylbiphenyl from the viewpoint that high heat resistance can be exhibited, and it is more preferable to use one or more selected from the group consisting of acetophenone, diacetylbenzene, triacetylbenzene, acetonaphthone, diphenylcarbonylnaphthalene, phenylcarbonylbiphenyl, diphenylcarbonylbiphenyl, benzophenone, diphenylcarbonylbenzene, triphenylcarbonylbenzene, benzonaphthone, diphenylcarbonylnaphthalene, phenylcarbonylbiphenyl and diphenylcarbonylbiphenyl from the viewpoint of improving etching resistance.

As the aldehyde or the ketone, an aldehyde or a ketone having an aromatic ring is preferably used from the viewpoint that both high heat resistance and high etching resistance are achieved.

Examples of the acid catalyst to be used in the above reaction include, without particular limitations, an inorganic acid such as hydrochloric acid, sulfuric acid, phosphoric acid, hydrobromic acid, and hydrofluoric acid; an organic acid such as oxalic acid, malonic acid, succinic acid, adipic acid, sebacic acid, citric acid, fumaric acid, maleic acid, formic acid, p-toluenesulfonic acid, methanesulfonic acid, trifluoroacetic acid, dichloroacetic acid, trichloroacetic acid, trifluoromethanesulfonic acid, benzenesulfonic acid, naphthalenesulfonic acid, and naphthalenedisulfonic acid; a Lewis acid such as zinc chloride, aluminum chloride, iron chloride, and boron trifluoride; and a solid acid such as tungstosilicic acid, tungstophosphoric acid, silicomolybdic acid, and phosphomolybdic acid. These acid catalysts are used alone as one kind or in combination of two or more kinds. Among them, organic acids and solid acids are preferable from the viewpoint of production, and it is preferable to use hydrochloric acid or sulfuric acid from the viewpoint of production such as easy availability and handleability. The amount of the acid catalyst used can be arbitrarily set according to, for example, the kind of the raw materials used and the catalyst used and moreover the reaction conditions and is not particularly limited, and is preferably 0.01 to 100 parts by mass based on 100 parts by mass of the reaction raw materials.

Examples of the base catalyst to be used in the above reaction include, without particular limitations, a metal alkoxide (for example, an alkali metal or alkaline earth metal alkoxide such as sodium methoxide, sodium ethoxide, potassium methoxide and potassium ethoxide), a metal hydroxide (for example, an alkali metal or alkaline earth metal hydroxide such as sodium hydroxide and potassium hydroxide), an alkali metal or alkaline earth bicarbonate such as sodium bicarbonate and potassium bicarbonate, and an organic base of an amine (for example, a tertiary amine (a trialkylamine such as triethylamine, an aromatic tertiary amine such as N,N-dimethylaniline, and a heterocyclic tertiary amine such as 1-methylimidazole), and a metal carboxylate (for example, an alkali metal or alkaline earth metal acetate such as sodium acetate and calcium acetate). These base catalysts are used alone as one kind or in combination of two or more kinds. Among them, metal alkoxides, metal hydroxides and amines are preferable from the viewpoint of production, and it is preferable to use sodium hydroxide from the viewpoint of production such as easy availability and handleability. The amount of the base catalyst used can be arbitrarily set according to, for example, the kind of the raw materials used and the catalyst used and moreover the reaction conditions and is not particularly limited, and is preferably 0.01 to 100 parts by mass based on 100 parts by mass of the reaction raw materials.

Upon the above reaction, a reaction solvent may be used. Examples of the reaction solvent include, without particular limitations, water, methanol, ethanol, propanol, butanol, tetrahydrofuran, dioxane, ethylene glycol dimethyl ether, and ethylene glycol diethyl ether. These solvents are used alone as one kind or in combination of two or more kinds.

The amount of the solvent used can be arbitrarily set according to, for example, the kind of the raw materials used and the catalyst used and moreover the reaction conditions and is not particularly limited, and is preferably in the range of 0 to 2000 parts by mass based on 100 parts by mass of the reaction raw materials. Furthermore, the reaction temperature in the above reaction can be arbitrarily selected according to the reactivity of the reaction raw materials and is not particularly limited, and is usually within the range of 10 to 200° C.

In order to obtain the compound represented by the formula (1) of the present embodiment, a higher reaction temperature is preferable. Specifically, the range of 60 to 200° C. is preferable. Although the reaction method is not particularly limited, for example, the raw materials (reactants) and the catalyst may be fed in a batch, or the raw materials (reactants) may be dripped successively in the presence of the catalyst. After the polycondensation reaction terminates, isolation of the obtained compound can be carried out according to a conventional method, and is not particularly limited. For example, by adopting a commonly used approach in which the temperature of the reaction vessel is elevated to 130 to 230° C. in order to remove unreacted raw materials, catalyst, etc. present in the system, and volatile portions are removed at about 1 to 50 mmHg, the compound that is the target compound can be obtained.

Examples of the preferable reaction conditions include conditions under which the reaction proceeds by using 1.0 mol to an excess of the compound represented by the above formula (1-x) and the compound represented by the above formula (1-y) based on 1 mol of the aldehyde or the ketone represented by the above formula (z1) or (z2), further using 0.001 to 1 mol of the acid catalyst, and reacting them at 50 to 150° C. at normal pressure for about 20 minutes to 100 hours.

The target compound can be isolated by a publicly known method after the reaction terminates. The compound represented by the above formula (1) which is the target compound can be obtained by, for example, concentrating the reaction liquid, precipitating the reaction product by the addition of pure water, cooling the reaction liquid to room temperature, then separating the precipitates by filtration, filtering and drying the obtained solid matter, then separating and purifying the solid matter from by-products by column chromatography, and distilling off the solvent, followed by filtration and drying.

[Resin]

The resin of the present embodiment has a constitutional unit derived from the compound represented by the above formula (1). That is, the resin of the present embodiment contains the compound represented by the above formula (1) as a monomer component. Specific examples of the resin of the present embodiment include a resin having a structure represented by the formula (2).

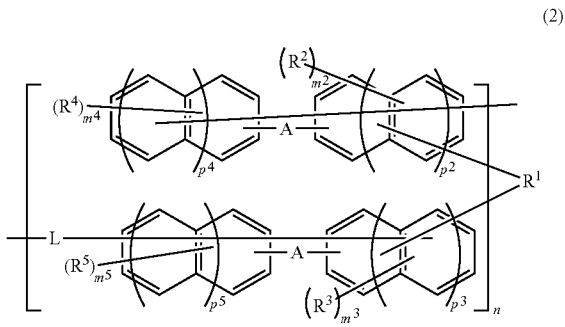

(2)

In the above formula (2), A, $R^1$ to $R^5$, $m^2$ to $m^5$, n, and $p^2$ to $p^5$ are each as defined in the above formula (1); and L is a single bond or a linking group.

Examples of the above linking group include a residue derived from the crosslinking compound, which will be mentioned later.

The resin of the present embodiment is obtained by reacting the compound represented by the above formula (1) with a crosslinking compound.

The crosslinking compound may be any compound as long as it can oligomerize or polymerize the compound represented by the above formula (1), and examples thereof include an aldehyde, a ketone, a carboxylic acid, a carboxylic acid halide, a halogen containing compound, an amino compound, an imino compound, an isocyanate compound, and an unsaturated hydrocarbon group containing compound.

Specific examples of the resin of the present embodiment include a resin that has been made novolac obtained through, for example, a condensation reaction between the compound represented by the above formula (1) and an aldehyde or ketone, which is a crosslinking compound.

Here, examples of the aldehyde to be used upon making the compound represented by the above formula (1) novolac include, without particular limitations, formaldehyde, trioxane, paraformaldehyde, benzaldehyde, acetaldehyde, propylaldehyde, phenylacetaldehyde, phenylpropylaldehyde, hydroxybenzaldehyde, chlorobenzaldehyde, nitrobenzaldehyde, methylbenzaldehyde, ethylbenzaldehyde, butylbenzaldehyde, biphenylaldehyde, naphthaldehyde, anthracenecarbaldehyde, phenanthrenecarbaldehyde, pyrenecarbaldehyde, and furfural. These aldehydes are used alone as one kind or in combination of two or more kinds. Among them, it is preferable to use one or more selected from the group consisting of benzaldehyde, phenylacetaldehyde, phenylpropylaldehyde, hydroxybenzaldehyde, chlorobenzaldehyde, nitrobenzaldehyde, methylbenzaldehyde, ethylbenzaldehyde, butylbenzaldehyde, cyclohexylbenzaldehyde, biphenylaldehyde, naphthaldehyde, anthracenecarbaldehyde, phenanthrenecarbaldehyde, pyrenecarbaldehyde and furfural from the viewpoint that high heat resistance can be exhibited; it is preferable to use one or more selected from the group consisting of benzaldehyde, hydroxybenzaldehyde, chlorobenzaldehyde, nitrobenzaldehyde, methylbenzaldehyde, ethylbenzaldehyde, butylbenzaldehyde, cyclohexylbenzaldehyde, biphenylaldehyde, naphthaldehyde, anthracenecarbaldehyde, phenanthrenecarbaldehyde, pyrenecarbaldehyde and furfural from the viewpoint of improving etching resistance; and it is more preferable to use formaldehyde. The amount of the aldehyde used is not particularly limited, and is preferably 0.2 to 5 mol and more preferably 0.5 to 2 mol based on 1 mol of the compound represented by the above formula (1).

Examples of the ketone to be used upon making the compound represented by the above formula (1) novolac include, without particular limitations, acetone, methyl ethyl ketone, cyclobutanone, cyclopentanone, cyclohexanone, norbornanone, tricyclohexanone, tricyclodecanone, adamantanone, fluorenone, benzofluorenone, acenaphthenequinone, acenaphthenone, anthraquinone, acetophenone, diacetylbenzene, triacetylbenzene, acetonaphthone, diphenylcarbonylnaphthalene, phenylcarbonylbiphenyl, diphenylcarbonylbiphenyl, benzophenone, diphenylcarbonylbenzene, triphenylcarbonylbenzene, benzonaphthone, diphenylcarbonylnaphthalene, phenylcarbonylbiphenyl, and diphenylcarbonylbiphenyl. These ketones are used alone as one kind or in combination of two or more kinds. Among them, it is preferable to use one or more selected from the group consisting of cyclopentanone, cyclohexanone, norbornanone, tricyclohexanone, tricyclodecanone, adamantanone, fluorenone, benzofluorenone, acenaphthenequinone, acenaphthenone, anthraquinone, acetophenone, diacetylbenzene, triacetylbenzene, acetonaphthone, diphenylcarbonylnaphthalene, phenylcarbonylbiphenyl, diphenylcarbonylbiphenyl, benzophenone, diphenylcarbonylbenzene, triphenylcarbonylbenzene, benzonaphthone, diphenylcarbonylnaphthalene, phenylcarbonylbiphenyl and diphenylcarbonylbiphenyl from the viewpoint that high heat resistance can be exhibited, and it is more preferable to use one or more selected from the group consisting of acetophenone, diacetylbenzene, triacetylbenzene, acetonaphthone, diphenylcarbonylnaphthalene, phenylcarbonylbiphenyl, diphenylcarbonylbiphenyl, benzophenone, diphenylcarbonylbenzene, triphenylcarbonylbenzene, benzonaphthone, diphenylcarbonylnaphthalene, phenylcarbonylbiphenyl and diphenylcarbonylbiphenyl from the viewpoint of improving etching resistance. The amount of the ketone used is not particularly limited, and is preferably 0.2 to 5 mol and more preferably 0.5 to 2 mol based on 1 mol of the compound represented by the above formula (1).

A catalyst can also be used in the condensation reaction between the compound represented by the above formula (1) and the aldehyde or ketone. The acid catalyst or base catalyst to be used herein can be arbitrarily selected for use from publicly known catalysts and is not particularly limited. Examples of such an acid catalyst include, without particular limitations, an inorganic acid such as hydrochloric acid, sulfuric acid, phosphoric acid, hydrobromic acid, and hydrofluoric acid; an organic acid such as oxalic acid, malonic acid, succinic acid, adipic acid, sebacic acid, citric acid, fumaric acid, maleic acid, formic acid, p-toluenesulfonic acid, methanesulfonic acid, trifluoroacetic acid, dichloroacetic acid, trichloroacetic acid, trifluoromethanesulfonic acid, benzenesulfonic acid, naphthalenesulfonic acid, and naphthalenedisulfonic acid; a Lewis acid such as zinc chloride, aluminum chloride, iron chloride, and boron trifluoride; and a solid acid such as tungstosilicic acid, tungstophosphoric acid, silicomolybdic acid, and phosphomolybdic acid. These catalysts are used alone as one kind or in combination of two or more kinds. Among them, organic acids and solid acids are preferable from the viewpoint of production, and hydrochloric acid or sulfuric acid is preferable from the viewpoint of production such as easy availability and handleability. The amount of the acid catalyst used can be arbitrarily set according to, for example, the kind of the raw materials used and the catalyst used and moreover the reaction conditions and is not particularly limited, and is preferably 0.01 to 100 parts by mass based on 100 parts by mass of the reaction raw materials.

However, in the case of a copolymerization reaction with a compound having a non-conjugated double bond, such as indene, hydroxyindene, benzofuran, hydroxyanthracene, acenaphthylene, biphenyl, bisphenol, trisphenol, dicyclopentadiene, tetrahydroindene, 4-vinylcyclohexene, norbornadiene, 5-vinylnorborn-2-ene, α-pinene, β-pinene and limonene, the aldehyde or ketone is not necessarily needed.

A reaction solvent can also be used in the condensation reaction between the compound represented by the above formula (1) and the aldehyde or ketone. The reaction solvent in the polycondensation can be arbitrarily selected for use from publicly known solvents and is not particularly limited, and examples thereof include water, methanol, ethanol, propanol, butanol, tetrahydrofuran, dioxane, and a mixed solvent thereof. These solvents are used alone as one kind or in combination of two or more kinds.

The amount of the solvent used can be arbitrarily set according to, for example, the kind of the raw materials used and the catalyst used and moreover the reaction conditions and is not particularly limited, and is preferably in the range of 0 to 2000 parts by mass based on 100 parts by mass of the reaction raw materials. Furthermore, the reaction temperature can be arbitrarily selected according to the reactivity of the reaction raw materials and is not particularly limited, and is usually within the range of 10 to 200° C. Examples of the reaction method include a method in which the compound represented by the above formula (1), the aldehyde and/or ketone, and the catalyst are fed in a batch, or a method in which the compound represented by the above formula (1) and the aldehyde and/or ketone are dripped successively in the presence of the catalyst.

After the polycondensation reaction terminates, isolation of the obtained compound can be carried out according to a conventional method, and is not particularly limited. For example, by adopting a commonly used approach in which the temperature of the reaction vessel is elevated to 130 to 230° C. in order to remove unreacted raw materials, catalyst, etc. present in the system, and volatile portions are removed at about 1 to 50 mmHg, the target compound (for example, the resin that has been made novolac) can be obtained.

The resin of the present embodiment is also obtained upon the synthesis reaction of the compound represented by the above formula (1). This corresponds to the case where the same aldehyde or ketone is used upon polymerizing the compound represented by the above formula (1) as that used in the synthesis of the compound of the above formula (1).

Here, the resin of the present embodiment may be a homopolymer of the compound represented by the above formula (1), or may be a copolymer with a further phenol. Here, examples of the copolymerizable phenol include, without particular limitations, phenol, cresol, dimethylphenol, trimethylphenol, butylphenol, phenylphenol, diphenylphenol, naphthylphenol, resorcinol, methylresorcinol, catechol, butylcatechol, methoxyphenol, methoxyphenol, propylphenol, pyrogallol, and thymol.

In addition, the resin of the present embodiment may be a copolymer with a polymerizable monomer other than the further phenol mentioned above. Examples of the copolymerization monomer include, without particular limitations, naphthol, methylnaphthol, methoxynaphthol, dihydroxynaphthalene, indene, hydroxyindene, benzofuran, hydroxyanthracene, acenaphthylene, biphenyl, bisphenol, trisphenol, dicyclopentadiene, tetrahydroindene, 4-vinylcyclohexene, norbornadiene, vinylnorbornene, pinene, and limonene. The resin of the present embodiment may be a copolymer of two or more components (for example, a binary to quaternary system) composed of the compound represented by the above formula (1) and the above phenol, may be a copolymer of two or more components (for example, a binary to quaternary system) composed of the compound represented by the above formula (1) and the above copolymerization monomer, or may be a copolymer of three or more components (for example, a tertiary to quaternary system) composed of the compound represented by the above formula (1), the above phenol, and the above copolymerization monomer.

The weight average molecular weight (Mw) of the resin of the present embodiment is not particularly limited, and is, in terms of polystyrene through GPC measurement, preferably 500 to 30,000 and more preferably 750 to 20,000. In addition, the resin of the present embodiment preferably has dispersibility (weight average molecular weight Mw/number average molecular weight Mn) within the range of 1.2 to 7 from the viewpoint of enhancing crosslinking efficiency while suppressing volatile components during baking.

It is preferable that the compound represented by the above formula (1), and/or the resin having a constitutional unit derived from the compound represented by the formula (1) have high solubility in a solvent from the viewpoint of easier application to a wet process, etc. More specifically, in the case of using propylene glycol monomethyl ether (PGME) and/or propylene glycol monomethyl ether acetate (PGMEA) as a solvent, it is preferable that the compound and/or resin have a solubility of 10% by mass or more in the solvent. Here, the solubility in PGME and/or PGMEA is defined as "mass of the resin/(mass of the resin+mass of the solvent)×100 (% by mass)". For example, 10 g of the compound represented by the above formula (1) and/or the resin having a constitutional unit derived from the compound is evaluated as being dissolved in 90 g of PGMEA when the solubility of the compound represented by the formula (1) and/or the resin having a constitutional unit derived from the compound in PGMEA is "10% by mass or more"; and 10 g of the compound and/or the resin is evaluated as being not dissolved in 90 g of PGMEA when the solubility is "less than 10% by mass".

[Composition]

The composition of the present embodiment contains the compound represented by the formula (1) or the resin having a constitutional unit derived from the compound represented by the formula (1).

The composition of the present embodiment contains the compound or the resin of the present embodiment, and is thus applicable to a wet process and is excellent in heat resistance and smoothing properties. Furthermore, the composition of the present embodiment contains the compound or the resin, and can therefore form a film for lithography that is prevented from being deteriorated upon baking at a high temperature, and is excellent in etching resistance against oxygen plasma etching or the like. Furthermore, the composition of the present embodiment is also excellent in adhesiveness to a resist layer and can therefore form an excellent resist pattern. For this reason, the composition of the present embodiment is suitably used in film formation for lithography.

The composition of the present embodiment has high refractive index ascribable to its high aromatic density and is prevented from being stained by heat treatment in a wide range from a low temperature to a high temperature. For this reason, the composition of the present embodiment is also suitably used in optical component formation.

In the present embodiment, the film for lithography refers to a film having a higher dry etching rate compared with that of the photoresist layer. Examples of the film for lithography include a film used for embedding and smoothening steps of layers to be processed, a resist upper layer film, and a resist underlayer film.

The film forming composition for lithography of the present embodiment may contain a solvent, a crosslinking agent, a crosslinking promoting agent, an acid generating agent, a basic compound, and a further component, in addition to the compound or the resin of the present embodiment, if required. Hereinafter, these optional components will be described.

[Solvent]

The film forming composition for lithography of the present embodiment may contain a solvent. The solvent is not particularly limited as long as it is a solvent that can dissolves the compound or the resin of the present embodiment. Here, the compound or the resin of the present embodiment has excellent solubility in an organic solvent, as mentioned above, and therefore, various organic solvents are suitably used.

Examples of the solvent include, but are not particularly limited to: a ketone-based solvent such as acetone, methyl ethyl ketone, methyl isobutyl ketone, and cyclohexanone; a cellosolve-based solvent such as propylene glycol monomethyl ether and propylene glycol monomethyl ether acetate; an ester-based solvent such as ethyl lactate, methyl acetate, ethyl acetate, butyl acetate, isoamyl acetate, ethyl lactate, methyl methoxypropionate, and methyl hydroxyisobutyrate; an alcohol-based solvent such as methanol, ethanol, isopropanol, and 1-ethoxy-2-propanol; and an aromatic hydrocarbon such as toluene, xylene, and anisole. These solvents are used alone as one kind or in combination of two or more kinds.

Among the above solvents, from the viewpoint of safety, one or more selected from the group consisting of cyclohexanone, propylene glycol monomethyl ether, propylene glycol monomethyl ether acetate, ethyl lactate, methyl hydroxyisobutyrate and anisole are preferable.

The content of the solvent is not particularly limited, and is preferably 100 to 10,000 parts by mass, more preferably 200 to 5,000 parts by mass, and further preferably 200 to 1,000 parts by mass based on 100 parts by mass of the compound or the resin of the present embodiment from the viewpoint of solubility and film formation.

[Crosslinking Agent]

The film forming composition for lithography of the present embodiment may contain a crosslinking agent from the viewpoint of, for example, suppressing intermixing. The crosslinking agent is not particularly limited, and a crosslinking agent described in, for example, International Publication No. WO 2013/024779 or International Publication No. WO 2018/016614 can be used.

Examples of the crosslinking agent include, but not particularly limited to, a phenol compound, an epoxy compound, a cyanate compound, an amino compound, a benzoxazine compound, an acrylate compound, a melamine compound, a guanamine compound, a glycoluril compound, a urea compound, an isocyanate compound, and an azide compound. These crosslinking agents are used alone as one kind or in combination of two or more kinds. Among them, one or more selected from the group consisting of a benzoxazine compound, an epoxy compound and a cyanate compound are preferable, and a benzoxazine compound is more preferable from the viewpoint of improvement in etching resistance.

In the present embodiment, the content of the crosslinking agent is not particularly limited, and is preferably 0.1 to 100 parts by mass, more preferably 5 to 50 parts by mass, and further preferably 10 to 40 parts by mass based on 100 parts by mass of the compound or the resin of the present embodiment. By setting the content of the crosslinking agent to the above range, occurrence of a mixing event with a resist layer tends to be prevented. Also, an antireflection effect is enhanced, and film formability after crosslinking tends to be enhanced.

[Crosslinking Promoting Agent]

The film forming composition for lithography of the present embodiment may contain a crosslinking promoting agent for accelerating crosslinking reaction (curing reaction), if required. Examples of the crosslinking promoting agent include a radical polymerization initiator.

The radical polymerization initiator may be a photopolymerization initiator that initiates radical polymerization by light, or may be a thermal polymerization initiator that initiates radical polymerization by heat. Examples of the radical polymerization initiator include at least one selected from the group consisting of a ketone-based photopolymerization initiator, an organic peroxide-based polymerization initiator and an azo-based polymerization initiator.

Such a radical polymerization initiator is not particularly limited, and a radical polymerization initiator described in, for example, International Publication No. WO 2018/016614 can be used.

These radical polymerization initiators are used alone as one kind or in combination of two or more kinds.

The content of the radical polymerization initiator in the present embodiment can be a stoichiometrically necessary amount and is preferably 0.05 to 25 parts by mass, and more preferably 0.1 to 10 parts by mass based on 100 parts by mass of the compound or the resin of the present embodiment. When the content of the radical polymerization initiator is 0.05 parts by mass or more, there is a tendency that curing can be prevented from being insufficient. On the other hand, when the content of the radical polymerization initiator is 25 parts by mass or less, there is a tendency that the long term storage stability at room temperature can be prevented from being impaired.

[Acid Generating Agent]

The film forming composition for lithography of the present embodiment may contain an acid generating agent from the viewpoint of, for example, further accelerating crosslinking reaction by heat. An acid generating agent that generates an acid by thermal decomposition, an acid generating agent that generates an acid by light irradiation, and the like are known, any of which can be used. For example, an acid generating agent described in International Publication No. WO 2013/024779 can be used.

The content of the acid generating agent in the film forming composition for lithography is not particularly limited and is preferably 0.1 to 50 parts by mass, and more preferably 0.5 to 40 parts by mass based on 100 parts by mass of the compound or the resin of the present embodiment. By setting the content of the acid generating agent to the above range, crosslinking reaction tends to be enhanced and occurrence of a mixing event with a resist layer tends to be prevented.

[Basic Compound]

The film forming composition for lithography of the present embodiment may also contain a basic compound from the viewpoint of, for example, improving storage stability.

The basic compound plays a role to prevent crosslinking reaction from proceeding due to a trace amount of an acid generated from the acid generating agent, that is, a role as a quencher against the acid. Examples of such a basic compound include, but are not particularly limited to, those described in International Publication No. WO 2013/024779.

The content of the basic compound in the film forming composition for lithography of the present embodiment is not particularly limited, and is preferably 0.001 to 2 parts by mass, and more preferably 0.01 to 1 part by mass based on 100 parts by mass of the compound or the resin of the present embodiment. By setting the content of the basic compound to the above range, storage stability tends to be enhanced without excessively deteriorating crosslinking reaction.

[Further Additive Agent]

The film forming composition for lithography of the present embodiment may also contain an additional resin and/or compound for the purpose of conferring thermosetting or light curing properties or controlling absorbance. Examples of such an additional resin and/or compound include, without particular limitations, a naphthol resin, a xylene resin naphthol-modified resin, a phenol-modified resin of a naphthalene resin; a polyhydroxystyrene, a dicyclopentadiene resin, a resin containing (meth)acrylate, dimethacrylate, trimethacrylate, tetramethacrylate, a naphthalene ring such as vinylnaphthalene or polyacenaphthylene, a biphenyl ring such as phenanthrenequinone or fluorene, or a heterocyclic ring having a heteroatom such as thiophene or indene, and a resin containing no aromatic ring; and a resin or compound containing an alicyclic structure, such as a rosin-based resin, a cyclodextrin, an adamantine(poly)ol, a tricyclodecane(poly)ol, and a derivative thereof. The film forming composition for lithography of the present embodiment may also contain a publicly known additive agent. Examples of the publicly known additive agent include, but are not limited to, a thermal and/or light curing catalyst, a polymerization inhibitor, a flame retardant, a filler, a coupling agent, a thermosetting resin, a light curable resin, a dye, a pigment, a thickener, a lubricant, an antifoaming agent, a leveling agent, an ultraviolet absorber, a surfactant, a colorant, and a nonionic surfactant.

[Underlayer Film for Lithography]

The underlayer film for lithography of the present embodiment is formed from the film forming composition for lithography of the present embodiment.

[Resist Pattern Formation Method]

The resist pattern formation method of the present embodiment comprises: an underlayer film formation step of forming an underlayer film on a supporting material using the composition of the present embodiment; a photoresist layer formation step of forming at least one photoresist layer on the underlayer film formed through the underlayer film formation step; and a step of irradiating a predetermined region of the photoresist layer formed through the photoresist layer formation step with radiation for development. The resist pattern formation method of the present embodiment can be used for forming various patterns, and is preferably a method for forming an insulating film pattern.

[Circuit Pattern Formation Method]

The circuit pattern formation method of the present embodiment comprises: an underlayer film formation step of forming an underlayer film on a supporting material using the composition of the present embodiment; an intermediate layer film formation step of forming an intermediate layer film on the underlayer film formed through the underlayer film formation step; a photoresist layer formation step of forming at least one photoresist layer on the intermediate layer film formed through the intermediate layer film formation step; a resist pattern formation step of irradiating a predetermined region of the photoresist layer formed through the photoresist layer formation step with radiation for development, thereby forming a resist pattern; an intermediate layer film pattern formation step of etching the intermediate layer film with the resist pattern formed through the resist pattern formation step as a mask, thereby forming an intermediate layer film pattern; an underlayer film pattern formation step of etching the underlayer film with the intermediate layer film pattern formed through the intermediate layer film pattern formation step as a mask, thereby forming an underlayer film pattern; and a supporting material pattern formation step of etching the supporting material with the underlayer film pattern formed through the underlayer film pattern formation step as a mask, thereby forming a pattern on the supporting material.

The underlayer film for lithography of the present embodiment is formed from the film forming composition for lithography of the present embodiment. The formation method is not particularly limited and a publicly known method can be applied. The underlayer film can be formed by, for example, applying the film forming composition for lithography of the present embodiment onto a supporting material by a publicly known coating method or printing method such as spin coating or screen printing, and then removing an organic solvent by volatilization or the like.

It is preferable to perform baking in the formation of the underlayer film, for preventing occurrence of a mixing event with a resist upper layer film while accelerating crosslinking reaction. In this case, the baking temperature is not particularly limited and is preferably in the range of 80 to 450° C., and more preferably 200 to 400° C. The baking time is not particularly limited and is preferably in the range of 10 to 300 seconds. The thickness of the underlayer film can be arbitrarily selected according to required performance and is not particularly limited, and is preferably 30 to 20,000 nm, and more preferably 50 to 15,000 nm.

After preparing the underlayer film, it is preferable to prepare a silicon-containing resist layer or a single-layer resist made of hydrocarbon on the underlayer film in the case of a two-layer process, and to prepare a silicon-containing intermediate layer on the underlayer film and further prepare a silicon-free single-layer resist layer on the silicon-containing intermediate layer in the case of a three-layer process. In this case, a publicly known photoresist material can be used for forming this resist layer.

For the silicon-containing resist material for a two-layer process, a silicon atom-containing polymer such as a polysilsesquioxane derivative or a vinylsilane derivative is used as a base polymer, and a positive type photoresist material further containing an organic solvent, an acid generating agent, and if required, a basic compound or the like is preferably used, from the viewpoint of oxygen gas etching resistance. Here, a publicly known polymer that is used in this kind of resist material can be used as the silicon atom-containing polymer.

A polysilsesquioxane-based intermediate layer is preferably used as the silicon-containing intermediate layer for a three-layer process. By imparting effects as an antireflection film to the intermediate layer, there is a tendency that reflection can be effectively suppressed. For example, use of a material containing a large amount of an aromatic group and having high supporting material etching resistance as the underlayer film in a process for exposure at 193 nm tends to increase a k value and enhance supporting material reflection. However, the intermediate layer suppresses the reflection so that the supporting material reflection can be 0.5% or less. The intermediate layer having such an antireflection effect is not limited, and polysilsesquioxane that crosslinks by an acid or heat in which a light absorbing group having a phenyl group or a silicon-silicon bond is introduced is preferably used for exposure at 193 nm.

Alternatively, an intermediate layer formed by chemical vapour deposition (CVD) may be used. The intermediate layer highly effective as an antireflection film prepared by CVD is not limited, and, for example, a SiON film is known. In general, the formation of an intermediate layer by a wet process such as spin coating or screen printing is more convenient and more advantageous in cost than CVD. The upper layer resist for a three-layer process may be positive type or negative type, and the same as a single-layer resist generally used can be used.

The underlayer film according to the present embodiment can also be used as an antireflection film for usual single-layer resists or an underlying material for suppression of pattern collapse. The underlayer film is excellent in etching resistance for an underlying process and can be expected to also function as a hard mask for an underlying process.

In the case of forming a resist layer from the above photoresist material, a wet process such as spin coating or screen printing is preferably used, as in the case of forming the above underlayer film. After coating with the resist material by spin coating or the like, prebaking is generally performed. This prebaking is preferably performed at 80 to 180° C. in the range of 10 to 300 seconds. Then, exposure, post-exposure baking (PEB), and development can be performed according to a conventional method to obtain a resist pattern. The thickness of the resist film is not particularly limited, and in general, is preferably 30 to 500 nm and more preferably 50 to 400 nm.

The exposure light can be arbitrarily selected and used according to the photoresist material to be used. General examples thereof can include a high energy ray having a wavelength of 300 nm or less, specifically, excimer laser of 248 nm, 193 nm, or 157 nm, soft x-ray of 3 to 20 nm, electron beam, and X-ray.

In a resist pattern formed by the above method, pattern collapse is suppressed by the underlayer film. Therefore, use of the underlayer film according to the present embodiment can produce a finer pattern and can reduce an exposure amount necessary for obtaining the resist pattern.

Next, etching is performed with the obtained resist pattern as a mask. Gas etching is preferably used as the etching of the underlayer film in a two-layer process. The gas etching is suitably etching using oxygen gas. In addition to oxygen gas, an inert gas such as He or Ar, or CO, $CO_2$, $NH_3$, $SO_2$, $N_2$, $NO_2$, or $H_2$ gas may be added. Alternatively, the gas etching may be performed with CO, $CO_2$, $NH_3$, $N_2$, $NO_2$, or $H_2$ gas without the use of oxygen gas. Particularly, the latter gas is preferably used for side wall protection in order to prevent the undercut of pattern side walls.

On the other hand, gas etching is also preferably used as the etching of the intermediate layer in a three-layer process. The same gas etching as described in the above two-layer process is applicable. Particularly, it is preferable to process the intermediate layer in a three-layer process by using chlorofluorocarbon-based gas and using the resist pattern as a mask. Then, as mentioned above, for example, the underlayer film can be processed by oxygen gas etching with the intermediate layer pattern as a mask.

Here, in the case of forming an inorganic hard mask intermediate layer film as the intermediate layer, a silicon oxide film, a silicon nitride film, or a silicon oxynitride film (SiON film) is formed by CVD, ALD, or the like. A method for forming the nitride film is not limited, and for example, a method described in Japanese Patent Laid-Open No. 2002-334869 (Patent Literature 9) or WO 2004/066377 (Patent Literature 10) can be used. Although a photoresist film can be formed directly on such an intermediate layer film, an organic antireflection film (BARC) may be formed on the intermediate layer film by spin coating and a photoresist film may be formed thereon.

A polysilsesquioxane-based intermediate layer is suitably used as the intermediate layer. By imparting effects as an antireflection film to the resist intermediate layer film, there is a tendency that reflection can be effectively suppressed. A specific material for the polysilsesquioxane-based intermediate layer is not limited, and, for example, a material described in Japanese Patent Laid-Open No. 2007-226170 (Patent Literature 11) or Japanese Patent Laid-Open No. 2007-226204 (Patent Literature 12) can be used.

The subsequent etching of the supporting material can also be performed by a conventional method. For example, the supporting material made of $SiO_2$ or SiN can be etched mainly using chlorofluorocarbon-based gas, and the supporting material made of p-Si, Al, or W can be etched mainly using chlorine- or bromine-based gas. In the case of etching the supporting material with chlorofluorocarbon-based gas, the silicon-containing resist of the two-layer resist process or the silicon-containing intermediate layer of the three-layer process is stripped at the same time with supporting material processing. On the other hand, in the case of etching the supporting material with chlorine- or bromine-based gas, the silicon-containing resist layer or the silicon-containing intermediate layer is separately stripped and in general, stripped by dry etching using chlorofluorocarbon-based gas after supporting material processing.

A feature of the underlayer film of the present embodiment is that it is excellent in etching resistance of the supporting materials. The supporting material can be arbitrarily selected for use from publicly known ones and is not particularly limited. Examples thereof include Si, α-Si, p-Si, $SiO_2$, SiN, SiON, W, TiN, and Al. The supporting material may be a laminate having a film to be processed (supporting material to be processed) on a base material (support). Examples of such a film to be processed include various low-k films such as Si, $SiO_2$, SiON, SiN, p-Si, α-Si, W, W—Si, Al, Cu, and Al—Si, and stopper films thereof. A material different from that for the base material (support) is generally used. The thickness of the supporting material to be processed or the film to be processed is not particularly limited and is generally preferably about 50 to 1,000,000 nm, and more preferably 75 to 50,000 nm.

[Resist Permanent Film]

The resist permanent film of the present embodiment contains the composition of the present embodiment. The resist permanent film prepared by coating with the composition of the present embodiment is suitable as a permanent film that also remains in a final product, if required, after formation of a resist pattern. Specific examples of the permanent film include, in relation to semiconductor devices, a solder resist, a package material, an underfill material, a package adhesive layer for circuit elements and the like, and an adhesive layer between integrated circuit elements and circuit supporting materials, and in relation to thin displays, a thin film transistor protecting film, a liquid crystal color filter protecting film, a black matrix, and a spacer. Particularly, the resist permanent film containing the composition of the present embodiment is excellent in heat resistance and humidity resistance and furthermore, also has the excellent advantage that contamination by sublimable components is reduced. Particularly, for a display material, a material that achieves all of high sensitivity, high heat resistance, and hygroscopic reliability with reduced deterioration in image quality due to significant contamination can be obtained.

In the case of using the composition of the present embodiment for resist permanent film purposes, a curing agent as well as, if required, various additive agents such as an additional resin, a surfactant, a dye, a filler, a crosslinking agent, and a dissolution promoting agent can be added and dissolved in an organic solvent to prepare a composition for resist permanent films.

The composition of the present embodiment can be prepared by adding each of the above components and mixing them using a stirrer or the like. When the composition of the present embodiment contains a filler or a pigment, it can be prepared by dispersion or mixing using a dispersion apparatus such as a dissolver, a homogenizer, and a three-roll mill.

[Method for Purifying Compound or Resin]

The method for purifying the compound or the resin of the present embodiment comprises: an extraction step of bringing a solution containing the compound or the resin of the present embodiment and an organic solvent that does not inadvertently mix with water into contact with an acidic aqueous solution, thereby carrying out extraction. More specifically, in the purification method of the present embodiment, the compound or the resin of the present embodiment is dissolved in an organic solvent that does not inadvertently mix with water; the resultant solution is brought into contact with an acidic aqueous solution to carry out an extraction treatment, thereby transferring metals contained in the solution (A) containing the compound or the resin of the present embodiment and the organic solvent to the aqueous phase; and then the organic phase and the aqueous phase are separated and purified. Through the purification method of the present embodiment, the content of various metals in the compound or the resin of the present embodiment can be significantly reduced.

In the present embodiment, the "organic solvent that does not inadvertently mix with water" means that the solubility is less than 50% by mass in water at 20° C., and preferably less than 25% by mass from the viewpoint of productivity. The organic solvent that does not inadvertently mix with water is not particularly limited, and is preferably an organic solvent that is safely applicable to semiconductor manufacturing processes. Normally, the amount of the organic solvent used is approximately 1 to 100 times by weight relative to the compound or the resin of the present embodiment.

Specific examples of the solvent to be used include those described in International Publication No. WO 2015/080240. These solvents are used alone as one kind or in combination of two or more kinds. Among them, toluene, 2-heptanone, cyclohexanone, cyclopentanone, methyl isobutyl ketone, propylene glycol monomethyl ether acetate, ethyl acetate, and the like are preferable, and cyclohexanone and propylene glycol monomethyl ether acetate are particularly preferable.

The acidic aqueous solution to be used is appropriately selected from aqueous solutions in which generally known organic or inorganic compounds are dissolved in water. Examples thereof also include those described in International Publication No. WO 2015/080240. These acidic aqueous solutions are used alone as one kind or in combination of two or more kinds. Among them, an aqueous solution of sulfuric acid, nitric acid, and a carboxylic acid such as acetic acid, oxalic acid, tartaric acid and citric acid are preferable; an aqueous solution of sulfuric acid, oxalic acid, tartaric acid and citric acid are still more preferable; and an aqueous solution of oxalic acid is particularly preferable. It is considered that a polyvalent carboxylic acid such as oxalic acid, tartaric acid and citric acid coordinates with metal ions and provides a chelating effect, and thus is capable of removing more metals. In addition, as the water used herein, water, the metal content of which is small, such as ion exchanged water, is suitably used according to the purpose of the present invention.

The pH of the acidic aqueous solution to be used in the present embodiment is not particularly limited; however, when the acidity of the aqueous solution is too high, it may have a negative influence on the compound represented by the formula (1) or the resin having a constitutional unit derived from the compound, which is not preferable. Normally, the pH range is about 0 to 5, and is more preferably about pH 0 to 3.

The amount of the acidic aqueous solution to be used in the present embodiment is not particularly limited; however, when the amount is too small, it is required to increase the number of extraction treatments for removing metals, and on the other hand, when the amount of the aqueous solution is too large, the entire fluid volume becomes large, which may cause operational problems. The amount of the aqueous solution used is usually 10 to 200% by mass, and preferably 20 to 100% by mass, based on the solution of the compound or the resin of the present embodiment dissolved in an organic solvent.

In the present embodiment, for example, by bringing the acidic aqueous solution as described above into contact with the solution (A) containing the compound or the resin of the present embodiment and the organic solvent that does not inadvertently mix with water, metals are extracted.

The temperature when extraction treatment is carried out is generally in the range of 20 to 90° C., and preferably 30 to 80° C. The extraction operation is carried out, for example, by thoroughly mixing the solution (A) and the acidic aqueous solution by stirring or the like and then leaving the obtained mixed solution to stand still. Thereby, metals contained in the solution containing the compound or the resin of the present embodiment and the organic solvent are transferred to the aqueous phase. Also, by this operation, the acidity of the solution is lowered, and the degradation of the compound or the resin of the present embodiment can be suppressed.

The obtained mixture is separated into an aqueous phase and a solution phase containing the compound or the resin of the present embodiment and the organic solvent, and thus the solution containing the compound or the resin of the present embodiment and the organic solvent is recovered by decantation or the like. The time for leaving the mixed solution to stand still is not particularly limited; however, when the time for leaving the mixed solution to stand still is too short, separation of the solution phase containing the organic solvent and the aqueous phase becomes poor, which is not preferable. Normally, the time for leaving the mixed solution to stand still is 1 minute or longer, more preferably 10 minutes or longer, and still more preferably 30 minutes or longer. While the extraction treatment may be carried out only once, it is also effective to repeat mixing, leaving-to-stand-still, and separating operations multiple times.

When such an extraction treatment is carried out using the acidic aqueous solution, after the treatment, it is preferable to further subject the recovered solution (A), which has been extracted from the aqueous solution and contains the compound or the resin of the present embodiment and the organic solvent, to an extraction treatment with water. The extraction operation is carried out by thoroughly mixing the solution (A) and water by stirring or the like and then leaving the obtained mixed solution to stand still. The resultant solution is separated into an aqueous phase and a solution phase containing the compound or the resin of the present embodiment and the organic solvent, and thus the solution phase containing the compound or the resin of the present embodiment and the organic solvent is recovered by decantation or the like. In addition, as the water used herein, water, the metal content of which is small, such as ion exchanged water, is preferable according to the purpose of the present invention. While the extraction treatment may be carried out only once, it is also effective to repeat mixing, leaving-to-stand-still, and separating operations multiple times. The proportions of both used in the extraction treatment and the temperature, time, and other conditions are not particularly limited, and may be the same as those of the previous contact treatment with the acidic aqueous solution.

Water that is present in the thus-obtained solution containing the compound or the resin of the present embodiment and the organic solvent can be easily removed by performing vacuum distillation or a like operation. Also, if required, the concentration of the compound or the resin of the present embodiment can be regulated to be any concentration by adding an organic solvent.

For the method for obtaining the compound or the resin of the present embodiment alone from the obtained solution containing the compound or the resin of the present embodiment and the organic solvent, a publicly known method can be carried out, such as reduced-pressure removal, separation by reprecipitation, and a combination thereof. A publicly known treatment such as concentration operation, filtration operation, centrifugation operation and drying operation can be carried out, if required.

EXAMPLES

The present embodiment will be described in more detail with reference to synthesis examples and examples below. However, the present embodiment is not limited to these examples by any means.

(Carbon Concentration and Oxygen Concentration)

The carbon concentration and the oxygen concentration (% by mass) of the compound or the resin were measured by organic elemental analysis by using a product manufactured by Yaic. Yanaco, "CHN Coder MT-6".

(Molecular Weight)

The molecular weight of the compound or the resin was measured through LC-MS analysis by using a product manufactured by Waters Corp., "Acquity UPLC/MALDI-Synapt HDMS".

(Evaluation of Solubility)

At 23° C., the compound or the resin was dissolved in propylene glycol monomethyl ether (PGME) to form a 5 mass % solution. Subsequently, the solubility after leaving the solution to stand still at 5° C. for 30 days was evaluated according to the following criteria.

Evaluation A: no precipitate was visually confirmed
Evaluation C: precipitates were visually confirmed (Synthesis Working Example 1) Synthesis of BiP-1

To a container (internal capacity: 1000 mL) equipped with a stirrer, a condenser tube, and a burette, 100 g of 2,2-bis (4-hydroxyphenyl)propane (a reagent manufactured by Sigma-Aldrich), 3 g of sulfuric acid, 27 g of 4-biphenylaldehyde (a product manufactured by Mitsubishi Gas Chemical Company, Inc.), 415 g of 1-methoxy-2-propanol were added, and the contents were reacted by being stirred at 90° C. for 6 hours to obtain a reaction liquid. The reaction liquid was cooled and concentrated, 369 g of o-xylene and 123 g of butyl acetate were added thereto, and washed with aqueous sodium carbonate solution or pure water. Subsequently, an aqueous sodium hydroxide solution was added thereto, and the aqueous layer was recovered, extracted with ethyl acetate solvent, concentrated, and separated by column chromatography to obtain 20.0 g of the objective compound (BiP-1) represented by the following formula (BiP-1).

As a result of measuring the molecular weight of the obtained compound (BiP-1) by the above method, it was 620. In addition, the carbon concentration of the obtained compound (BiP-1) was 83.2% by mass, and the oxygen concentration thereof was 10.3% by mass.

The following peaks were found by $^1$H-NMR (500 MHz, DMSO-$d_6$) measurement performed on the obtained compound (BiP-1), and the compound was confirmed to have a chemical structure of the following formula (BiP-1). δ (ppm): 9.06-9.12 (4H, O—H), 6.59-7.64 (23H, Ph-H), 6.08 (1H, C—H), 1.37-1.39 (12H, —C(CH3)2)

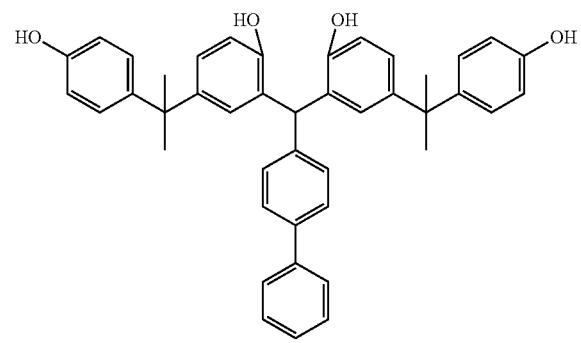

(BiP-1)

(Synthesis Working Example 2) Synthesis of BiP-2

In the same reaction as in Synthesis Working Example 1 except that 2,2-bis (4-hydroxyphenyl) hexafluoropropane was used instead of 2,2-bis(4-hydroxyphenyl)propane, 15 g of the objective compound (BiP-2) represented by the following formula (BiP-2) was obtained.

As a result of measuring the molecular weight of the obtained compound (BiP-2) by the above method, it was 836. In addition, the carbon concentration of the obtained compound (BiP-2) was 61.7% by mass, and the oxygen concentration thereof was 7.7% by mass.

The following peaks were found by $^1$H-NMR (500 MHz, DMSO-$d_6$) measurement performed on the obtained compound (BiP-2), and the compound was confirmed to have a chemical structure of the following formula (BiP-2). δ (ppm): 9.20-9.24 (4H, O—H), 6.68-7.54 (23H, Ph-H), 6.02 (1H, C—H)

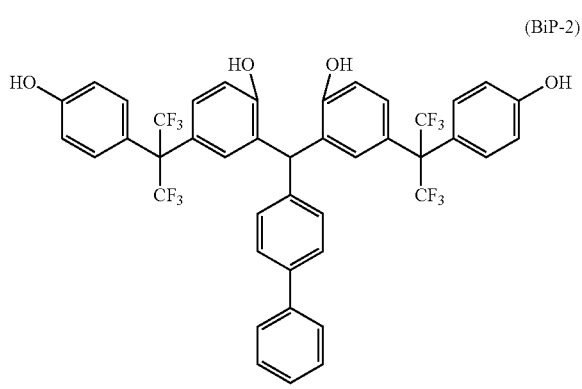 [SMILES: Oc1ccc(C(c2ccc(O)c(C(c3ccc(-c4ccccc4)cc3)c3cc(C(c4ccc(O)cc4)(C(F)(F)F)C(F)(F)F)ccc3O)c2)(C(F)(F)F)C(F)(F)F)cc1]

(BiP-2)

(Synthesis Working Example 3) Synthesis of BiP-3

In the same reaction as in Synthesis Working Example 1 except that 2,2-bis(4-hydroxy-3-methylphenyl)propane was used instead of 2,2-bis(4-hydroxyphenyl)propane, 15 g of the objective compound (BiP-3) represented by the following formula (BiP-3) was obtained.

As a result of measuring the molecular weight of the obtained compound (BiP-3) by the above method, it was 676. In addition, the carbon concentration of the obtained compound (BiP-3) was 83.4% by mass, and the oxygen concentration thereof was 95.0% by mass.

The following peaks were found by $^1$H-NMR (500 MHz, DMSO-$d_6$) measurement performed on the obtained compound (BiP-3), and the compound was confirmed to have a chemical structure of the following formula (BiP-3). δ (ppm): 9.00-9.05 (4H, O—H), 6.44-7.55 (19H, Ph-H), 6.12 (1H, C—H), 1.96-2.02 (12H, —CH3) 1.29-1.37 (12H, —C (CH3) 2)

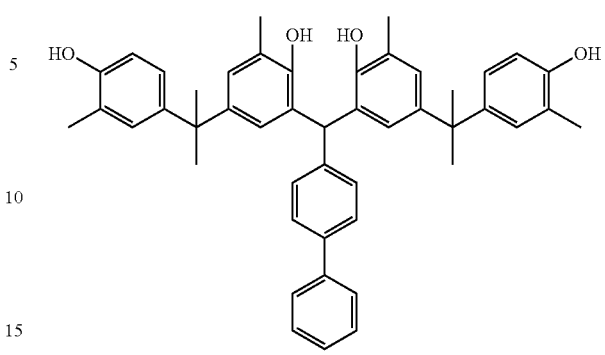

(BiP-3)

(Synthesis Working Example 4) Synthesis of BiP-4

In the same reaction as in Synthesis Working Example 1 except that 2,3,4,4'-tetrahydroxybenzophenone was used instead of 2,2-bis(4-hydroxyphenyl)propane, 18 g of the objective compound (BiP-4) represented by the following formula (BiP-4) was obtained.

As a result of measuring the molecular weight of the obtained compound (BiP-4) by the above method, it was 656. In addition, the carbon concentration of the obtained compound (BiP-4) was 71.3% by mass, and the oxygen concentration thereof was 24.4% by mass.

The following peaks were found by $^1$H-NMR (500 MHz, DMSO-$d_6$) measurement performed on the obtained compound (BiP-4), and the compound was confirmed to have a chemical structure of the following formula (BiP-4). δ (ppm): 9.07, 9.80, 10.18, 12.47 (8H, O—H), 6.54-7.59 (19H, Ph-H), 5.89 (1H, C—H)

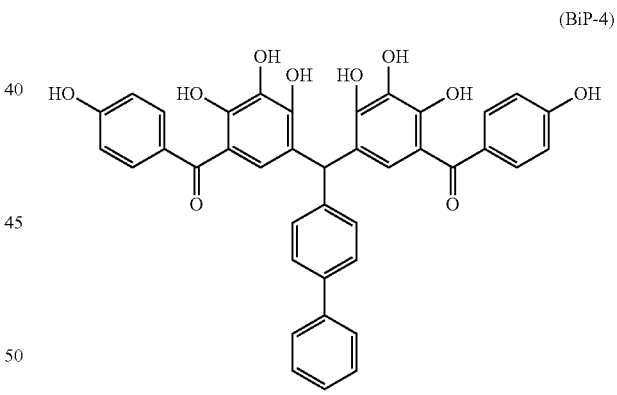

(BiP-4)

(Synthesis Working Example 5) Synthesis of RBiP-1

To a container (internal capacity: 1000 mL) equipped with a stirrer, a condenser tube, and a burette, 100 g of 2,2-bis (4-hydroxyphenyl)propane (a reagent manufactured by Sigma-Aldrich), 3 g of sulfuric acid, 27 g of 4-biphenylaldehyde (a product manufactured by Mitsubishi Gas Chemical Company, Inc.), 415 g of 1-methoxy-2-propanol were added, and the contents were reacted by being stirred at 90° C. for 6 hours to obtain a reaction liquid. The reaction liquid was cooled and concentrated, 369 g of o-xylene and 123 g of butyl acetate were added thereto, and washed with aqueous sodium carbonate solution or pure water. Subsequently, an aqueous sodium hydroxide solution was added thereto, and the aqueous layer was recovered, extracted with ethyl acetate solvent, and concentrated. 1000 g of heptane was added thereto and the solid matter was precipitated and separated to obtain 98.0 g of the objective resin (RBiP-1) represented by the following formula (RBiP-1).

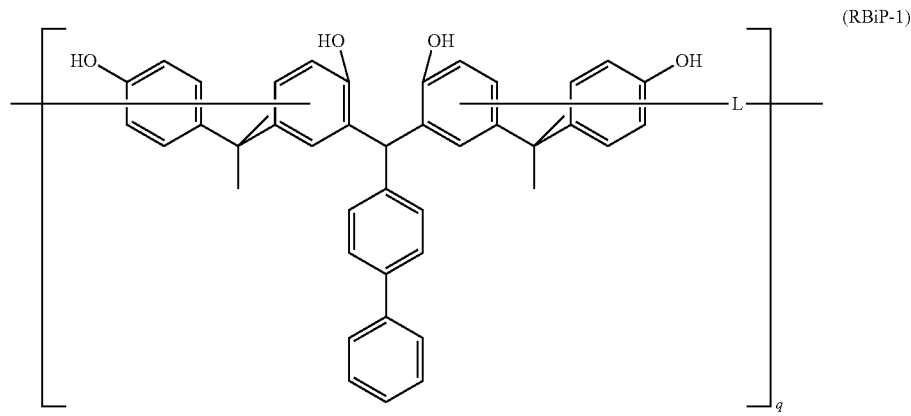

(RBiP-1)

(In the formula (RBiP-1), L represents a residue derived from 4-biphenylaldehyde and q represents the number of repeat units.)

(Synthesis Working Example 6) Synthesis of RBiP-2

In the same reaction as in Synthesis Working Example 5 except that 2,2-bis(4-hydroxyphenyl)hexafluoropropane was used instead of 2,2-bis(4-hydroxyphenyl)propane, 8.0 g of the objective resin (RBiP-2) represented by the following formula (RBiP-2) was obtained.

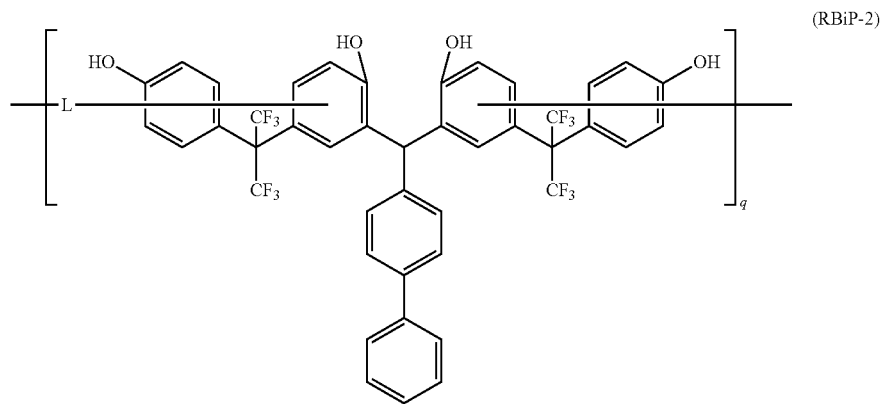

(RBiP-2)

(In the formula (RBiP-2), L represents a residue derived from 4-biphenylaldehyde and q represents the number of repeat units.)

(Synthesis Working Example 7) Synthesis of RBiP-3

In the same reaction as in Synthesis Working Example 5 except that 2,2-bis (4-hydroxy-3-methylphenyl) propane was used instead of 2,2-bis(4-hydroxyphenyl)propane, 8.9 g of the objective resin (RBiP-3) represented by the following formula (RBiP-3) was obtained.

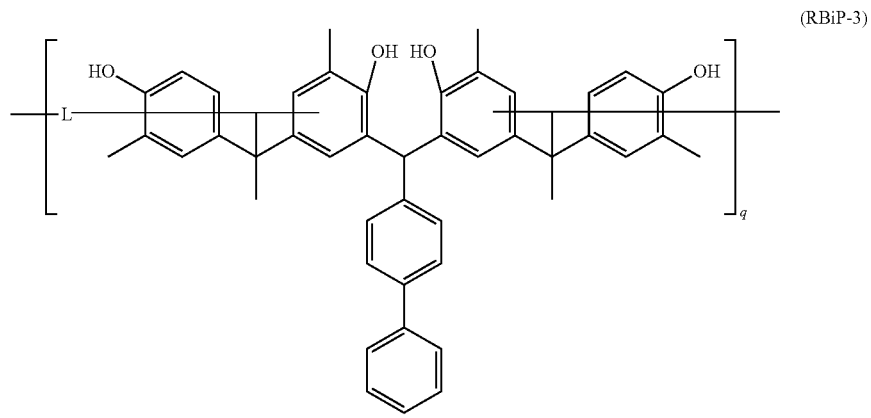

(In the formula (RBiP-3), L represents a residue derived from 4-biphenylaldehyde and q represents the number of repeat units.)

(Synthesis Working Example 8) Synthesis of RBiP-4

In the same reaction as in Synthesis Working Example 5 except that 2,3,4,4'-tetrahydroxybenzophenone was used instead of 2,2-bis(4-hydroxyphenyl)propane, 7.0 g of the objective resin (RBiP-4) represented by the following formula (RBiP-4) was obtained.

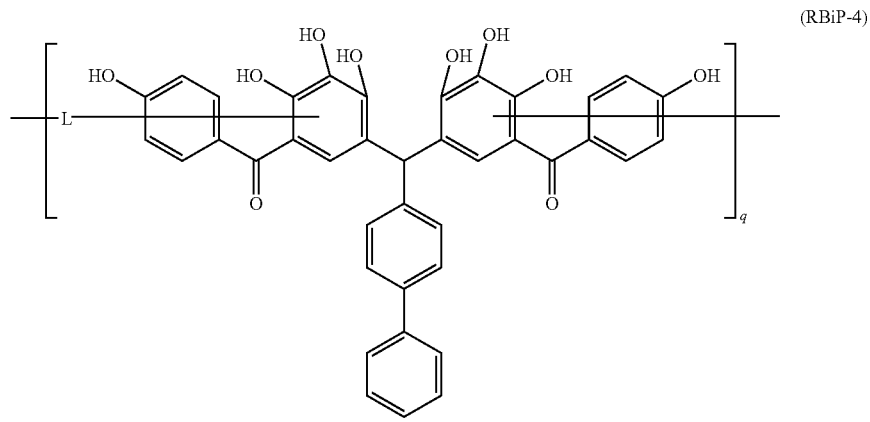

(In the formula (RBiP-4), L represents a residue derived from benzaldehyde and q represents the number of repeat units.)

(Synthesis Working Example 9) Synthesis of BiP-5

In the same reaction as in Synthesis Working Example 1 except that 2-naphthaldehyde was used instead of 4-biphenylaldehyde, 1.6 g of the objective compound (BiP-5) represented by the following formula (BiP-5) was obtained.

As a result of measuring the molecular weight of the obtained compound (BiP-5) by the above method, it was 542. In addition, the carbon concentration of the obtained compound (BiP-5) was 77.5% by mass, and the oxygen concentration thereof was 17.7% by mass.

The following peaks were found by $^1$H-NMR (500 MHz, DMSO-$d_6$) measurement performed on the obtained compound (BiP-5), and the compound was confirmed to have a chemical structure of the following formula (BiP-5). δ (ppm): 9.18 (4H, O—H), 6.45-7.69 (21H, Ph-H), 6.08 (1H, C—H 1.30-1.36 (12H, —C(CH3)2)

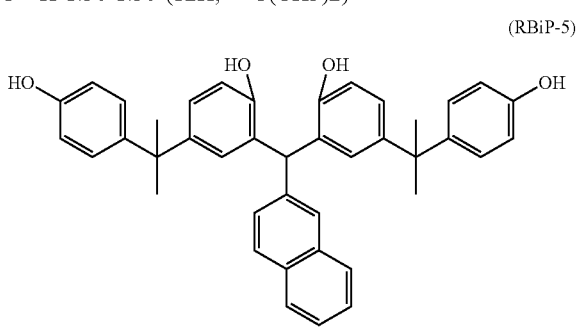

(Synthesis Working Example 10) Synthesis of RBiP-5

In the same reaction as in Synthesis Working Example 5 except that 2-naphthaldehyde was used instead of 4-biphenylaldehyde, 11.0 g of the objective resin (RBiP-5) represented by the following formula (RBiP-5) was obtained.

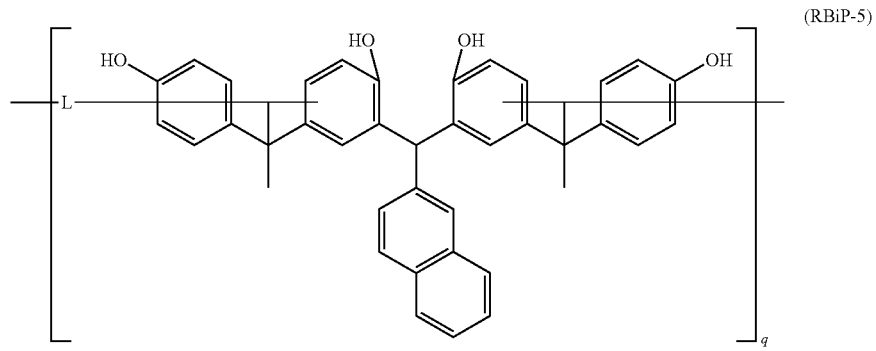

(In the formula (RBiP-5), L represents a residue derived from 2-naphthaldehyde and q represents the number of repeat units.)

(Synthesis Working Example 11) Synthesis of BiP-6

In the same reaction as in Synthesis Working Example 1 except that 2,2'-dimethylpropanal was used instead of 4-biphenylaldehyde, 0.5 g of the objective compound (BiP-6) represented by the following formula (BiP-6) was obtained.

As a result of measuring the molecular weight of the obtained compound (BiP-6) by the above method, it was 472. In addition, the carbon concentration of the obtained compound (BiP-6) was 73.7% by mass, and the oxygen concentration thereof was 20.3% by mass.

The following peaks were found by $^1$H-NMR (500 MHz, DMSO-$d_6$) measurement performed on the obtained compound (BiP-6), and the compound was confirmed to have a chemical structure of the following formula (BiP-6). δ (ppm): 9.04 (4H, O—H), 6.45-7.69 (21H, Ph-H), 5.98 (1H, C—H), 1.73-1.88 (9H, —C(CH3)), 1.32-1.38 (12H, —C(CH3)2)

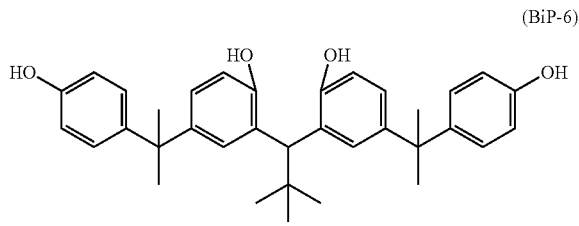 [SMILES: CC(C)(c1ccc(O)cc1)c1ccc(O)c(C(c2cc(C(C)(C)c3ccc(O)cc3)ccc2O)C(C)(C)C)c1]

(Synthesis Working Example 12) Synthesis of RBiP-6

In the same reaction as in Synthesis Working Example 5 except that 2,2'-dimethylpropanal was used instead of 4-biphenylaldehyde, 5.5 g of the objective resin (RBiP-6) represented by the following formula (RBiP-6) was obtained.

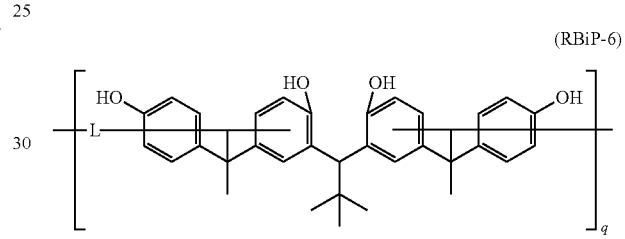

(In the formula (RBiP-6), L represents a residue derived from 2,2'-dimethylpropanal and q represents the number of repeat units.)

Synthetic Example 1

A four necked flask (internal capacity: 10 L) equipped with a Dimroth condenser tube, a thermometer, and a stirring blade and having a detachable bottom was prepared. To this four necked flask, 1.09 kg (7 mol) of 1,5-dimethylnaphthalene (manufactured by Mitsubishi Gas Chemical Company, Inc.), 2.1 kg (28 mol as formaldehyde) of a 40 mass % aqueous formalin solution (manufactured by Mitsubishi Gas Chemical Company, Inc.), and 0.97 mL of a 98 mass % sulfuric acid (manufactured by Kanto Chemical Co., Inc.) were added in a nitrogen stream, and the mixture was reacted for 7 hours while refluxed at 100° C. at normal pressure. Subsequently, 1.8 kg of ethylbenzene (special grade reagent manufactured by Wako Pure Chemical Industries, Ltd.) was added as a diluting solvent to the reaction liquid, and the mixture was left to stand still, followed by removal of an aqueous phase as a lower phase. Neutralization and washing with water were further performed, and ethylbenzene and unreacted 1,5-dimethylnaphthalene were distilled off under reduced pressure to obtain 1.25 kg of a dimethylnaphthalene formaldehyde resin as a light brown solid. The molecular weight of the obtained dimethylnaphthalene formaldehyde resin was as follows: number average molecular weight (Mn): 562, weight average molecular weight (Mw): 1168, and dispersity (Mw/Mn): 2.08.

Then, a four necked flask (internal capacity: 0.5 L) equipped with a Dimroth condenser tube, a thermometer, and a stirring blade was prepared. To this four necked flask, 100 g (0.51 mol) of the dimethylnaphthalene formaldehyde resin obtained as described above, and 0.05 g of p-toluenesulfonic acid were added in a nitrogen stream, and the temperature was raised to 190° C. at which the mixture was then heated for 2 hours, followed by stirring. Subsequently, 52.0 g (0.36 mol) of 1-naphthol was further added thereto, the temperature was further elevated to 220° C., and the mixture was reacted for 2 hours. After dilution with a solvent, neutralization and washing with water were performed, and the solvent was distilled off under reduced pressure to obtain 126.1 g of a modified resin (CR-1) as a black-brown solid.

The obtained resin (CR-1) had Mn: 885, Mw: 2220, and Mw/Mn: 2.51. In addition, the carbon concentration of the obtained resin (CR-1) was 89.1% by mass, and the oxygen concentration thereof was 4.5% by mass. Note that the Mn, Mw and Mw/Mn of the dimethylnaphthalene formaldehyde resin and the resin (CR-1) were determined by gel permeation chromatography (GPC) analysis under the following measurement conditions in terms of polystyrene.

Apparatus: Shodex GPC-101 model (a product manufactured by Showa Denko K.K.)
Column: KF-80M×3
Eluent: 1 mL/min THF
Temperature: 40° C.

Examples 1 to 14 and Comparative Example 1

For the above BiP-1 to BiP-6, RBiP-1 to RBiP-6 and CR-1, solubility test was carried out. The results are shown in Table 1. Also, underlayer film forming materials for lithography (underlayer film forming compositions for lithography) were each prepared according to the compositions shown in Table 1. Next, a silicon supporting material was spin coated with each of these underlayer film forming materials for lithography, and then baked at 240° C. for 60 seconds and further at 400° C. for 120 seconds to prepare each underlayer film with a film thickness of 200 nm. The following acid generating agent, crosslinking agent, and organic solvent were used.

Acid generating agent: a product manufactured by Midori Kagaku Co., Ltd., "di-tertiary butyl diphenyliodonium nonafluoromethanesulfonate" (in the table, designated as "DTDPI")

Crosslinking agent: a product manufactured by Sanwa Chemical Co., Ltd., "NIKALAC MX270" (in the table, designated as "NIKALAC")

Organic solvent: Propylene glycol monomethyl ether acetate (in the table, designated as "PGMEA")

For each of the obtained underlayer films, etching test was carried out under the following conditions to evaluate etching resistance. The evaluation results are shown in Table 1.

[Etching Test]
Etching apparatus: a product manufactured by Samco International, Inc., "RIE-10NR"
Output: 50 W
Pressure: 20 Pa
Time: 2 min
Etching Gas
Ar gas flow rate:$CF_4$ gas flow rate:$O_2$ gas flow rate=50:5:5 (sccm)

[Evaluation of Etching Resistance]
The evaluation of etching resistance was carried out by the following procedures.

First, an underlayer film containing a phenol novolac resin was prepared under the same conditions as in Example 1 except that a phenol novolac resin (PSM4357 manufactured by Gunei Chemical Industry Co., Ltd.) was used instead of the compound (BiP-1) used in Example 1. Then, the above etching test was carried out for this underlayer film containing a phenol novolac resin, and the etching rate (etching speed) was measured. Next, for each of the underlayer films of Examples and Comparative Example, the above etching test was carried out, and the etching rate was measured. Then, the etching resistance for each of Examples and Comparative Example was evaluated according to the following evaluation criteria on the basis of the etching rate of the underlayer film containing a phenol novolac resin.

[Evaluation Criteria]
A: The etching rate was less than −10% as compared with the underlayer film of novolac.
B: The etching rate was −10% to +5% as compared with the underlayer film of novolac.
C: The etching rate was more than +5% as compared with the underlayer film of novolac.

TABLE 1

|  | Compound or resin (parts by mass) | Solvent (parts by mass) | Acid generating agent (parts by mass) | Crosslinking agent (parts by mass) | Evaluation of solubility | Evaluation of etching resistance |
| --- | --- | --- | --- | --- | --- | --- |
| Example 1 | BiP-1 (10) | PGMEA (90) | — | — | A | A |
| Example 2 | BiP-1 (10) | PGMEA (90) | DTDPI (0.5) | NIKALAC (0.5) | A | A |
| Example 3 | RBiP-1 (10) | PGMEA (90) | — | — | A | A |
| Example 4 | RBiP-1 (10) | PGMEA (90) | DTDPI (0.5) | NIKALAC (0.5) | A | A |
| Example 5 | BiP-2 (10) | PGMEA (90) | DTDPI (0.5) | NIKALAC (0.5) | A | A |
| Example 6 | RBiP-2 (10) | PGMEA (90) | DTDPI (0.5) | NIKALAC (0.5) | A | A |
| Example 7 | BiP-3 (10) | PGMEA (90) | DTDPI (0.5) | NIKALAC (0.5) | A | A |
| Example 8 | RBiP-3 (10) | PGMEA (90) | DTDPI (0.5) | NIKALAC (0.5) | A | A |

TABLE 1-continued

| | Compound or resin (parts by mass) | Solvent (parts by mass) | Acid generating agent (parts by mass) | Crosslinking agent (parts by mass) | Evaluation of solubility | Evaluation of etching resistance |
|---|---|---|---|---|---|---|
| Example 9 | BiP-4 (10) | PGMEA (90) | DTDPI (0.5) | NIKALAC (0.5) | A | A |
| Example 10 | RBiP-4 (10) | PGMEA (90) | DTDPI (0.5) | NIKALAC (0.5) | A | A |
| Example 11 | BiP-5 (10) | PGMEA (90) | DTDPI (0.5) | NIKALAC (0.5) | A | A |
| Example 12 | RBiP-5 (10) | PGMEA (90) | DTDPI (0.5) | NIKALAC (0.5) | A | A |
| Example 13 | BiP-6 (10) | PGMEA (90) | DTDPI (0.5) | NIKALAC (0.5) | A | A |
| Example 14 | RBiP-6 (10) | PGMEA (90) | DTDPI (0.5) | NIKALAC (0.5) | A | A |
| Comparative Example 1 | CR-1 (10) | PGMEA (90) | DTDPI (0.5) | NIKALAC (0.5) | A | C |

Examples 15 to 28

A SiO$_2$ supporting material with a film thickness of 300 nm was coated with the solution of the underlayer film forming material for lithography prepared in each of the above Examples 1 to 14, and baked at 240° C. for 60 seconds and further at 400° C. for 120 seconds to form each underlayer film with a film thickness of 70 nm. This underlayer film was coated with a resist solution for ArF and baked at 130° C. for 60 seconds to form a photoresist layer with a film thickness of 140 nm. The ArF resist solution used was prepared by compounding 5 parts by mass of a compound represented by the formula (11) given below, 1 part by mass of triphenylsulfonium nonafluoromethanesulfonate, 2 parts by mass of tributylamine, and 92 parts by mass of PGMEA. For the compound represented by the formula (11) given below, 4.15 g of 2-methyl-2-methacryloyloxyadamantane, 3.00 g of methacryloyloxy-γ-butyrolactone, 2.08 g of 3-hydroxy-1-adamantyl methacrylate, and 0.38 g of azobisisobutyronitrile were dissolved in 80 mL of tetrahydrofuran to prepare a reaction solution. This reaction solution was polymerized for 22 hours with the reaction temperature kept at 63° C. in a nitrogen atmosphere. Then, the reaction solution was added dropwise into 400 mL of n-hexane. The product resin thus obtained was solidified and purified, and the resulting white powder was filtered and dried overnight at 40° C. under reduced pressure to obtain a compound represented by the following formula.

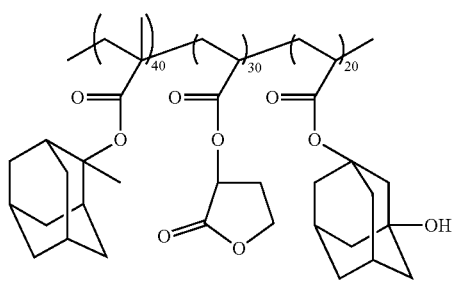

(11)

The numbers in the above formula (11) indicate the ratio of each constitutional unit.

Subsequently, the photoresist layer was exposed using an electron beam lithography system (manufactured by ELIONIX INC.; ELS-7500, 50 keV), baked (PEB) at 115° C. for 90 seconds, and developed for 60 seconds in a 2.38 mass % tetramethylammonium hydroxide (TMAH) aqueous solution to obtain a positive type resist pattern.

Defects of the obtained resist patterns of 55 nm L/S (1:1) and 80 nm L/S (1:1) were observed, and the results are shown in Table 2. In the table, "good" means that no major defects were found in the formed resist pattern, and "poor" means that major defects were found in the formed resist pattern.

Comparative Example 2

The same operations as in Example 15 were performed except that no underlayer film was formed so that a photoresist layer was formed directly on a SiO$_2$ supporting material to obtain a positive type resist pattern. The results are shown in Table 2.

TABLE 2

| | Underlayer film forming material | Resolution (nmL/S) | Sensitivity (μC/cm$^2$) | Resist pattern shape after development |
|---|---|---|---|---|
| Example 15 | Example 1 | 55 | 10 | Good |
| Example 16 | Example 2 | 55 | 10 | Good |
| Example 17 | Example 3 | 55 | 10 | Good |
| Example 18 | Example 4 | 55 | 10 | Good |
| Example 19 | Example 5 | 55 | 10 | Good |
| Example 20 | Example 6 | 55 | 10 | Good |
| Example 21 | Example 7 | 55 | 10 | Good |
| Example 22 | Example 8 | 55 | 10 | Good |
| Example 23 | Example 9 | 55 | 10 | Good |
| Example 24 | Example 10 | 55 | 10 | Good |
| Example 25 | Example 11 | 55 | 10 | Good |
| Example 26 | Example 12 | 55 | 10 | Good |
| Example 27 | Example 13 | 55 | 10 | Good |
| Example 28 | Example 14 | 55 | 10 | Good |
| Comparative Example 2 | — | 80 | 26 | Poor |

As is evident from Table 1, Examples 1 to 14 using any of the compounds or the resins of the present embodiment, BiP-1 to BiP-6 and RBiP-1 to RBiP-6, were confirmed to be good in terms of both solubility and etching resistance. On the other hand, Comparative Example 1 using CR-1 (phenol-modified dimethylnaphthaleneformaldehyde resin) resulted in poor etching resistance.

As is evident from Table 2, Examples 15 to 28 using any of the compounds or the resins of the present embodiment, BiP-1 to BiP-6 and RBiP-1 to RBiP-6, were confirmed to have a good resist pattern shape after development and have no major defects found. Furthermore, each of Examples 15 to 28 was confirmed to be significantly superior to Comparative Example 2, in which no underlayer film was formed, in both resolution and sensitivity. Here, a good resist pattern shape after development indicates that the underlayer film forming materials for lithography used in Examples 15 to 28 have good adhesiveness to a resist material (photoresist material and the like).

Examples 29 to 42

A $SiO_2$ supporting material with a film thickness of 300 nm was coated with the solution of the underlayer film forming material for lithography according to each of Examples 1 to 14, and baked at 240° C. for 60 seconds and further at 400° C. for 120 seconds to form each underlayer film with a film thickness of 80 nm. This underlayer film was coated with a silicon-containing intermediate layer material and baked at 200° C. for 60 seconds to form an intermediate layer film with a film thickness of 35 nm. This intermediate layer film was further coated with the above resist solution for ArF and baked at 130° C. for 60 seconds to form a photoresist layer with a film thickness of 150 nm. The silicon-containing intermediate layer material used was the silicon atom-containing polymer described in <Synthesis Example 1> of Japanese Patent Laid-Open No. 2007-226170. Subsequently, the photoresist layer was mask exposed using an electron beam lithography system (manufactured by ELIONIX INC.; ELS-7500, 50 keV), baked (PEB) at 115° C. for 90 seconds, and developed for 60 seconds in a 2.38 mass % tetramethylammonium hydroxide (TMAH) aqueous solution to obtain a 55 nm L/S (1:1) positive type resist pattern. Then, the silicon-containing intermediate layer film (SOG) was dry etched with the obtained resist pattern as a mask using RIE-10NR manufactured by Samco International, Inc. Subsequently, dry etching of the underlayer film with the obtained silicon-containing intermediate layer film pattern as a mask and dry etching of the $SiO_2$ film with the obtained underlayer film pattern as a mask were performed in order.

Respective etching conditions are as shown below.
Conditions for etching of resist intermediate layer film with resist pattern
 Output: 50 W
 Pressure: 20 Pa
 Time: 1 min
 Etching gas
 Ar gas flow rate:$CF_4$ gas flow rate:$O_2$ gas flow rate=50:8:2 (sccm)
Conditions for etching of resist underlayer film with resist intermediate film pattern
 Output: 50 W
 Pressure: 20 Pa
 Time: 2 min
 Etching gas
 Ar gas flow rate:$CF_4$ gas flow rate:$O_2$ gas flow rate=50:5:5 (sccm)
Conditions for etching of $SiO_2$ film with resist underlayer film pattern
 Output: 50 W
 Pressure: 20 Pa
 Time: 2 min
 Etching gas
 Ar gas flow rate:$C_5F_{12}$ gas flow rate:$C_2F_6$ gas flow rate:$O_2$ gas flow rate=50:4:3:1 (sccm)

[Evaluation]
The pattern cross section (that is, the shape of the $SiO_2$ film after etching) obtained as described above was observed by using a product manufactured by Hitachi, Ltd., "electron microscope (S-4800)". The observation results are shown in Table 3. In the table, "good" means that no major defects were found in the formed pattern cross section, and "poor" means that major defects were found in the formed pattern cross section.

TABLE 3

| | Underlayer film forming material | Shape of SiO2 film | Appearance |
|---|---|---|---|
| Example 29 | Example 1 | Rectangle | Good |
| Example 30 | Example 2 | Rectangle | Good |
| Example 31 | Example 3 | Rectangle | Good |
| Example 32 | Example 4 | Rectangle | Good |
| Example 33 | Example 5 | Rectangle | Good |
| Example 34 | Example 6 | Rectangle | Good |
| Example 35 | Example 7 | Rectangle | Good |
| Example 36 | Example 8 | Rectangle | Good |
| Example 37 | Example 9 | Rectangle | Good |
| Example 38 | Example 10 | Rectangle | Good |
| Example 39 | Example 11 | Rectangle | Good |
| Example 40 | Example 12 | Rectangle | Good |
| Example 41 | Example 13 | Rectangle | Good |
| Example 42 | Example 14 | Rectangle | Good |

Examples 43 to 48

A $SiO_2$ supporting material with a film thickness of 300 nm was coated with the solution of the optical component forming composition having the same composition as that of the solution of the underlayer film forming material for lithography prepared in each of the above Examples 1 to 6, and baked at 260° C. for 300 seconds to form each optical component forming film with a film thickness of 100 nm. Then, tests for the refractive index and the transparency at a wavelength of 633 nm were carried out by using a vacuum ultraviolet with variable angle spectroscopic ellipsometer (VUV-VASE) manufactured by J.A. Woollam Japan, and the refractive index and the transparency were evaluated according to the following criteria. The evaluation results are shown in Table 4.
[Evaluation Criteria for Refractive Index]
A: The refractive index is 1.60 or more.
C: The refractive index is less than 1.60.
[Evaluation Criteria for Transparency]
A: The absorption coefficient is less than 0.03.
C: The absorption coefficient is 0.03 or more.

TABLE 4

| | Underlayer film forming material | Refractive index | Transparency |
|---|---|---|---|
| Example 43 | Example 1 | A | A |
| Example 44 | Example 2 | A | A |
| Example 45 | Example 3 | A | A |
| Example 46 | Example 4 | A | A |
| Example 47 | Example 5 | A | A |
| Example 48 | Example 6 | A | A |

Examples 49 to 52 and Comparative Example 3

(Heat Resistance and Resist Performance)
Results of carrying out a heat resistance test and resist performance evaluation using BiP-1, BiP-2, RBiP-1, RBiP-2, and CR-1 are shown in Table 5.

(Preparation of Resist Composition)

By using each of the compounds or resins synthesized as described above, a resist composition was prepared according to the recipe shown in Table 5. For the components of the resist compositions in Table 5, the following acid generating agent (C), acid diffusion controlling agent (E), and solvent were used.

Acid generating agent (C)
- P-1: triphenylbenzenesulfonium trifluoromethanesulfonate (Midori Kagaku Co., Ltd.)

Acid diffusion controlling agent (E)
- Q-1: trioctylamine (Tokyo Kasei Kogyo Co., Ltd.) Solvent
- S-1: propylene glycol monomethyl ether (Tokyo Kasei Kogyo Co., Ltd.)

(Method for Evaluating Resist Performance of Resist Composition)

A clean silicon wafer was spin coated with the homogeneous resist composition, and then prebaked (PB) before exposure in an oven of 110° C. to form a resist film with a thickness of 60 nm. The obtained resist film was irradiated with electron beams of 1:1 line and space setting with a 50 nm interval using an electron beam lithography system (ELS-7500 manufactured by ELIONIX INC.). After irradiation, the resist film was heated at each predetermined temperature for 90 seconds, and immersed in a 2.38 mass % TMAH alkaline developing solution for 60 seconds for development. Subsequently, the resist film was washed with ultrapure water for 30 seconds, and dried to form a positive type resist pattern. Concerning the formed resist pattern, the line and space were observed by a scanning electron microscope (S-4800 manufactured by Hitachi High-Technologies Corporation) to evaluate the reactivity by electron beam irradiation of the resist composition.

In the table, "good" means that the resist pattern shape forms a rectangle and no defects are found, and "poor" means that the pattern does not form a rectangle or defects are found.

Examples 53 to 56 and Comparative Example 4

(Preparation of Radiation-Sensitive Composition)

The components set forth in Table 6 were formulated and formed into homogeneous solutions, and the obtained homogeneous solutions were filtered through a Teflon® membrane filter with a pore diameter of 0.1 μm to prepare radiation-sensitive compositions. Each of the prepared radiation-sensitive compositions was evaluated as described below.

The following resist base material was used in Comparative Example 4.

PHS-1: polyhydroxystyrene Mw=8000 (Sigma-Aldrich)

The following optically active compound (B) was used.

B-1: naphthoquinonediazide-based sensitizing agent having the following chemical structural formula (G) (4NT-300, Toyo Gosei Co., Ltd.)

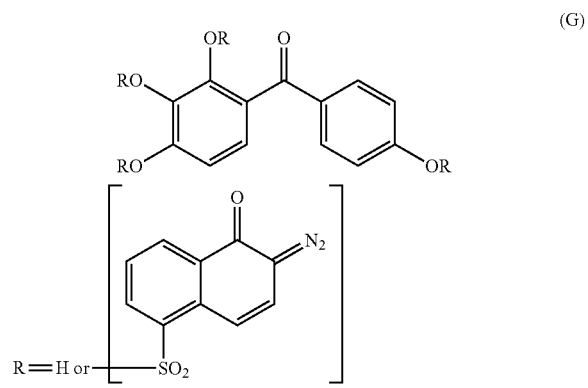

(G)

TABLE 5

|  | Compound/resin | Heat resistance evaluation | Resin [g] | P-1 [g] | Q-1 [g] | S-1 [g] | Resist performance evaluation |
|---|---|---|---|---|---|---|---|
| Example 49 | BiP-1 | A | 1.0 | 0.3 | 0.03 | 50.0 | Good |
| Example 50 | BiP-2 | A | 1.0 | 0.3 | 0.03 | 50.0 | Good |
| Example 51 | RBiP-1 | A | 1.0 | 0.3 | 0.03 | 50.0 | Good |
| Example 52 | RBiP-2 | A | 1.0 | 0.3 | 0.03 | 50.0 | Good |
| Comparative Example 3 | CR-1 | C | 1.0 | 0.3 | 0.03 | 50.0 | Poor |

As is evident from Table 5, it was confirmed that each of the compounds or resins used in Example 49 to Example 52 has good heat resistance whereas the compound used in Comparative Example 3 is inferior in heat resistance.

Also, in the resist pattern evaluation, a good resist pattern was obtained by irradiation with electron beams of 1:1 line and space setting with a 50 nm interval in each of Examples 49 to Example 52. On the other hand, it was not possible to obtain a good resist pattern in Comparative Example 3.

Thus, the resins that satisfy the requirements of the present invention have high heat resistance and can impart a good shape to a resist pattern, as compared with the comparative compound (CR-1). As long as the above requirements of the present invention are met, compounds other than the resins described in Examples also exhibit the same effects.

The following solvent was used.

S-1: propylene glycol monomethyl ether (Tokyo Kasei Kogyo Co., Ltd.)

TABLE 6

| | Composition | | |
|---|---|---|---|
| | Component (A) [g] | Optically active compound (B) [g]] | Solvent [g] |
| Example 53 | BiP-1 0.5 | B-1 1.5 | S-1 30.0 |
| Example 54 | BiP-2 0.5 | B-1 1.5 | S-1 30.0 |

TABLE 6-continued

| | Composition | | |
|---|---|---|---|
| | Component (A) [g] | Optically active compound (B) [g] | Solvent [g] |
| Example 55 | RBiP-1 0.5 | B-1 1.5 | S-1 30.0 |
| Example 56 | RBiP-2 0.5 | B-1 1.5 | S-1 30.0 |
| Comparative Example 4 | PHS-1 0.5 | B-1 1.5 | S-1 30.0 |

(Evaluation of Resist Performance of Radiation-Sensitive Composition)

A clean silicon wafer was spin coated with the radiation-sensitive composition obtained as described above, and then prebaked (PB) before exposure in an oven of 110° C. to form a resist film with a thickness of 200 nm. The resist film was exposed to ultraviolet using an ultraviolet exposure apparatus (mask aligner MA-10 manufactured by Mikasa Co., Ltd.). The ultraviolet lamp used was a super high pressure mercury lamp (relative intensity ratio: g-ray:h-ray:i-ray:j-ray=100:80:90:60). After irradiation, the resist film was heated at 110° C. for 90 seconds, and immersed in a 2.38 mass % TMAH alkaline developing solution for 60 seconds for development. Subsequently, the resist film was washed with ultrapure water for 30 seconds, and dried to form a 5 μm positive type resist pattern.

The obtained line and space were observed in the formed resist pattern by a scanning electron microscope (S-4800 manufactured by Hitachi High-Technologies Corporation). As for the line edge roughness, a pattern having asperities of less than 50 nm was evaluated to be good.

In the case of using the radiation-sensitive composition according to each of Examples 53 to 56, a good resist pattern with a resolution of 5 μm was able to be obtained. The roughness of the pattern was also small and good.

On the other hand, in the case of using the radiation-sensitive composition according to Comparative Example 4, a good resist pattern with a resolution of 5 μm was able to be obtained. However, the roughness of the pattern was large and poor.

As described above, it was found that each of the radiation-sensitive compositions according to Example 53 to Example 56 can form a resist pattern that has small roughness and a good shape, as compared with the radiation-sensitive composition according to Comparative Example 4. As long as the above requirements of the present invention are met, radiation-sensitive compositions other than those described in Examples also exhibit the same effects.

Each of the compounds or resins obtained in Synthesis Working Example 1 to Synthesis Working Example 4 has a relatively low molecular weight and a low viscosity. As such, the embedding properties and film surface flatness of underlayer film forming materials for lithography containing these compounds or resins can be relatively advantageously enhanced. Furthermore, each of these compounds or resins has a thermal decomposition temperature of 150° C. or higher (evaluation A) and has high heat resistance. Therefore, they can be used even under high temperature baking conditions.

(Example 57) Purification of BiP-1 with Acid

In a four necked flask (capacity: 1000 mL, with a detachable bottom), 150 g of a solution (10% by mass) formed by dissolving BiP-1 obtained in Synthesis Working Example 1 in PGMEA was charged, and was heated to 80° C. with stirring. Then, 37.5 g of an aqueous oxalic acid solution (pH 1.3) was added thereto, and the resultant mixture was stirred for 5 minutes and then left to stand for 30 minutes. This separated the mixture into an oil phase and an aqueous phase, and the aqueous phase was thus removed. After repeating this operation once, 37.5 g of ultrapure water was charged to the obtained oil phase, and after stirring for 5 minutes, the mixture was left to stand for 30 minutes and the aqueous phase was removed. After repeating this operation three times, the residual water and PGMEA were concentrated and removed by heating to 80° C. and reducing the pressure in the flask to 200 hPa or less. By diluting with PGMEA of EL grade (a reagent manufactured by Kanto Chemical Co., Inc.) such that the concentration of BiP-1 in PGMEA solution was adjusted to 10% by mass, a PGMEA solution of BiP-1 with a reduced metal content was obtained.

(Comparative Example 5) Purification of BiP-1 with Ultrapure Water

In the same manner as of Example 57 except that ultrapure water was used instead of the aqueous oxalic acid solution, and by adjusting the concentration to 10% by mass, a PGMEA solution of BiP-1 was obtained.

For the 10 mass % BiP-1 solution in PGMEA before the treatment, and the solutions obtained in Example 57 and Comparative Example 5, the contents of various metals were measured by ICP-MS. The measurement results are shown in Table 7.

TABLE 7

| | Metal content (ppb) | | | | | |
|---|---|---|---|---|---|---|
| | Na | Mg | K | Fe | Cu | Zn |
| Before treatment BiP-1 | >99 | 25.3 | >99 | >99 | 13.5 | 10.6 |
| Example 57 | 2.3 | 1.1 | 0.6 | 2.1 | 0.3 | 0.4 |
| Comparative Example 5 | 2.5 | 1.5 | 1.0 | >99 | 2.5 | 3.0 |

The compound and the resin of the present invention has high heat resistance, has high solvent solubility, and is applicable to a wet process. Therefore, a film forming material for lithography using the compound or the resin of the present invention, and a film for lithography thereof can be utilized widely and effectively in various applications that require such performances. Accordingly, the present invention can be utilized widely and effectively in, for example, electrical insulating materials, resins for resists, encapsulation resins for semiconductors, adhesives for printed circuit boards, electrical laminates mounted in electric equipment, electronic equipment, industrial equipment, and the like, matrix resins of prepregs mounted in electric equipment, electronic equipment, industrial equipment, and the like, buildup laminate materials, resins for fiber-reinforced plastics, resins for encapsulation of liquid crystal display panels, coating materials, various coating agents, adhesives, coating agents for semiconductors, resins for resists for semiconductors, resins for underlayer film formation, and the like. In particular, the present invention can be utilized particularly effectively in the field of films for lithography.

The invention claimed is:

1. A compound represented by the following formula (1):

$$(1)$$

[structure of formula (1) showing naphthalene/benzene rings with substituents $(R^2)_{m^2}$, $(R^3)_{m^3}$, $(R^4)_{m^4}$, $(R^5)_{m^5}$, linkers A, positions $p^2, p^3, p^4, p^5$, bracket subscript n, and terminal $R^1$]

wherein

A is a group having 1 to 12 carbon atoms;

$R^1$ is a 2n-valent group having 1 to 30 carbon atoms;

$R^2$ to $R^5$ are each independently a linear, branched, or cyclic alkyl group having 1 to 10 carbon atoms, an alkoxy group having 1 to 10 carbon atoms, an aryl group having 6 to 10 carbon atoms, an alkenyl group having 2 to 10 carbon atoms, an alkynyl group having 2 to 10 carbon atoms, a thiol group, or a hydroxyl group;

at least one $R^4$ and/or at least one $R^5$ is a hydroxy group and/or a thiol group;

$m^2$ and $m^3$ are each independently an integer of 0 to 8;

$m^4$ and $m^5$ are each independently an integer of 0 to 9;

n is an integer of 1 to 4; and $p^2$ to $p^5$ are each independently an integer of 0 to 2.

2. The compound according to claim 1, wherein, in the above formula (1), at least one $R^2$ and/or at least one $R^3$ is a hydroxy group and/or a thiol group.

3. The compound according to claim 1, wherein the compound represented by the above formula (1) is a compound represented by the following formula (1a):

$$(1a)$$

[structure of formula (1a) with substituents $(R^2)_{m^2}$, $(R^3)_{m^3}$, $(R^4)_{m^4}$, $(R^5)_{m^5}$, linker A, $R^{1a}$, $R^{1b}$, bracket subscript n]

wherein

A, $R^2$ to $R^5$, and n are each as defined in the above formula (1);

$R^{1a}$ is a hydrogen atom or a monovalent group having 1 to 10 carbon atoms;

$R^{1b}$ is an n-valent group having 1 to 25 carbon atoms;

$m^2$ and $m^3$ are each independently an integer of 0 to 4; and $m^4$ and $m^5$ are each independently an integer of 0 to 5.

4. The compound according to claim 3, wherein the compound represented by the above formula (1a) is a compound represented by the following formula (1b):

$$(1b)$$

[structure of formula (1b) with substituents $(R^4)_{m^4}$, $(R^5)_{m^5}$, $(R^6)_{m^6}$, $(R^7)_{m^7}$, $OR^{10}$, $OR^{11}$, linker A, $R^{1a}$, $R^{1b}$, bracket subscript n]

wherein

A, $R^4$, $R^5$, $R^{1a}$, $R^{1b}$, $m^4$, $m^5$, and n are each as defined in the above formula (1a);

$R^6$ and $R^7$ are each independently a linear, branched, or cyclic alkyl group having 1 to 10 carbon atoms, an aryl group having 6 to 10 carbon atoms, an alkenyl group having 2 to 10 carbon atoms, an alkynyl group having 2 to 10 carbon atoms, a thiol group, or a hydroxyl group;

$m^6$ and $m^7$ are each independently an integer of 0 to 3; and $R^{10}$ and $R^{11}$ are a hydrogen atom.

5. The compound according to claim 4, wherein the compound represented by the above formula 1b is a compound represented b the following formula (1c):

$$(1c)$$

[structure of formula (1c) with substituents $(R^6)_{m^6}$, $(R^7)_{m^7}$, $(R^8)_{m^8}$, $(R^9)_{m^9}$, $R^{12}O$, $R^{13}O$, $OR^{10}$, $OR^{11}$, linker A, $R^{1a}$, $R^{1b}$, bracket subscript n]

wherein

A, $R^{1a}$, $R^{1b}$, $R^6$, $R^7$, $R^{10}$, $R^{11}$, $m^6$, $m^7$, and n are each as defined in the above formula (1b);

$R^8$ and $R^9$ are each independently a linear, branched, or cyclic alkyl group having 1 to 10 carbon atoms, an aryl group having 6 to 10 carbon atoms, an alkenyl group having 2 to 10 carbon atoms, an alkynyl group having 2 to 10 carbon atoms, a thiol group, or a hydroxyl group;

$m^8$ and $m^9$ are each independently an integer of 0 to 4; and $R^{12}$ and $R^{13}$ are a hydrogen atom.

6. A resin having a constitutional unit derived from the compound according to claim 1.

7. The resin according to claim 6, wherein the resin has a structure represented by the following formula (2):

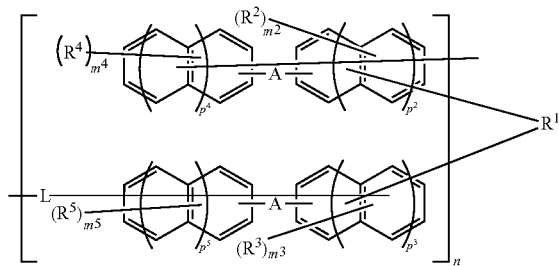

(2)

wherein

A, $R^1$ to $R^5$, $m^2$ to $m^5$, n, and $p^2$ to $p^5$ are each as defined in the above formula (1); and L is a single bond or a linking group.

8. A composition comprising the compound according to claim 1.

9. The composition according to claim 8, further comprising a solvent.

10. The composition according to claim 8, further comprising an acid generating agent.

11. The composition according to claim 8, further comprising a crosslinking agent.

12. The composition according to claim 8, wherein the composition is used in film formation for lithography.

13. The composition according to claim 8, wherein the composition is used in optical component formation.

14. A method for forming a resist pattern, comprising the steps of:
- a photoresist layer formation step of forming a photoresist layer on a supporting material using the composition according to claim 12; and
- a development step of irradiating a predetermined region of the photoresist layer formed through the photoresist layer formation step with radiation for development.

15. The method for forming a resist pattern according to claim 14, wherein the resist pattern is an insulating film pattern.

16. A method for forming a resist pattern, comprising:
- an underlayer film formation step of forming an underlayer film on a supporting material using the composition according to claim 12;
- a photoresist layer formation step of forming at least one photoresist layer on the underlayer film formed through the underlayer film formation step; and
- a step of irradiating a predetermined region of the photoresist layer formed through the photoresist layer formation step with radiation for development.

17. A method for forming a circuit pattern, comprising:
- an underlayer film formation step of forming an underlayer film on a supporting material using the composition according to claim 12;
- an intermediate layer film formation step of forming an intermediate layer film on the underlayer film formed through the underlayer film formation step;
- a photoresist layer formation step of forming at least one photoresist layer on the intermediate layer film formed through the intermediate layer film formation step;
- a resist pattern formation step of irradiating a predetermined region of the photoresist layer formed through the photoresist layer formation step with radiation for development, thereby forming a resist pattern;
- an intermediate layer film pattern formation step of etching the intermediate layer film with the resist pattern formed through the resist pattern formation step as a mask, thereby forming an intermediate layer film pattern;
- an underlayer film pattern formation step of etching the underlayer film with the intermediate layer film pattern formed through the intermediate layer film pattern formation step as a mask, thereby forming an underlayer film pattern; and
- a supporting material pattern formation step of etching the supporting material with the underlayer film pattern formed through the underlayer film pattern formation step as a mask, thereby forming a pattern on the supporting material.

18. A method for purifying the compound according to claim 1, comprising:
- an extraction step of bringing a solution containing the compound and an organic solvent that does not inadvertently mix with water into contact with an acidic aqueous solution, thereby carrying out extraction.

* * * * *

UNITED STATES PATENT AND TRADEMARK OFFICE
CERTIFICATE OF CORRECTION

PATENT NO. : 11,747,728 B2
APPLICATION NO. : 17/044772
DATED : September 5, 2023
INVENTOR(S) : Junya Horiuchi et al.

It is certified that error appears in the above-identified patent and that said Letters Patent is hereby corrected as shown below:

In the Claims

In Column 94, Claim 5, Line 34, delete "b the" and insert -- by the --, therefor.

Signed and Sealed this
Twenty-sixth Day of March, 2024

Katherine Kelly Vidal
*Director of the United States Patent and Trademark Office*